United States Patent
Nonaka et al.

(10) Patent No.: US 9,802,992 B2
(45) Date of Patent: Oct. 31, 2017

(54) CELL INTO WHICH PROTEIN, WHICH CAN SERVE AS POLYMERIZATION NUCLEUS OF PROTEIN POLYMER, OR POLYMER THEREOF IS INTRODUCED, AND METHOD FOR PRODUCTION OF THE CELL

(75) Inventors: Takashi Nonaka, Tokyo (JP); Sayuri Watanabe, Amagasaki (JP); Masami Masuda, Fujimi (JP); Masato Hasegawa, Chofu (JP)

(73) Assignee: TOKYO METROPOLITAN INSTITUTE OF MEDICAL SCIENCE, Tokyo (JP)

( * ) Notice: Subject to any disclaimer, the term of this patent is extended or adjusted under 35 U.S.C. 154(b) by 580 days.

(21) Appl. No.: 12/086,124

(22) PCT Filed: Dec. 6, 2006

(86) PCT No.: PCT/JP2006/324786
§ 371 (c)(1),
(2), (4) Date: Dec. 9, 2008

(87) PCT Pub. No.: WO2007/066809
PCT Pub. Date: Jun. 14, 2007

(65) Prior Publication Data
US 2010/0047826 A1 Feb. 25, 2010

(30) Foreign Application Priority Data
Dec. 6, 2005 (JP) .................................. 2005-352486

(51) Int. Cl.
*C12N 5/079* (2010.01)
*C12N 5/0793* (2010.01)
*G01N 33/50* (2006.01)
*C07K 14/47* (2006.01)
*G01N 33/68* (2006.01)

(52) U.S. Cl.
CPC ............. *C07K 14/47* (2013.01); *C12N 5/0619* (2013.01); *C12N 5/0622* (2013.01); *G01N 33/5058* (2013.01); *G01N 33/6896* (2013.01); *C12N 2503/02* (2013.01); *C12N 2510/00* (2013.01); *G01N 2500/10* (2013.01)

(58) Field of Classification Search
CPC ........... G01N 33/5058; G01N 33/6896; C07K 14/4711; C12N 5/0619; C12N 5/0622; C12N 2503/02
See application file for complete search history.

(56) References Cited

U.S. PATENT DOCUMENTS

2003/0054007 A1* 3/2003 Felgner et al. ............ 424/178.1
2004/0078835 A1   4/2004 Wischik et al.
2006/0259986 A1* 11/2006 Chilcote et al. .................. 800/3
2007/0192879 A1   8/2007 Yoshimoto et al.

FOREIGN PATENT DOCUMENTS

| EP | 0 908 727 A1 | 4/1999 |
|---|---|---|
| JP | 11-239488 A | 9/1999 |
| JP | 2004-531224 | 10/2004 |
| JP | 2004-538013 A | 12/2004 |
| WO | WO-02/10201 A2 | 2/2002 |
| WO | WO-02/13837 A1 | 2/2002 |
| WO | WO 03/015507 A1 | 2/2003 |
| WO | WO 2005/041649 A1 | 5/2005 |

OTHER PUBLICATIONS

Anderson JP et al. Phosphorylation of Ser-129 is the dominant pathological modification of alpha-synuclein in familial and sporadic Lewy body disease. J Biol Chem. 2006; 281: 29739-29752.*
Schell H et al. Nuclear and neuritic distribution of serine-129 phosphorylated a-synuclein in transgenic mice. Neuroscience, 2009; 160: 796-804.*
Wood SJ et al. Alpha-synuclein fibrillogenesis is nucleation-dependent. J Biol Chem. 1999; 274(28):19509-19512.*
Ko L-W et al. (2002) Cellular models for tau filament assembly. J. Mol. Neurosci. 19:311-316.*
Nonaka T et al. (2010) Seeded aggregation and toxicity of alpha-synuclein and tau: Cellular models of neurodegenerative diseases. J. Biol. Chem. 285(45):34885-34898.*
Paxinou E et al. (2001) Induction of alpha-synuclein aggregation by intracellular nitrative insult. J. Neurosci. 21(20):8053-8061.*
Zelphati O et al. (2001) Intracellular delivery of proteins with a new lipid-mediated delivery system. J. Biol. Chem. 276(37):35103-35110.*
Harper JD and Lansbury PT (1997) Models of amyloid seeding in Alzheimer's disease and scrapie: Mechanistic truths and physiological consequences of the time-dependent solubility of amyloid proteins. Annu. Rev. Biochem. 66:385-407.*
Soto C et al. (Mar. 2006) Amyloids, prions and the inherent infectious nature of misfolded protein aggregates. Trends Biochem. Sci. 31(3):150-156.*
Yang AJ et al. (1995) Intracellular A_1-42 aggregates stimulate the accumulation of stable, insoluble amyloidogenic fragments of the amyloid precursor protein in transfected cells. J. Biol. Chem. 270(24):14786-14792.*
Volles MJ et al. Zeroing in on the pathogenic form of alpha-synuclein and its mechanism of neurotoxicity in Parkinson's disease. Biochemistry, 2003, 42(26):7871-7878.*
Masliah E et al. Beta-amyloid peptides enhance alpha-synuclein accumulation and neuronal deficits in a transgenic mouse model linking Alzheimer's disease and Parkinson's disease. PNAS, 2001, 98(21):12245-12250.*

(Continued)

Primary Examiner — Kimberly A. Ballard
(74) Attorney, Agent, or Firm — Birch, Stewart, Kolasch & Birch, LLP

(57) ABSTRACT

The present invention has the object of providing a cell into which a protein, which can serve as a polymerization nucleus of a protein polymer, or polymer thereof is introduced, and a method for producing the cell. The invention relates to a cell into which a protein, which can serve as a polymerization nucleus of a protein polymer, or a polymer thereof is introduced, a method for producing the cell, and a method of screening for a compound inhibiting an intracellular accumulation of a protein containing fibril structures, wherein the method comprises bringing a candidate substance into contact with the cell.

4 Claims, 8 Drawing Sheets
(4 of 8 Drawing Sheet(s) Filed in Color)

(56) References Cited

OTHER PUBLICATIONS

Schmittschmitt JP et al. The role of protein stability, solubility, and net charge in amyloid fibril formation. Protein Sci. 2003, 12:2374-2378.*

Sells MA et al. Delivery of protein into cells using polycationic liposomes. Biotechniques, 1995, 19(1):72-76, 78.*

Stefanova et al., "Glial cell death induced by overexpression of alpha-synuclein," J. Neurosci. Res., (2001), vol. 65, No. 5, pp. 432-438.

Tabrizi et al., "Expression of mutant alpha-synuclein causes increased susceptibility to dopamine toxicity," Human Mol. Genet., (2000), vol. 9, No. 18, pp. 2683-2689.

Masuda et al., "Alpha-Synuclein Sen'ika Sogaizai no Tanasaku to Sogai Kiko," Nippon Chiho Gakkaishi, Aug. 15, 2005 (Aug. 15, 2005), vol. 19, No. 2, p. 168, III-C1.

Taniguchi et al., "Inhibition of heparin-induced tau filament formation by phenothiazines, polyphenols, and porphyrins," J. Biol. Chem., Mar. 4, 2005(Mar. 4, 2005), vol. 280, No. 9, pp. 7614-7623.

Jarrett et al., "Seeding "One Dimensional Crystallization" of Amyloid: A Pathogenic Mechanism in Alzheimer's Disease and Scrapie?", Cell, (1993) vol. 73, pp. 1055-1058.

Pandey, N., et al. "The alpha-synuclein mutation E46K promotes aggregation in cultured cells" Experimental Neurology, No. 197, 2006, pp. 515-520. XP-024945717.

Shimura, H., et al."CHIP-Hsc70 Complex Ubiquitinates Phosphorylated Tau and Enhances Cell Survival", The Journal of Biological Chemistry, vol. 279, No. 6, Feb. 2004, pp. 4869-4876. XP-002528433.

Kirby, J., et al., "Differential gene expression in a cell culture model of SOD1-related familial motor neurone disease" Human Molecular Genetics, vol. 11, No. 17, 2002, pp. 2061-2075. XP-002528432.

* cited by examiner

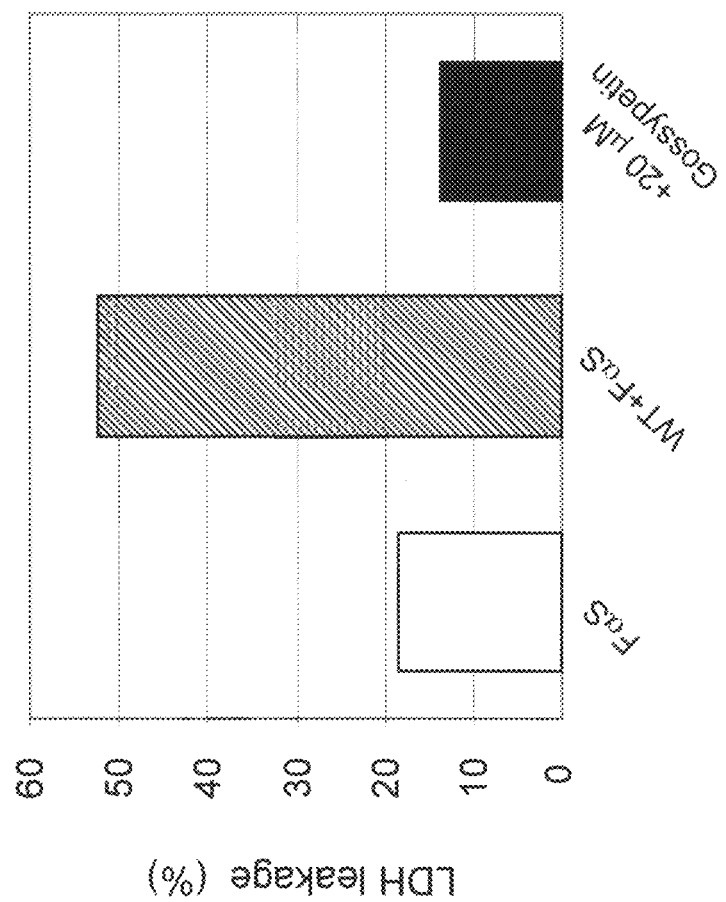

CELL INTO WHICH PROTEIN, WHICH CAN SERVE AS POLYMERIZATION NUCLEUS OF PROTEIN POLYMER, OR POLYMER THEREOF IS INTRODUCED, AND METHOD FOR PRODUCTION OF THE CELL

FIELD OF THE INVENTION

The present invention relates to a cell into which a protein, which can serve as a polymerization nucleus (seed) of a protein polymer, or a polymer thereof is introduced, a method for producing the cell, and a method of screening therapeutic agents for neurodegenerative diseases using the cell.

BACKGROUND OF THE INVENTION

Distinctive pathological structures are present in the neurons of the brains of patients suffering from neurodegenerative diseases such as Alzheimer's disease or Parkinson's disease. The pathological structures of Alzheimer's disease are termed neurofibrillary tangles and those of Parkinson's disease are termed Lewy bodies. Both types of pathological structures are composed of abnormal fibrils or filamentous deposits of proteins. Tau, one of the microtubule binding proteins, and α-synuclein have been identified as major constituents of neurofibrillary tangles and Lewy bodies, respectively. In particular, genetic analysis of familial cases of Parkinson's disease has demonstrated that the gene coding for α-synuclein is one of the responsible genes for Parkinson's disease. The observation that the number of abnormal inclusions and their regional distribution correlate with clinical symptoms in these neurodegenerative diseases has led to the postulation of a mechanism in which such abnormal structures causes cellular dysfunction and finally neuronal cell death. However this mechanism is yet to be proved by experiment.

Thus the intracellular accumulation of Tau and α-synuclein is thought to be closely related to the pathogenesis of neurodegenerative diseases. In order to prove this hypothesis, a number of researches have been performed around the world into developing a cellular model or experimental animal model to investigate the intracellular accumulation of these proteins. However at present, there have been few reports of models producing the characteristics, or characteristics similar to, the structures actually seen in the brains of patients.

Molecular reactions in which usually water-soluble proteins undergo polymerization to form insoluble aggregates or fibrils can be divided into two processes, the formation of a nucleus and processes involving fibril elongation around a nucleus. A nucleation-dependent protein polymerization model has become accepted in which the rate limiting step is the formation of the nucleus (Jarrett J T & Lansbury P T Jr, Cell 73: 1055-1058, 1993). It has been suggested to apply these processes to reactions related to fibril formation and aggregations of protein accumulating in the cell. Encouraging experimental results have been obtained in the laboratory. However methods for efficiently introducing a polymerization nucleus into a cell without causing cellular damage remain elusive and actual application to living cells or experimental animals has proven extremely difficult.

SUMMARY OF THE INVENTION

The present invention has the object of providing a cell into which a protein, which can serve as a polymerization nucleus (seed) of a protein polymer, or a polymer thereof is introduced, and a method for producing the cell.

As a result of active research into the above problem, the present inventors achieved this invention of introducing a polymerization nucleus such as α-synuclein fibrils into a neuron to obtain a cell acting as a cellular model for studying neurodegenerative diseases.

That is to say, the invention is as follows.

(1) A cell into which a protein, which can serve as a polymerization nucleus (seed) of a protein polymer, or a polymer thereof is introduced.

In the present invention, the protein can be exemplified by at least one selected from a group consisting of Tau protein, β-amyloid protein, α-synuclein, polyglutamine, SOD1, prion protein, and variants of these proteins. The cell is preferably a neuron or a glial cell. The cell of the present invention can be used as a cellular model for neurodegenerative diseases.

(2) A method for producing a cellular model for a neurodegenerative disease, wherein the method comprises introducing a protein, which can serve as a polymerization nucleus of a protein polymer, or a polymer thereof into a neuron or a glial cell. Furthermore the present invention provides a method for producing a cellular model for a neurodegenerative disease, wherein the method comprises introducing a protein, which can serve as a polymerization nucleus of a protein polymer, or a polymer thereof and a plasmid comprising a gene coding for the protein into a neuron or a glial cell, and causing interaction between the protein, which can serve as a polymerization nucleus, or the polymer thereof and a protein generated by expression of the plasmid to allow the protein polymer to accumulate in the cell.

(3) A method of screening a compound inhibiting an intracellular accumulation of a protein polymer, wherein the method comprises bringing a candidate substance into contact with the cell above.

(4) A method of screening a therapeutic agent for a neurodegenerative disease, wherein the method comprises bringing a candidate substance into contact with the cell above.

(5) A kit for screening a compound inhibiting an intracellular accumulation of a protein polymer or a therapeutic agent for a neurodegenerative disease, comprising the cell above.

BRIEF DESCRIPTION OF DRAWINGS

The patent or application file contains at least one drawing executed in color. Copies of this patent or patent application publication with color drawing(s) will be provided by the Office upon request and payment of the necessary fee.

FIG. 8 shows the suppressive effect of Gossypetin on the cell death.

DETAILED DESCRIPTION OF THE INVENTION

Figure 1:
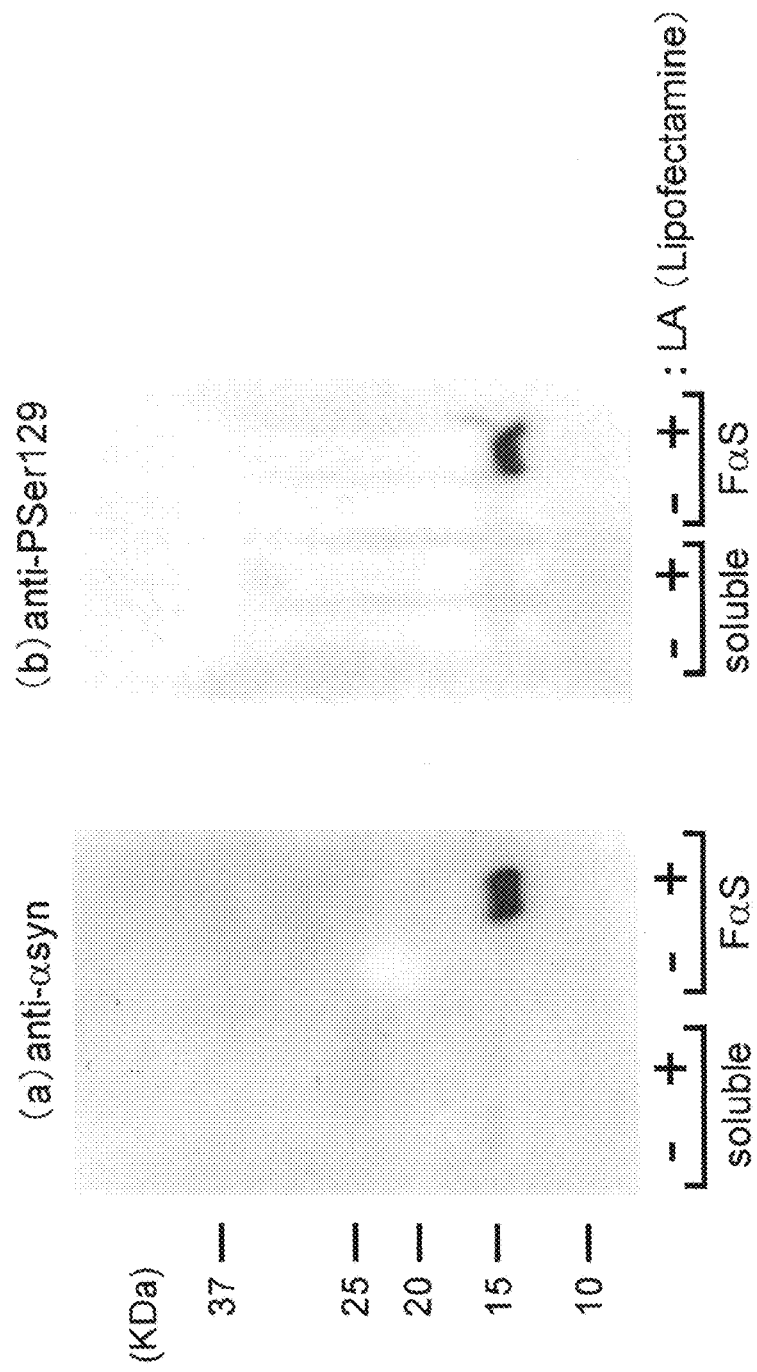
FIG. 1 shows immunoblots of lysates of neuroblastoma SH-SY5Y cells into which α-synuclein fibrils, α-synuclein polymer, which can serve as a polymerization nucleus, are introduced.

Hereinafter, the present invention will be described in detail. The following embodiments of the invention are examples for the purpose of describing the invention and are not for the purpose of limiting the invention to the form of the embodiments. The invention may be applied in various embodiments without departing from the spirit of the invention.

Publications cited in the present specification in addition to laid-open applications, published patents and other patent documents are incorporated by reference into the present specification. The present specification contains the contents of the specification of Japanese patent application (Japanese Patent Application No. 2005-352486) based on a claim to priority of the basic application filed Dec. 6, 2005.

The present invention relates to a cell in which structures accumulate as a result of the introduction of a protein which can serve as a polymerization nucleus of a protein polymer, or a polymer thereof, and to a method for producing the cell.

1. Overview

The present inventors have conducted experiments with the aim of producing a model allowing for simple analysis of fibrillization within the brain by efficiently introducing a polymerization nucleus into a cell without causing traumatic damages to the cell. Therefore attempts were made to introduce a protein which can serve as a polymerization nucleus of a protein polymer, or a polymer thereof, for example fibrillized proteins, into a cell.

Firstly the present inventors used the neuroblastoma SH-SY5Y cell line to construct a cellular model allowing intracellular accumulation of α-synuclein. The present inventors found that a protein polymer or a protein which can serve as the nucleus for polymerization, can be physically introduced into cells, and that protein or polymer thereof introduced into cells was phosphorylated and accumulated in the cells. Furthermore it was noted that the cells introduced displayed some of the pathological characteristics seen in the brains of patients.

Furthermore the present inventors achieved intracellular accumulation of a protein polymer by combination of introduction of a nucleus (polymerization seed) and over-expression of a protein which promotes elongation reactions for polymer formation by using recombinant technology to introduce a plasmid coding for the protein into a cell. Thereafter a protein which can serve as a polymerization nucleus of a protein polymer or a protein polymer thereof was introduced into the cell causing an interaction between the protein which can serve as a polymerization nucleus of a protein polymer, or a protein polymer thereof, and the protein produced by the plasmid. By using this method, the present inventors succeeded to produce protein aggregates extremely similar to those accumulated in the brains of patients in cultured cells. Furthermore, the cells that formed inclusions underwent cell death. The method of the present invention is extremely original and not seen in the prior art.

In the present invention, when the protein polymer formed in the cells is stained by anti-phosphorylated α-synuclein or anti-ubiquitin antibody, the polymer has a startling similarity to the Lewy bodies seen in the brains of patients. Furthermore it was found that, similar to the α-synuclein in Lewy bodies, the α-synuclein in the abnormal polymer formed in the cellular model is detergent-insolublet and accumulated within the cells. Surprisingly, cells produced in accordance with the above method underwent cell death with intracellular α-synuclein accumulates (see Examples). Thus, the new cellular model devised by the present inventors is a good model for accumulation of α-synuclein and related cell death in which α-synuclein is abnormally phosphorylated and deposited in filamentous aggregates as those found in Lewy bodies derived from the brains of patients. This model can be applied to the elucidation of the molecular mechanisms of neuronal death mediated by the accumulation of protein aggregates, or to the development of therapeutic agents such as research into pharmaceuticals which suppress such accumulation. Although the development of animal models such as mice is also important, the assay for use in cultured cells developed by the present invention is cheaper and simpler than animal models and is useful for high-throughput screening tests in a short time.

2. a Protein which can Serve as a Polymerization Nucleus of a Protein Polymer, or a Polymer Thereof A "protein polymer" as used herein means an insoluble protein structure or agent which is expressed or deposited outside or inside neurons or glial cells of the brain of patients suffering from neurodegenerative diseases. A "protein which can serve as a polymerization nucleus of a protein polymer, or a polymer thereof" includes fibril proteinaceous structures or a polymer thereof (hereafter termed "fibril structures or polymerization nucleus"). "Polymer" means a substance resulting from the polymerization or assembly of protein molecules and it also includes oligomers of the polymerization of several molecules. "Polymerization nucleus" means starting substance or seed in a molecular reaction forming amyloid filaments, insoluble fibrils or aggregates by the polymerization of soluble protein(s). For example, this includes amyloid fibrils fragmented or homogenized by sonication. Fibril structures or the polymerization nucleus can be composed of various types of proteins. Abnormal protein deposits and the fibril structures are pathological characteristics of many neurodegenerative diseases and their formation and processes are thought to be closely related to the pathogenesis of the disease. Alzheimer's disease is characterized by the deposition of intracellular neurofibrillary lesions consisting of hyperphosphorylated tau. In Parkinson's disease and Lewy body diseases, filamentous inclusions made of hyperphosphorylated α-synuclein are accumulated in degenerating neurons.

α-synuclein is a protein which accumulates in brains of patients with Parkinson's disease or Lewy body diseases. Several causative mutations have been identified in the familial cases of Parkinson's disease. Therefore, aggregation of α-synuclein is thought to play an important role in cell death of Parkinson's disease or Lewy body diseases.

Tau is a microtubule-associated protein, which accumulates as neurofibrillary tangles in neurons in Alzheimer's disease and other related diseases referred to as tauopathies. Although various types of abnormal structures or inclusions are observed in these tauopathies, the main constituent of these inclusions is tau. Similar to α-synuclein in Lewy bodies, tau is deposited in cells as a hyperphosphorylated and filamentous form which is highly detergents-insoluble.

Triplet repeat diseases such as Huntington's disease are examples of other neurodegenerative diseases in which proteins accumulate in nuclei or cytoplasms of neurons in a similar manner as Alzheimer's or Parkinson's disease. In Huntington's disease, polyglutamine-expanded huntingtin aggregations play a central role in the progress of the disease and cytotoxicity. Mutant huntingtin is present as insoluble intranuclear aggregates or as protein fragments containing soluble polyglutamine chains. The intranuclear localization of polyglutamine chains is an essential factor in cell death.

Amyotrophic lateral sclerosis is an example of another neurodegenerative disease in which deposits appear in neurons. In this disease, Cu/Zn superoxide dismutase (SOD1) accumulates. SOD1 is a protein thought to have cytotoxic properties. In amyotrophic lateral sclerosis, inclusion bodies similar to Lewy bodies are known to accumulate. The SOD1 aggregates itself play a central role in the degeneration of motor neurons.

Amyloid β protein (Aβ) is known as a protein which undergoes extracellular accumulation in Alzheimer's disease. Aβ is thought to interact, albeit weakly, with tau. Pathogenic mutations have been identified in the amyloid β protein precursor gene in familial forms of Alzheimer's disease and therefore the accumulation of Aβ is thought to participate in the pathogenesis of Alzheimer's disease. Since Aβ protein sometimes accumulates within the cell, it is included as a protein to be introduced into the cell.

Prion protein is known to undergo abnormal accumulation in relation to mad cow disease or Creutzfeldt-Jakob disease and displays extracellular or intracellular accumulation in a fibril form. Prion protein is thought to cause neuronal death as a result of the transformation of normal prion protein into pathological prion protein stemming from modification to the higher-order structure of prion protein causing an increase in the number of β-sheets.

All the above proteins or protein deposits are thought to be related each other, because all these diseases share a common pathological feature of intracellular or extracellular accumulation of abnormal proteins. Therefore, accumulation of these proteins and neurodegeneration may occur by a common mechanism. Thus the cellular model of the present invention may be useful for the above all neurodegenerative diseases.

The proteins used in the present invention are not limited to the proteins above and variants of the above proteins may be used. "Variant" means a protein resulting from a modification such as a deletion, addition or substitution of one or more (for example one to ten, preferably, one to five) amino acids and includes substances which undergo intracellular or extracellular accumulation as a protein polymer. For example analysis of familial Parkinson's disease clusters has lead to the discovery of α-synuclein variants such as mutant A30P, A53T, and E46K. A30P is a variant resulting from substitution of the 30$^{th}$ alanine (Ala) by proline (Pro) in the amino acid sequence of α-synuclein (SEQ ID No: 2). A53T is a variant resulting from substitution of the 53$^{rd}$ alanine (Ala) by threonine (Thr) in the amino acid sequence of α-synuclein (SEQ ID No: 2). E46K is a variant resulting from substitution of the 46$^{th}$ glutamine (Glu) by lysine (Lys) in the amino acid sequence of α-synuclein (SEQ ID No: 2).

α-synuclein fragments deleted in the N-terminal or C-terminal regions or α-synuclein lacking sequences repeats at 5-7 positions may be introduced into the cells of the present invention. Examples of fragments of α-synuclein are amino acid sequences of α-synuclein fragments as shown in SEQ ID No: 2 which are lacking amino acids at positions 131-140.

α-synuclein fragments lacking repeated sequences are the amino acid sequences of α-synuclein shown in SEQ ID No: 2 which are deleted in any or all of the amino acid residues at positions 10 to 15, 21 to 26, 32 to 37, 43 to 48 and 58 to 63.

3. Preparation of the Proteins or Polymers Thereof (1) Acquisition of the Genes Coding for the Proteins The proteins used in the present invention may be obtained using genes with the Accession numbers listed in Table 1 or the amino acid sequence data, or as a result of standard recombinant techniques using amino acid sequence data. These genes can be obtained from human cDNA libraries and genome libraries using DNA with the nucleic acid sequence shown by the SEQ ID Nos in Table 1, or fragments of such DNA as a probe in conjunction with known hybridization methods such as colony hybridization, plaque hybridization or southern blotting. Reference may be made to "Molecular Cloning, A Laboratory Manual 2$^{nd}$ ed." (Cold Spring Harbor Press (1989)) for these methods.

Genes coding for the above proteins may be produced using normal chemosynthetic methods or biochemical synthetic methods. For example, it is possible to use a recombinant method such as nucleic acid synthesis using a standard DNA synthesis apparatus, or a gene amplification method using PCR or a cloning vector after isolating or synthesizing the template nucleic acid sequence. Thereafter the resulting nucleic acid is cleaved using restriction enzymes. DNA fragments of the gene obtained as discussed above can then be inserted into an appropriate expression vector to create an expression vector including the gene coding for the protein.

Proteins or variants thereof can be isolated from foci of neurodegenerative diseases and sequenced using known recombinant methods, for example methods inducing site-directed mutagenesis such as the Kunkel method or Gapped duplex method. Kits for use in relation to inducing site-directed mutagenesis include QuikChange™ Site-Directed Mutagenesis Kit (Stratagene Pty Ltd), GeneTailor™ Site-Directed Mutagenesis System (Invitrogene Pty Ltd, TaKaRa Site-Directed Mutagenesis System (Mutan-K, Mutan-Super Express Km: TaKaRa Biotechnology).

The proteins as discussed above include α-synuclein, Tau, SOD1, polyglutamine, Aβ, prion protein, and variants thereof. Table 1 shows the amino acid sequences of these proteins together with the nucleic acid sequences of their corresponding genes.

TABLE 1

| Accession Number Protein (upper row) Gene (lower row) | Nucleic Acid Sequence of Gene | Amino Acid Sequence of Protein |
|---|---|---|
| α-synuclein | P37804 L08850 | SEQ ID No: 1 | SEQ ID No: 2 |
| Tau | NP005901 NM_005910.2 | SEQ ID No: 3 | SEQ ID No: 4 |
| SOD1 | NP000445 NM_000454.4 | SEQ ID No: 5 | SEQ ID No: 6 |
| Huntingtons polyglutamine | NP002102 NM_002111.5 | SEQ ID No: 7 | SEQ ID No: 8 |
| Aβ precursor protein | P5067 Y00264 | SEQ ID No: 9 | SEQ ID No: 10 |
| Prion | NP898902 NM_183079.1 | SEQ ID No: 11 | SEQ ID No: 12 |

In addition to the nucleic acid sequences corresponding to the SEQ ID Nos above, genes coding for the proteins include DNA coding for proteins which hybridize under stringent conditions with sequences complimentary to the above nucleic acid sequences and which display intracellular accumulation or aggregation. For example, hybridization may be carried out under stringent conditions of 1×SSC to 2×SSC, 0.1% to 0.5% SDS and 42° C. to 68° C. (degrees C.).

(2) Construction of Expression Vectors and Transformation

In the present invention, a protein which can serve as a polymerization nucleus can be obtained by constructing an expression vector as described hereafter, introducing the vector into a host which is then cultured. Alternatively, the protein may be purchased commercially.

There is no particular limitation on the host into which the expression vector is introduced and examples of the host include bacteria such as *Escherichia coli*, *Bacillus subtilis*, yeast such as *Saccharomyces cerevisiae*, COS cells, or mammalian cells. When using bacteria such as *Escherichia coli* as a host, it is preferred that the gene of the present invention is capable of autonomous replication in the host and at the same time that a structure such as a promoter or transcription stop sequence is included. Examples of expression vectors include pcDNA3, pRK172, pET and pGEX. Any promoter enabling expression of *Escherichia coli* in the host may be used. Examples of promoters from *Escherichia coli* or phages include trp promoter, lac promoter, PL promoter and PR promoter. Examples of an expression vector when using yeast as a host include YEp13 and YCp50. Examples of promoters include gall promoter or gall0 promoter. An example of a preferred expression vector, when using mammalian cells as a host, is pcDNA3.

Expression of the target gene is enabled by creating a transformant by introducing the expression vector into a host. There is no particular limitation on the host as long as the host allows expression of the target gene and examples include bacteria such as *Escherichia coli*, *Bacillus subtilis*, yeast such as *Saccharomyces cerevisiae*, COS cells, or mammalian cells such as CHO cells. Examples of methods of introducing the recombinant vectors into the host include electroporation, liposome methods, spheroplast methods or lithium acetate methods.

(3) Isolation and Purification of the Proteins or Polymers Thereof

Proteins are obtained by culturing the transformants above and harvesting the cultures. The "culture" means the culture supernatanta, culture cells, culture soma or any disrupted elements of cells or soma.

The method of culturing the transformant in the culture medium may be performed according to standard methods for culturing hosts.

A natural culture medium or a synthetic culture medium can be used as the culture medium used for culturing the transformant host such as *E. coli* or yeast as long as it contains sources of carbon, nitrogen and minerals which can be acquired by microorganisms for efficient culturing of the transformant.

Sources of carbon include carbohydrates such as glucose, fructose, sucrose or starch, organic acids such as acetic acid or propionic acid or types of alcohol such as ethanol and propanol.

Sources of nitrogen include organic or inorganic ammonium salts such as ammonia, ammonium chloride, ammonium sulfate, ammonium acetate, or ammonium phosphate, peptone, meat extract or corn steep liquor.

Minerals include monopotassium phosphate, dipotassium phosphate, magnesium phosphate, magnesium sulfate, sodium chloride, ferrous phosphate, manganese sulfate, cupric sulfate or calcium carbonate.

Aerobic conditions resulting from shake-culturing or aeration stir culturing for example, for 6-24 hours at 37° C. are applied during culturing. Regulation of the pH may be performed by using organic or inorganic acids or alkaline solutions.

Antibiotics such as ampicillin or penicillin may be added to the culture as required.

When culturing a microorganism transformed by an expression vector in which the promoter is an inducible promoter, an inducer may be added to the culture as required. For example, when culturing a microorganism transformed using an expression vector comprising the Lac promoter, isopropyl-1-thio-β-D-thiogalactoside (IPTG) may be added as required.

The culture medium for culturing a transformant using an animal cell as a host may be a standard RPMI-1640 culture medium, a DMEM culture medium or a culture medium comprising one of these mediums with the addition of fetal calf serum.

Culturing is normally performed at 37° C. for between 1 to 30 days at 5% $CO_2$. During culturing, the culture may be supplemented by antibiotics such as ampicillin or penicillin as required.

After culturing, protein produced in the soma or the cell is extracted by rupturing the soma or cell. Furthermore when protein or a polymer thereof comprising a fibril structure has been produced in the soma or cell, the culture solution may be used or the cells or soma may be removed by centrifugal separation. Thereafter the protein may be isolated from the culture and purified using standard biochemical methods for isolating and purifying protein such as ammonium sulfate precipitation, gel chromatography, ion-exchange chromatography or affinity chromatography. Such methods may be used singly or in combination.

The polymerization and fibril formation of a protein, for example, can be performed by shaking a purified protein solution or a crude solution containing the protein. The aggregates or structures obtained as a result of the polymerization are recovered by ultracentrifugation, suspended in an appropriate amount of buffer and used as the proteins or polymers thereof for introduction into cells.

In the present invention, it is possible to use proteins produced by a cell-free protein synthesis system without using living cells. A cell-free protein synthesis system is system synthesizing protein from a cellular extract in an artificial vessel such as a test tube. A cell-free transcription system synthesizing RNA from template DNA is contained in a cell-free protein synthesis system. The above liquid cell extract may be a liquid extract from eukaryotic cells or prokaryotic cells and may contain for example liquid extracts of wheat germ, rabbit reticular cell, mouse L cells, He-La cells, CHO cells, budding yeast, *E. coli* etc.

Furthermore in the present invention, free cell protein synthesis can be performed using commercial kits. Such kits include PURESYSTEM (Post Genome Institute Co. Ltd.), PROTEIOS™ (Toyobo) and TNT™ System (Promega).

Proteins obtained using the above cell-free protein synthesis can be purified by selecting suitable methods of chromatography as discussed above.

4. Introduction into Cells of a Protein which can Serve as a Polymerization Nucleus of a Protein Polymer, or a Polymer Thereof In this invention, it is possible to create cells containing an accumulation of protein polymers by introducing into cells a protein, which can serve as a polymerization nucleus of a protein polymer, or a polymer thereof, such as a fibril structure as described above. There is no particular limitation on the types of cells used in the present invention, however animal cells are preferred, and neurons or glial cells are further preferred. For example, such cells include neuroblastoma SH-SY5Y cells (L. Odelstad at al., 1981, Brain Res., 224: 69-82), NIH/3T3 cells, or glia-type cells such as OLN-93 cells. However the present invention is not limited in this regard.

The introduction into cells of a protein which can serve as a polymerization nucleus of a protein polymer, or a polymer thereof may be performed using a suitable induction reagent. Reagents for introducing the substance into the cell include LIPOFECTAMINE™ or CHARIOT™. When introducing into a cell a protein which can serve as a polymerization nucleus of a protein polymer or a protein polymer thereof, ultrasonication may be used as required for fragmentation.

The type of the protein polymer determines whether or not the location of protein polymer accumulation is intracellular, extracellular or both. For example, α-synuclein undergoes intracellular accumulation, but Aβ and prion protein undergo both intracellular and extracellular accumulation.

In the present invention, the introduced polymerization nucleus is phosphorylated, accumulates and cells with the polymerization nucleus introduced therein display some of the pathological characteristics observed in the brains of patients.

In the present invention, over-expression of a protein thought to be necessary for elongation reactions can be achieved by introducing the gene coding for the protein into a cell. At the same time, a protein which can serve as a polymerization nucleus of a protein polymer, or a protein polymer thereof, is introduced into the cell. In this manner, a protein polymer accumulates in the cell as a result of an interaction between the introduced polymerization nucleus and the over-expressed protein. However the introduction of the gene coding for the protein promoting the elongation step of polymerization may be performed at the same time as the introduction into the cell of a protein which can serve as a polymerization nucleus of a protein polymer, or a protein polymer thereof, or either can be introduced before the other. There is no limitation on the sequence or timing of the introduction.

The cells produced by above methods are preferred as a cellular model which more closely mimics the brains of patients, since it is observed that protein which is extremely similar to protein actually accumulating in the brains of patients aggregates and accumulates in cells produced in the above manner and that the cells progress to cell death. The methods for intracellular expression of the protein thought to be required for elongation reactions associated with polymer formation includes the preparation of a suitable recombinant vector containing a gene coding for the protein, the introduction of the recombinant vector into a neuron or glial cell and the culturing of the cells for an appropriate period of time. The preparation of a recombinant plasmid and transformant may be performed in accordance with the methods disclosed in the section 3 above.

The introduction of the protein into cells may be confirmed by immunoblot analysis employing antibodies raised against the protein. The intracellular accumulation of protein may be also confirmed using a confocal laser microscope and immunocytochemical staining.

It is known that Lewy bodies observed in the brains of patients contain ubiquitinated α-synuclein in addition to phosphorylated α-synuclein. The intracellular structures expressed in the α-synuclein accumulating cellular model of the present invention not only resemble the shape and size of Lewy bodies and are composed of phosphorylated α-synuclein, and partially ubiquinated. This fact may be confirmed for example by double staining the above cells and vibratome fragments from patients brains suffering from dementia with Lewy bodies (DLB) with anti-α-synuclein antibodies and ubiquitin antibodies. The cells are observed using a confocal laser microscope. In this manner, it is observed that the protein polymer is ubiquitinated in the same manner as Lewy bodies.

5. A Cellular Model for Accumulation of Protein Aggregates

Figure 6:
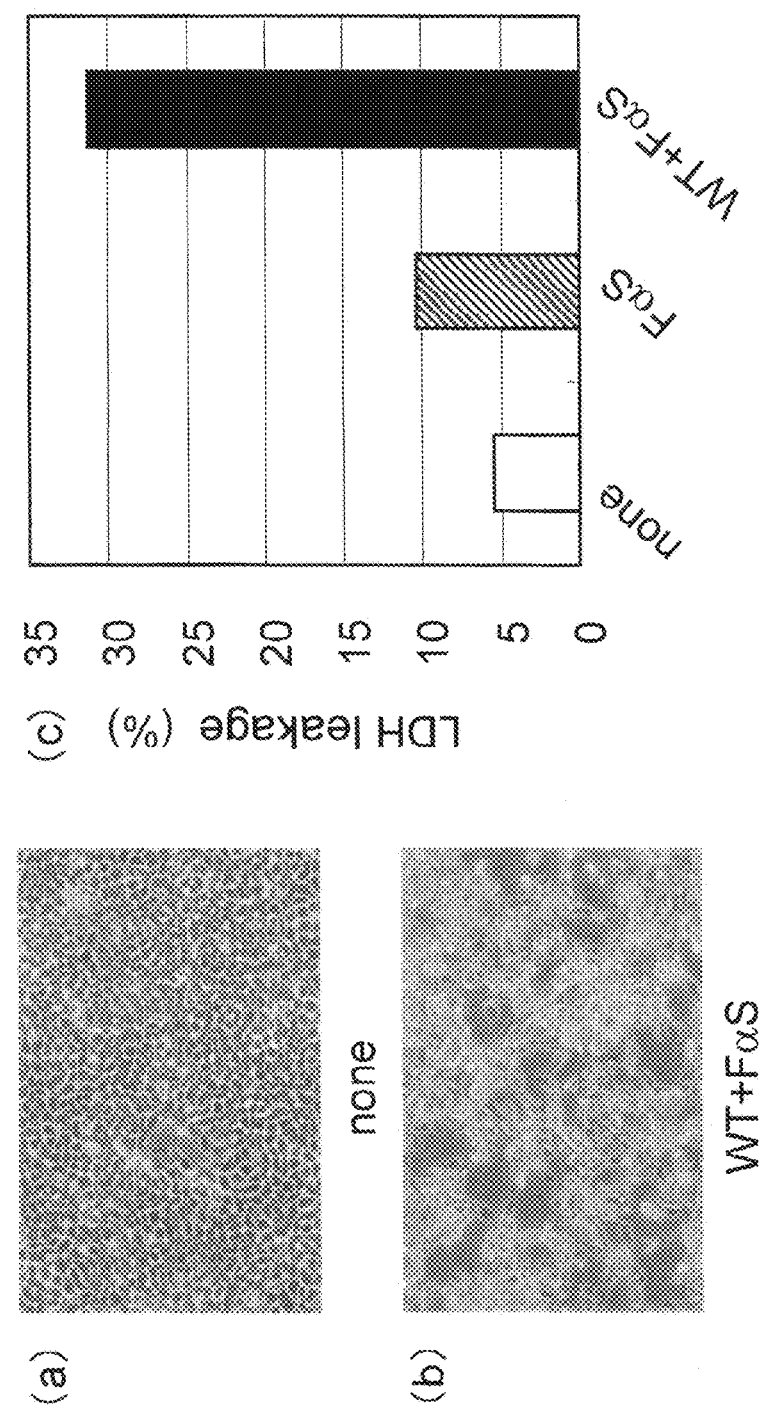
FIG. 6 shows a morphological change and a cell death in cells into which α-synuclein plasmid DNA and fibrils are introduced.

A cellular model in which protein polymer accumulates as in the present invention undergoes cell death. It is clearly observed that the morphologies of the above cells introduced protein polymer are changed after culturing for a fixed period of time by comparing with control cells into which the protein polymer has not been introduced (FIG. 6-*b*). Furthermore a clear decrease in the number of cells is also noted. Thus the cells according to the present invention can be used as a model for neurodegenerative diseases.

A cell death assay may be used to confirm that cell death has been induced in the cellular model for neurodegenerative diseases according to the present invention. There is no particular limitation on the cell death assay and for example a lactate dehydrogenase (LDH) leakage assay may be used. This assay method is based on determining how much LDH originally inside the cells has leaked outside the cells as a result of cell death. Higher extracellular activity of LDH demonstrates more extensive cell death.

6. Screening Methods and Kits

The screening methods according to the present invention are characterized by bringing a candidate reagent or reagents into contact with cells into which a protein polymer or polymers has been introduced. In this manner, it is possible to screen for substances which inhibit the intracellular accumulation of protein polymer. Furthermore it is possible to screen neurodegenerative disease therapeutic agents.

A neurodegenerative disease means a disease comprising phenomena such as neurodegeneration in which neurons die in the absence of a clear cause such as external damage or bacterial infection. Such diseases include for example Alzheimer's disease which is a major cause of dementia and Parkinson's disease which is associated principally with dyskinesia. However in addition to these two diseases, neurodegenerative diseases include Huntington's disease, triplet repeat diseases, amyotrophic lateral sclerosis, dementia with Lewy bodies, multiple system atrophy, Creutzfeldt-Jakob disease, Gerstmann-Straussler syndrome, mad cow disease, spinobulbar muscular atrophy, spinocerebellar ataxia, dentatorubral-pallidoluysian atrophy, FDTP-17, progressive supranuclear palsy, corticobasal degeneration and Pick's disease.

"Contact" means that the cells into which the protein polymer has been introduced are present in the same reaction system or culturing system as the candidate substance (test substance) and includes for example culturing the cells in the presence of the candidate substance by adding the candidate substance to the cell culturing vessel and mixing the cells with the candidate substance.

In a preferred embodiment of the present invention, when studying neurodegenerative diseases such as Parkinson's disease, dementia with Lewy bodies, and multiple system atrophy, it is preferred to use cells into which α-synuclein has been introduced as a fibril structure. The candidate substance is brought into contact with the neuron containing an accumulation of α-synuclein. Cells brought into contact with the candidate substance are compared and contrasted with respect to a character or an index having a correlation with the target disease. Thus it is possible to screen substances inhibiting the intracellular accumulation of α-synuclein or substances which reduce or eliminate symptoms of Parkinson's disease. Examples of a character or an index having a correlation with the target disease are described hereafter. A character or an index having a correlation with the target disease may be used singly or in combination with two or more other characters or indexes.

Parkinson's disease: the presence or absence of α-synuclein accumulation, the presence or absence of Lewy bodies, the presence or absence of reactivity to anti-ubiquitin antibodies, the presence or absence of changes to neurons.

Alzheimer's disease: the presence or absence of Aβ or tau accumulations, the presence or absence of neuronal fibrillogenesis, the presence or absence of reactivity to anti-ubiquitin antibodies, the presence or absence of changes to neurons.

Creutzfeldt-Jakob disease: the presence or absence of prion accumulation, the presence or absence of changes to neurons.

Huntington's disease: the presence or absence of Huntingtin accumulation, the presence or absence of changes to neurons.

When screening candidate substances for a neurodegenerative disease such as Alzheimer's, that is to say, when screening compounds as therapeutic agents for use against Alzheimer's disease, it is preferred to use neurons into which Aβ or tau has been introduced. When examining Creutzfeldt-Jakob disease, Gerstmann-Straussler syndrome and mad-cow disease, it is preferred to use cells into which prion protein has been introduced. When examining neurodegenerative diseases such as Huntington's disease, spinobulbar muscular atrophy, spinocerebellar ataxia, dentatorubral-pallidoluysian atrophy, it is preferred to use cells into which polyglutamine protein has been introduced. When the neurodegenerative disease is amyotrophic lateral sclerosis, it is preferred to use cells into which SOD1 has been introduced. When the neurodegenerative disease is FDTP-17, progressive supranuclear palsy, corticobasal degeneration or Pick's disease, it is preferred to use cells into which tau has been introduced.

Candidate reagents include peptides, proteins, non-peptide compounds, synthetic compounds (macromolecules or low-molecular weight compounds), fermentation products, liquid cell extracts, supernatant of cellular cultures, liquid plant extracts, mammalian liquid tissue extracts (for example, mouse, rat, pig, cow, sheep, monkey, human, etc), and plasma. These compounds may be novel compounds or known compounds. The candidate compounds may be in the form of a salt, and salts of candidate substances may be used as physiologically permissible acids (for example, inorganic acids, or organic acids) or bases (for example metallic acids).

Cells containing intracellular accumulations of fibril structures, a protein, which can serve as a polymerization nucleus of a protein polymer, or a polymer thereof, progress to cell death. Consequently a candidate substance may be selected as a neurodegenerative disease therapeutic agent when it is confirmed that the incidence of cell death in cells to which the candidate substance has been administered is reduced or eliminated.

Gossypetin, a polyphenol compound may be taken as an example of a candidate substance. Gossypetin is a flavonol contained in *Gossypium herbaceum* LINNE and is polyphenol compound used as a food additive. For example, it is possible to investigate whether Gossypetin inhibits fibrillization of α-synuclein in vitro by incubating α-synuclein in the presence of Gossypetin, adding thioflavin S to the solution after the reaction and measuring the fluorescence intensity. Thioflavin S is a test reagent which emits fluorescence upon binding to a protein which can serve as a polymerization nucleus of a protein polymer, or a protein polymer thereof, which are rich in β-sheet structure and which therefore can be used to determine the presence or absence of a protein which can serve as a polymerization nucleus of a protein polymer, or a protein polymer thereof. In contrast, since α-synuclein fibrils are rich in β-sheet structure, if Gossypetin inhibits fibrillization of α-synuclein, the fluorescence intensity should be lower than samples to which Gossypetin has not been added.

This method demonstrates that Gossypetin inhibits fibrillization of α-synuclein in vitro. Consequently it can be stated that Gossypetin which is a polyphenol compound has a protective effect on cell death.

A cell according to the present invention may be provided in the form of a kit for screening compounds (substances) inhibiting the intracellular accumulation of protein polymers or therapeutic agents for neurodegenerative diseases. In addition to the above cell, a kit according to the present invention may contain marker substances, reagents for testing cell death (for example, LDH) and antibodies to phosphorylated α-synuclein etc. Marker substances mean enzymes, radioactive isotopes, fluorescent compounds and synthetic luminescent compounds. In addition to the above items, a kit according to the present invention may contain other reagents required for the methods of the present invention. For example when the marker substances are enzymes, the kit may include enzyme-substrate complexes (chromogenic substrates), enzyme-substrate solutions, enzyme reaction stop baths etc. Furthermore a kit according to the present invention may contain diluents for test compounds, various types of buffer, sterile water, various types of cell culturing vessels, various types of reaction containers (Eppendorf tubes), washing agents, experiment manuals (explanatory materials) etc.

EXAMPLES

Hereinafter, the present invention will be described in more detail with reference to working examples. However the present invention, however, is not limited to the examples described below.

1. Method

Preparation of α-Synuclein Fibrils

A pRK172 vector containing the α-synuclein gene was used according to the publication (Jakes R, Spillantini M G & Goegert M. FEBS Lett. 1994, 345: 27-32).

The vector was transformed into *E. coli* (strain BL21DE3) and the transformed *E. coli* were grown in 500 mL of LB culture medium containing 50 μg/mL ampicillin using shake-culturing for 6 hours at 37° C. 0.2 mM of isopropyl 1-thio-β-D-galactoside was added and the mixture was cultured for an additional two hours. Bacterial cells were recovered and quick-frozen in liquid nitrogen. After thawing at ambient temperature, the cells were suspended in 5 mL of Buffer A (50 mM Tris-HCl buffer, pH7.5/1 mM ethylene glycole bis(β-aminoethyl ether)-tetraacetic acid (EGTA)/1 mM dithiothreitol) and disrupted using sonication.

The cellular homogenate was centrifuged (26,600 g, 15 minutes, 4° C.), the supernatant recovered and heat treatment was applied for 5 minutes. Further centrifugation (26,600 g, 15 minutes, 4° C.) was applied to remove insoluble protein and the supernatant was applied onto Q-Sepharose (2 mL) column chromatography, pre-equilibrated with Buffer A. The column was washed with 6 mL of buffer A containing 0.1M NaCl. Protein bound to the column was eluted with 6 mL of Buffer A containing 0.5M NaCl. α-synuclein protein was precipitated by adding ammonium sulfate brought up to 50% saturation.

After centrifugation (39,100 g, 20 minutes, 4° C.), pelleted α-synuclein was dissolved in 1 mL of 50 mM Tris-HCl buffer, pH 7.5 (Buffer B) and dialyzed against 1 L of Buffer B. After determining the protein concentration, the dialysis sample was used for fibrillization. 5 to 10 mg/mL of α-synuclein was incubated with shaking for 4 days at 37° C. to induce fibrillization. After ultracentrifugation (113,000 g, 20 min, room temperature), the precipitated fibrils were suspended in an appropriate amount of Buffer B and sonicated. The protein concentration was determined and the resulting substance was used as the α-synuclein fibril or α-synuclein polymer acting as a polymerization nucleus for introduction into cells.

Preparation of the Cellular Model of α-Synuclein Proteinopathy

Neuroblastoma SH-SY5Y cells were cultured in an incubator at 37 degrees, 5% $CO_2$ using DMEM/F12 culture medium supplemented with 10% fetal calf serum.

The SH-SY5Y cells were cultured on 6 well plates to achieve 30-50% confluence. A mixture of 1 μg of a pcDNA vector containing the wild-type α-synuclein (pcDNA3-α-syn) and 3 μL of FUGENE™ 6 (Roche) mixed with 100 μL of opti-MEM (Lifetech Oriental Inc) was added to the culture medium and allowed to stand overnight in order to express soluble α-synuclein from the plasmid. In addition to the wild-type α-synuclein, pcDNA3 vectors were used which encoded a mutant α-synuclein (A30P, A53T, E46K) discovered in cases with familial Parkinson disease, truncated α-synuclein with a deletion in the N-terminal or the C-terminal regions, and α-synuclein deletion in repeated sequences. In addition to using FUGENE™ 6, the transformation of the plasmid DNA was also performed in the same way using LIPOFECTAMINE™ Reagent (Invitrogene) and LIPOFECTAMINE™ 2000 (Invitrogene).

After allowing the cells to stand overnight, the cells were washed once using phosphate buffered saline (PBS) and the media exchanged with 1 mL of opti-MEM. A mixture of 2 μg of sonicated α-synuclein fibrils and 5 μL of LIPOFECTAMINE™ reagent mixed in 200 μL of opti-MEM was added to the cells and allowed to stand for three hours at 37° C. Thereafter the media was exchanged for normal DMEM/F12 media and culturing was continued in an incubator. As required, instead of the wild-type α-synuclein, the mutant α-synuclein (A30P, A53T, E46K), fragmented α-synuclein with a deletion in the N-terminal or C-terminal regions or α-synuclein deleted in repeated sequences were used. The method of fibrillizing these types of synuclein is the same as that applied to the wild-type α-synuclein.

Inhibition of Fibrillization of α-Synuclein In Vitro

The prepared recombinant α-synuclein was diluted in 30 mM Tris-HCl (pH 7.5), 0.2% $NaN_3$ to a concentration of 2 mg/mL and Gossypetin added to make a final concentration of 200 μM. Samples were incubated by shaking at 200 rpm at 37° C. After fibrillizing reactions, 300 mL of 5 μM thioflavin S solution (Sigma-Aldrich) [0.2% thioflavin S, 20 mM MOPS (pH6.8)] was added to a 10 μL sample and incubated for 30 minutes at room temperature. Fluorescence intensity was measured using a Hitachi F4000 spectrophotometer (excitation wavelength 440 nm, fluorescence wavelength 520 nm).

Method of Evaluation of the Cellular Model of α-Synuclein Proteinopathy (1) Immunoblot Analysis of Gradual Protein Extraction Using Surface-Active Agent Cells were prepared by using Lipofectamine to introduce α-synuclein fibrils (wild-type, mutant etc) into SH-SY5Y cells which had been transfected with pcDNA3 plasmid containing for example wild-type α-synuclein. The cells were then incubated for a day. After discarding the media from the well, 0.5 mL of 0.25% trypsin solution was added and heated at 37° C. for 10 minutes. Then 0.5 mL of PBS was added and the cells removed and harvested by pipetting. The cells were recovered by centrifugation (1,800 g, 5 minutes, 4° C.), washed using 1 mL of PBS and centrifuged again at the same settings.

The cells were suspended in 100 μL of homogenizing buffer (50 mM Tris-HCl, pH 7.5/0.15 M NaCl/5 mM EGTA/protease inhibitor cocktail) and sonicated. The homogenates was ultra-centrifuged (290,000 g, 20 min, 4° C.) and the resulting supernatant was recovered as Tris-soluble fractions. Protein concentration of Tris soluble fractions was determined using a BCA Protein assay kit (Peirce) and prepared for SDS-PAGE by adding a sample buffer for sodium dodecylsulphate (SDS) polyacrylamide gel electrophoresis (SDS-PAGE).

The precipitated fraction was re-dissolved in 100 μL of homogenizing buffer containing 1% Triton X-100 (TX), sonicated and then ultracentrifuged again under the same conditions (290,000 g, 20 min, 4° C.). The resulting supernatant was collected as the TX soluble fraction, added to SDS sample buffer and used as a sample for electrophoresis. The precipitated fraction from TX processing was sonicated in 100 μL homogenizing buffer containing 1% Sarcosyl (Sar) and then incubated for 30 minutes at 37° C. After incubation, ultracentrifugation was performed (290,000 g, 20 min, 4° C.). The resulting supernatant was collected as the Sar soluble fraction. The pellet was added to 100 μL of SDS sample buffer, sonicated and used as a sample in electrophoresis.

All fractions were analyzed using Tris/Tricine SDS-PAGE using 13.5% gel. After completion of electrophoresis, the gel was transferred to a polyvinylidene fluoride [PVDF] membrane, blocked with gelatin solution and left overnight at room temperature to react with anti-α-synuclein antibody (anti-α-syn) or anti-phosphorylated α-synuclein antibody (anti-PSer129) at a dilution of 1:1000. After the reaction, the PVDF membrane was washed in Tris-buffered saline (TBS) and reacted with biotinylated mouse IgG at a dilution of 1:500 at room temperature for one hour. After the reaction, the membrane was washed in TBS and treated with IMMUNOSTAR™ (Wako Pure Chemicals) and sensitized in x-ray film (Fuji Film) in order to detect the bands.

(2) Observation by Confocal Laser Microscope

SH-SY5Y cells were cultured on cover glass. After pcDNA3-α-syn was transfected and cultured overnight according to a standard protocol, α-synuclein fibrils were introduced. After introduction, the cells were incubated for a number of days (1-2 days) and then fixed using 1 mL of 4% paraformaldehyde. The fixed cells were treated with 0.2% TX blocked with 5% bovine serum albumin/PBS and reacted for one hour at 37° C. with anti-PSer129 (diluted 1000 times).

After the cells were washed in TBS containing 0.5% Tween 20 (TBS-T), they were incubated for one hour at 37° C. with FITC-labeled anti-mouse antibody. Then in the same manner, after washing with TBS-T, the cells were reacted with TO-PRO-3 (diluted 1000 times) for nuclear staining. The cells were also reacted for 5 minutes at room temperature with 0.05% thioflavin S. After mounting these cells on a slide glass, they were observed using a confocal laser microscope (Zeiss).

(3) Cell Death Assay

A cell death assay was performed using cells into which pcDNA3-α-syn vector and α-synuclein fibrils are introduced, and which had been incubated for three days either in the presence or the absence of a fibrillization inhibitor. Gossypetin (20 μM) which is a type of polyphenol was used as the fibrillization inhibitor.

After incubation for three days, a portion of the cell media in the culture was harvested. The cells from the remaining media were prepared as a Tris-soluble fraction in the same manner as the Tris-soluble fraction described above. A cell death assay was performed on the harvested media and the Tris-soluble fraction using a CYTOTOX 96™ Non-Radioactive Cytotoxicity Assay Kit (Promega). The method was performed in accordance with the explanatory material accompanying the kit.

2. Results

The Introduction of α-Synuclein Polymer into Cells

In this section, it is examined as to whether or not α-synuclein polymer (fibrils) was introduced into the SH-SY5Y neuroblastoma cells. Sonicated α-synuclein fibrils (FαS) (2 μg) and non-fibrillized soluble α-synuclein (2 μg) were mixed with Lipofectamine reagent and SH-SY5Y cells. After allowing the mixture to react overnight, the cells were harvested and analyzed by immunoblot.

The results are shown in FIG. 1. The immunoblot results are respectively shown in FIG. 1(a) using antibodies (anti-α-syn) recognizing α-synuclein without reference to phosphorylation and FIG. 1(b) using antibodies (anti-PSer129) which specifically only recognize phosphorylated α-synuclein. Even though soluble α-synuclein treated using LIPOFECTAMINE™ was added to the cells, no band at all was visible (the "+" lane in "soluble" in FIG. 1). In contrast, when α-synuclein fibrils were added to the cells in the presence of LIPOFECTAMINE™ (the "+" lane of (FαS)), a band was detected with both antibodies. These results show that α-synuclein fibrils or α-synuclein polymer which can serve as a polymerization nucleus were introduced into the cells by the action of LIPOFECTAMINE™ and the introduced α-synuclein fibrils were phosphorylated. LIPOFECTAMINE™ incorporated the α-syn fibrils but not soluble α-syn into cells. Fibrils of the mutant α-synuclein (A30P, A53T, E46K), truncated α-synuclein lacking the N-terminal or the C-terminal region, and α-synuclein lacking the repeat sequence were introduced into the cells by the action of the LIPOFECTAMINE™ reagent in the same manner as the full-length of wild-type α-synuclein fibrils.

Production of the Cellular Model of α-Synuclein Proteinopathy

Figure 2:
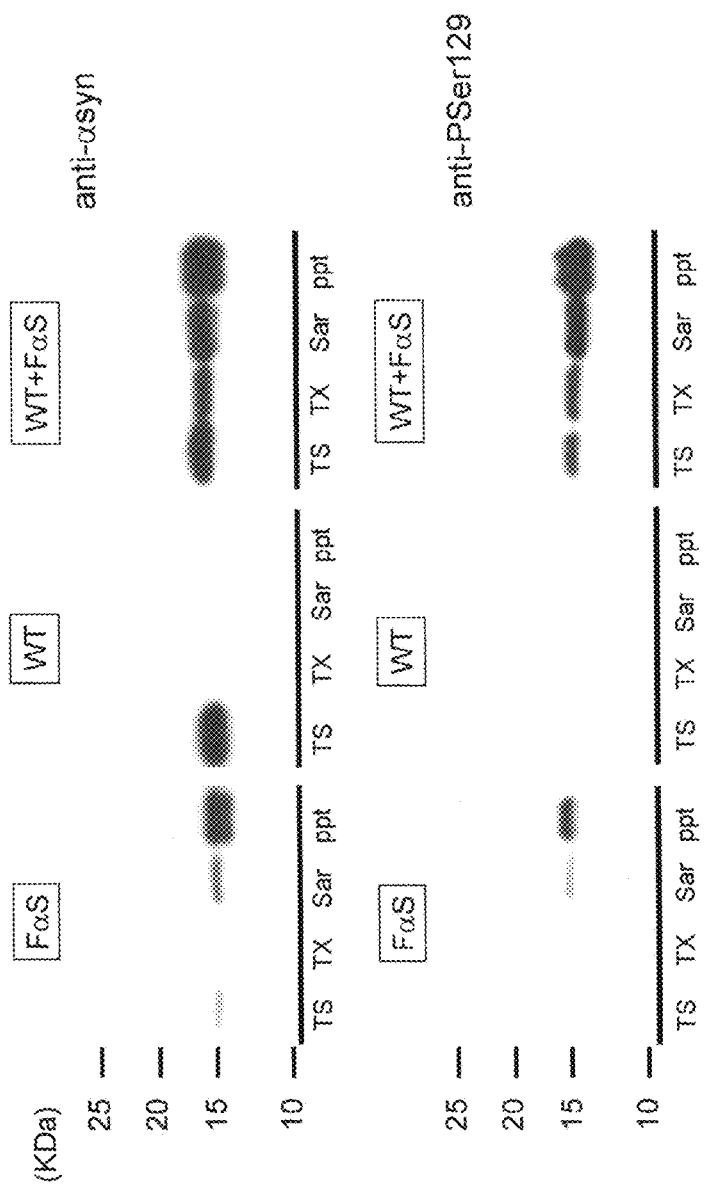
FIG. 2 shows accumulations of α-synuclein in cells into which α-synuclein fibrils, α-synuclein polymer, which can serve as a polymerization nucleus, are introduced and in which soluble α-synuclein is expressed.

In this section, it is investigated whether or not intracellular accumulation of α-synuclein occurs when α-synuclein polymer (fibrils) is introduced into cells overexpressing soluble α-synuclein. Three types of cells: cells only into which α-synuclein fibril (FαS) is introduced, cells transfected with pcDNA3 vector (pcDNA3-αsyn) containing the α-synuclein gene (WT) and cells into which α-synuclein fibril was introduced after transfection with pcDNA3-αsyn (WT+FαS) were prepared and α-synuclein from each type of cells were examined. The cells were treated with trypsin, washed in PBS, suspended in homogenizing buffer and sonicated. Protein was sequentially solubilized using Triton X-100 and Sarcosyl according to the methods described above in the Methods section. Each fraction was analyzed by immunoblotting using anti-α-syn and anti-PSer129. The results are shown in FIG. 2.

In the analysis of FαS cells into which only fibril has been introduced, there were many anti-α-syn antibody positive bands for the fraction (ppt fraction) which is insoluble in the detergent, and some of the bands had phosphorylated. In other words, these results show that the α-synuclein fibrils was introduced into the cells and got phosphorylated in cells. It also suggests that fibrils or α-synuclein polymer which can serve as a polymerization nucleus and which is introduced into the cells retain its insolubility while in the cell and is not excreted or degraded. Almost all the α-synuclein from cells expressing pcDNA3-αsyn (WT) was recovered in the soluble fraction (TS fraction). This shows that even when large amounts of α-synuclein is synthesized in the cell, it exists in a soluble state under normal conditions and does not easily undergo fibrillization or become insoluble. The results also show that almost no phosphorylation occurred.

On the other hand, anti-α-syn immunoreactivities were detected in all fractions of the WT+FαS cells transfected with α-synuclein plasmid DNA and fibrils. In particular, a dramatic increase of α-synuclein was observed in the ppt fraction and the insoluble α-synuclein was phosphorylated. In other words, intracellular α-synuclein overexpressed in WT+FαS cells become insoluble and recovered in the ppt fraction. The amount of phosphorylated α-synuclein in the ppt fraction from WT+FαS cells shows a large increase in comparison to the amount of phosphorylated α-synuclein from the cells transfected with FαS. These results indicate that overexpressed soluble α-synuclein by transfection with the plasmid polymerizes and accumulates in cells nucleation-dependently when α-synuclein fibrils (in other words, the introduced fibril acts as a nucleus) were introduced.

α-synuclein in the brains of patients is also known to be deposited in Lewy bodies in a hyperphosphorylated form. α-synuclein accumulating in the brains of patients is also recovered in detergent-insoluble fractions. This fact shows that α-synuclein accumulating in this cellular model displays biochemical properties similar to the α-synuclein accumulating in the brains of patients.

Immunohistochemical Observation of the Cellular Model of α-Synuclein Proteinopathy Since the α-synuclein accumulating in cells transfected with both α-synuclein plasmid DNA and the fibrils displays biochemical properties which are similar to α-synuclein existing in Lewy bodies from the brains of patients, in this section, an immunohistochemical examination and a morphological comparison with Lewy bodies was performed on cells with accumulation of α-synuclein. Immunocytochemical staining was performed on four types of cells: untreated cells (none), cells transfected with α-synuclein plasmid (WT), FαS cells transfected with α-synuclein fibrils, and WT+FαS cells transfected with both α-synuclein fibrils and plasmid. Staining was performed using anti-PSer129 antibodies specifically recognizing only phosphorylated α-synuclein. The cells were then observed using a confocal laser microscope.

Figure 3:
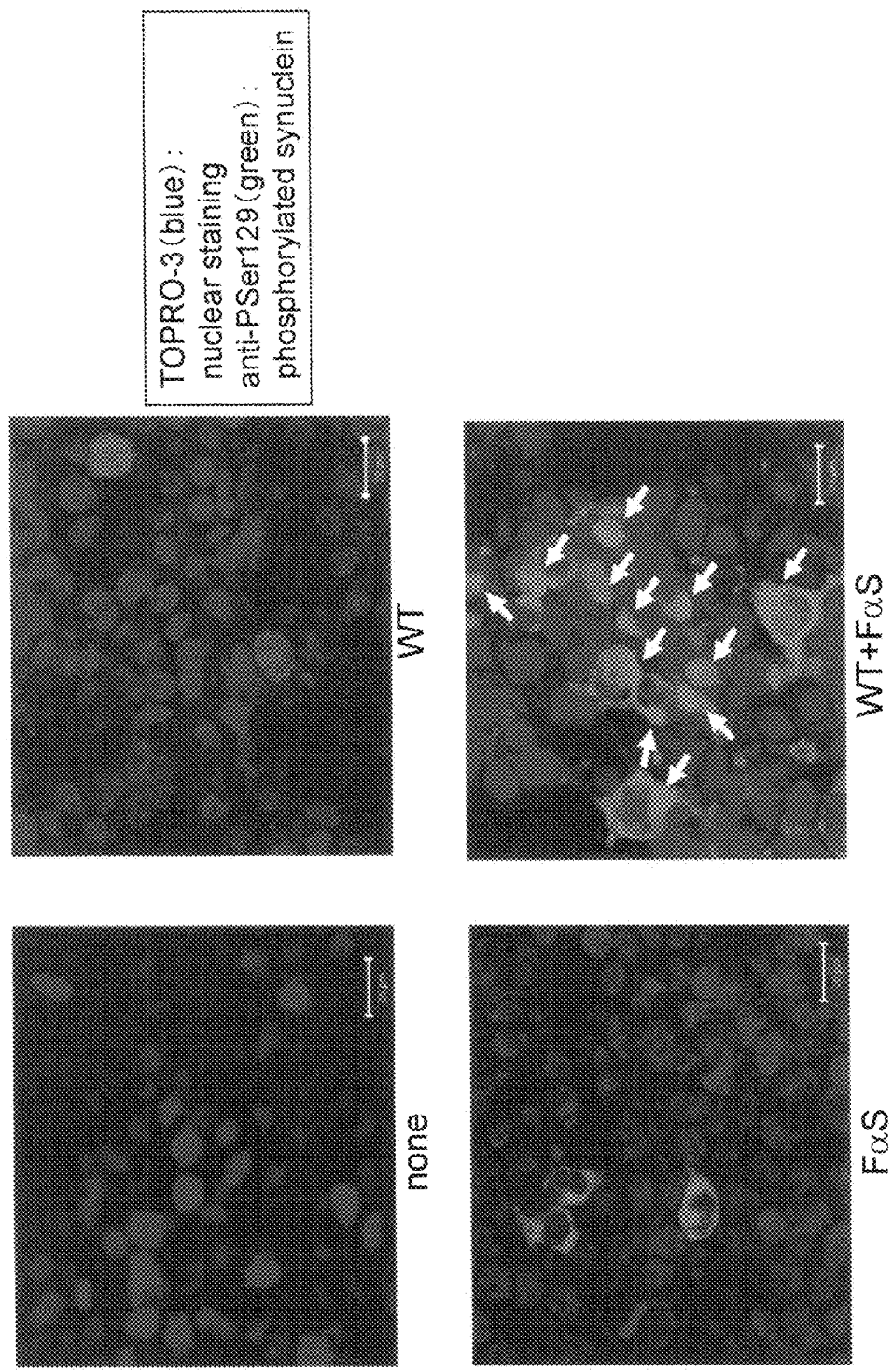
FIG. 3 shows the results of observations using a confocal laser microscope after immunological staining with an anti-PSer129 antibody specifically recognizing phosphorylated α-synuclein.

As shown in FIG. 3, few cells contain phosphorylated synuclein were observed in WT and FαS cells, whereas a number of the anti-PSer129 positive cells were detected in the WT+FαS cells. Round structures (shown by the white arrow in the figure) of radius 10-15 nm which are strongly stained by the antibodies were observed in the cytoplasms of the positive cells. The morphologies and the size are similar to those of Lewy bodies observed in the brains of patients (See FIG. 5).

Properties of Structures in the Cellular Models of α-Synuclein Proteinopathy

In this section, WT+FαS cells were examined to confirm whether or not the round structures (FIG. 3) observed therein were composed of α-synuclein fibrils. Thioflavin S, a fluorescent dye specifically binding to fibrillized protein rich in β-sheet structure was used. The WT+FαS cells were stained using anti-PSer129 antibodies, TO-PRO-3 and thioflavin S and observed using a confocal laser microscope.

Figure 4:
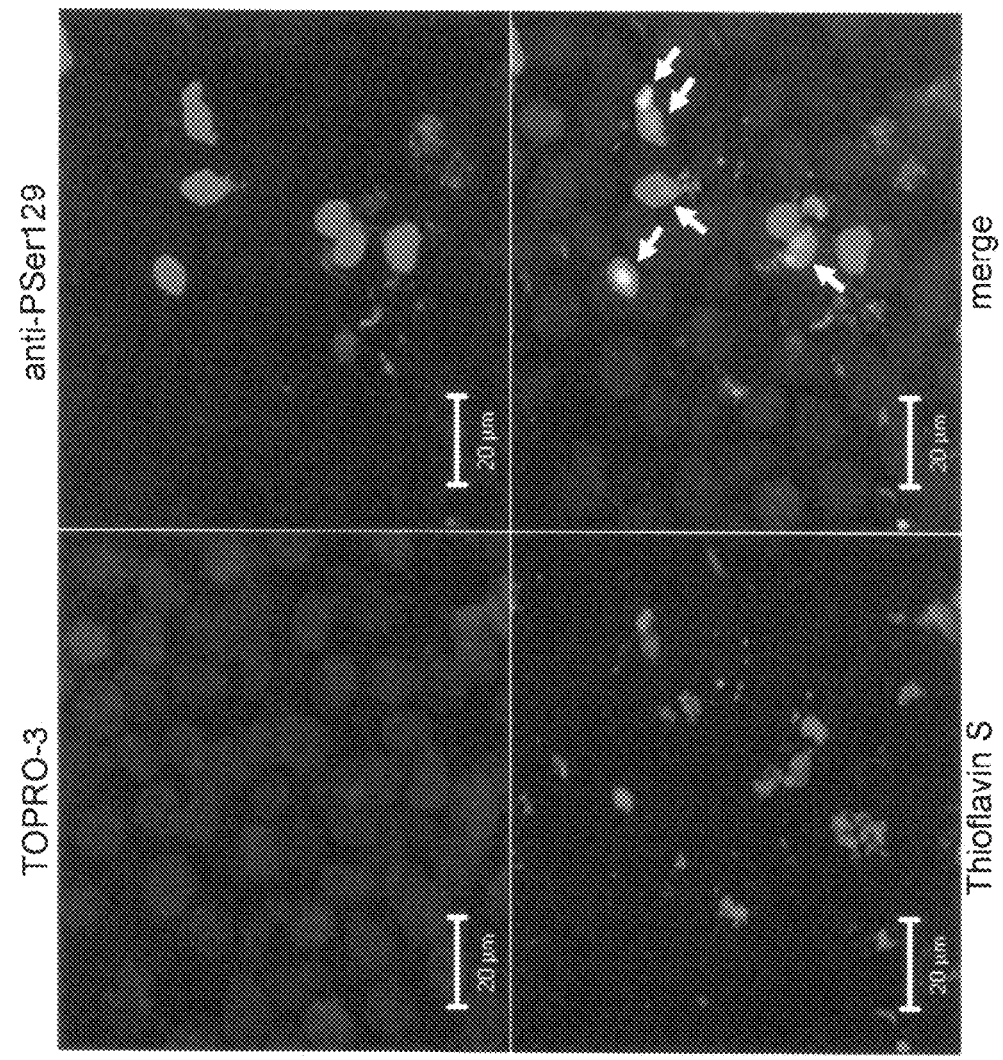
FIG. 4 shows the results of observations of WT+FαS cells after triple staining with an anti-PSer129 antibody, TO-PRO-3 and Thioflavin S using a confocal laser microscope.

As shown in FIG. 4, several round structures stained by antibody to phosphorylated α-synuclein were also positive for thioflavin S (shown by the white arrow in the figure).

This result together with FIG. 2 shows that the round structures observed in the WT+FαS cells are composed of phosphorylated and fibrillized α-synuclein, which is recovered in the detergent-insoluble fraction.

Lewy bodies in the brains of patients are known to be ubiquitinated. Therefore the structures in the WT+FαS cells were examined whether they were ubiquitinated similar to Lewy bodies.

Figure 5:
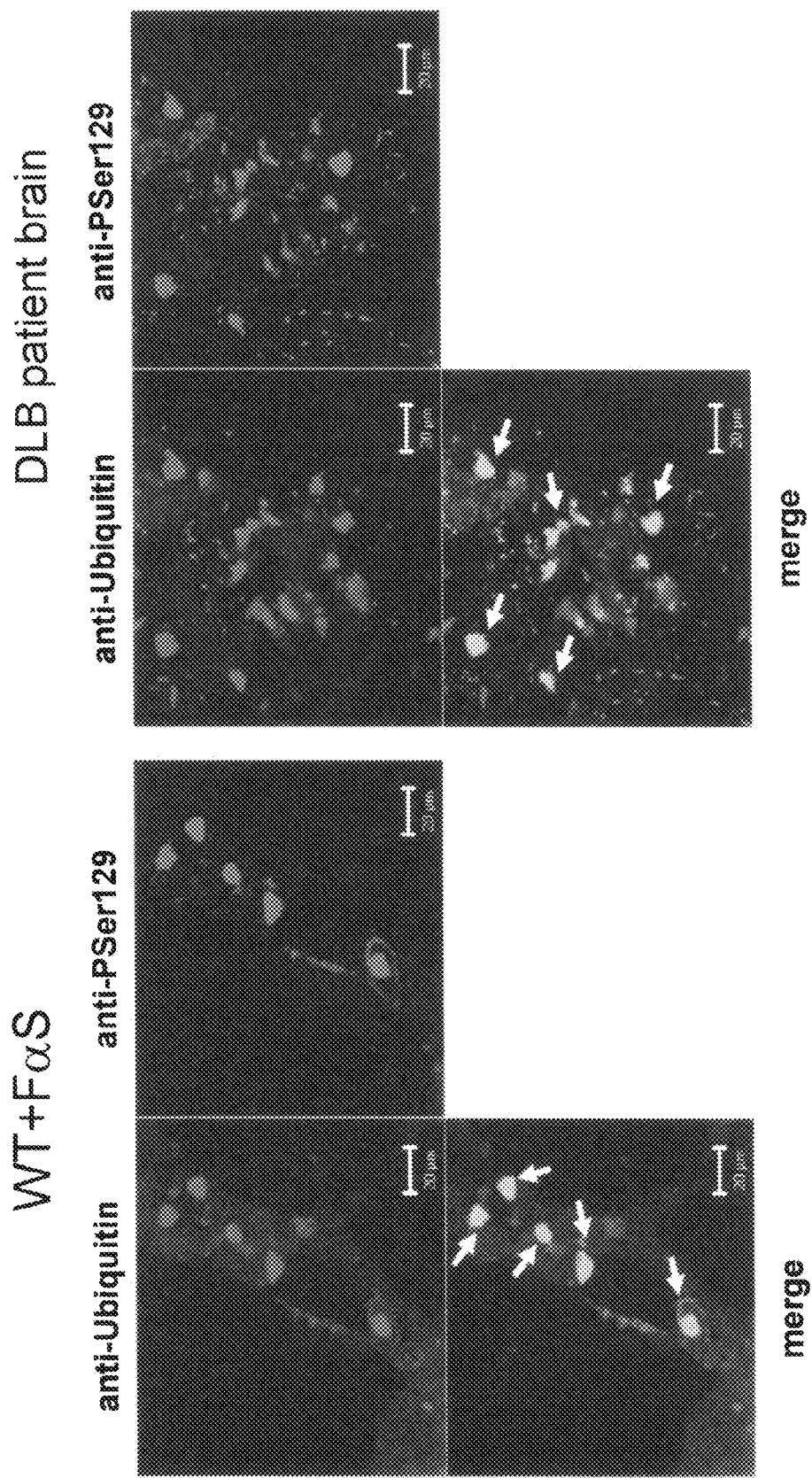
FIG. 5 shows the results of observations of vibratome sections from the brains of patients suffering from dementia with Lewy bodies (DLB) and WT+FαS cells after double staining with an anti-PSer129 antibody and an ubiquitin antibody using a confocal laser microscope.

WT+FαS cells and vibratome sections from the brains of patients with dementia with Lewy bodies (DLB) were double stained with anti-PSer129 antibody and ubiquitin antibody and observed using a confocal laser microscope. The results are shown in FIG. 5.

Almost all Lewy bodies recognized by an antibody to phosphorylated α-synuclein are also ubiquitin-positive (the white arrow in the figure). It is also clear that the intracellular structures which are positive to phosphorylated α-synuclein antibody in WT+FαS cells are positive for ubiquitin antibody, which is similar to Lewy bodies from the brains of patients (the white arrow in the figure).

From the above results, it is clear that the intracellular structures observed in this cellular model are very similar to Lewy bodies not only in the shape and the size but also in properties such as being ubiquitinated and being composed of phosphorylated α-synuclein fibril.

Cell Death Induced in the Cellular Model of α-Synuclein Proteinopathy

When cells transfected with both α-synuclein plasmid DNA and the fibrils were cultured for three days, clear morphological changes were observed in comparison to untreated cells (FIG. 6(a)). Since a decrease in the number of cells was noted in addition to the morphological changes, in this section, it is examined whether or not the changes resulting from the treatment of WT+FαS cells has any connection to cell death.

A cell death assay was performed on the following three types of cells: untreated cells (none), FαS cells into which only α-synuclein fibril was introduced, and WT+FαS cells into which fibril and α-synuclein plasmid DNA were introduced. After culturing the cells for three days, cell death was evaluated by lactate dehydrogenase (LDH) leakage assay. This assay is based on determining how much LDH originally inside the cell has leaked outside the cell as a result of cell death. Higher extracellular activity of LDH demonstrates more extensive cell death.

The results of the cell death assay are shown in FIG. 6(c). As is shown clearly in the figure, the rate of cell death of untreated cells and cells into which only α-synuclein fibrils were introduced was of the order of 10%. However WT+FαS cells into which fibrils and α-synuclein plasmid DNA were introduced showed a cell death rate of 30%. Thus it is clear that cell death was accompanied with accumulation of α-synuclein in WT+FαS cells.

Inhibition of Cell Death Induced in the Cellular Model of α-Synuclein Proteinopathy It is important to search for agents inhibiting cell death in the WT+FαS cells for development of therapeutic agents of neurodegenerative diseases such as Parkinson's disease.

Gossypetin is a flavonol contained in *Gossypium herbaceum* LINNE and is polyphenol compound used as a food additive. The present inventors firstly examined whether or not Gossypetin inhibits fibrillization of α-synuclein in vitro.

2 mg/mL of α-synuclein was incubated with shaking at 37° C. in the presence or absence of 20 μM of Gossypetin. Fibril formation was measured by thioflavin S fluorescence. Thioflavin S is a test reagent which emits fluorescence upon binding to a protein which can serve as a polymerization nucleus of a protein polymer, or a protein polymer thereof, which is rich in β-sheet structure. Therefore thioflavin S can be used to determine the presence or absence of a protein which can serve as a polymerization nucleus of a protein polymer, or a protein polymer thereof. Since α-synuclein fibrils are rich in β-sheet structure, if Gossypetin inhibits fibrillization of α-synuclein, the fluorescence intensity should be lower than samples in the absence of Gossypetin.

Figure 7:
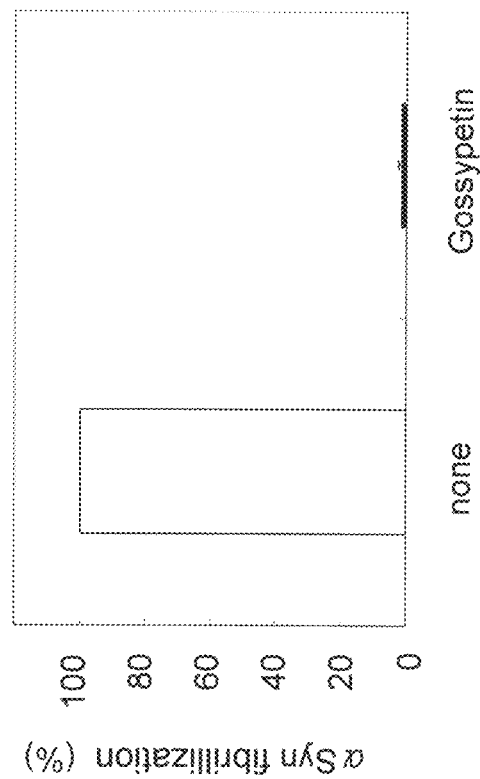
FIG. 7 shows the inhibition of fibrillization of α-synuclein in vitro by Gossypetin.

The results show that when Gossypetin is added, a conspicuous decrease in the fluorescence intensity is observed in comparison to sample to which it is not added (FIG. 7).

Thus it is shown that Gossypetin inhibits the fibrillization of α-synuclein in vitro.

Since a conspicuous decrease in fibrillization of α-synuclein in vitro was confirmed, experiments were performed to investigate whether Gossypetin inhibits cell death induced in WT+FαS cells.

Gossypetin was added to SH-SY5Y cells into which α-synuclein plasmid and fibrils are introduced, and incubated for three days. A cell death assay was then performed.

The results are shown in FIG. 8. As shown in FIG. 8, when a polyphenol compound is not added the rate of cell death is approximately 50%. However when Gossypetin is added, there is a conspicuous inhibition of the rate of cell death. These results show that Gossypetin has inhibiting effects on cell death induced in WT+FαS cells.

From the above, it is clear that the method of the present invention allows simple screening of compounds or naturally occurring substances inhibiting cell death resulting from α-synuclein accumulation. Compounds found by this screening method may provide new targets as therapeutic agents for neurodegenerative diseases or Parkinson's disease and the method of the present invention is an extremely useful screening method.

INDUSTRIAL APPLICABILITY

The present invention provides a cell into which a protein which can serve as a polymerization nucleus of a protein polymer, or a protein polymer thereof, is introduced, and a method for producing the cell. The cell according to the present invention can be used as a model which has the characteristic structures actually observed in the brains of patients with neurodegenerative diseases and is useful for analyzing the pathogenesis of Alzheimer's disease or Parkinson's disease. The cell according to the present invention is extremely useful for analyzing the mechanisms of pathogenesis common to amyloidosis and various types of neurodegenerative diseases. Furthermore the cell according to the present invention can easily be adapted for use in screening for compounds inhibiting the intracellular accumulation of proteins such as tau protein or α-synuclein and can be expected to play a role in the development of the therapeutic agents operating by new modes of action.

What is claimed is:

1. A method for producing a cellular model of α-synuclein inclusion formation by polymerization, wherein the method comprises:
introducing into a neuron or a glial cell, by use of a lipid transport reagent, an α-synuclein fibril formed from α-synuclein of SEQ ID NO: 2 or a mutant thereof at A30P, A53T, or E46K or a variant thereof with portion(s) deleted in any or all of the amino acid residues at positions 10 to 15, 21 to 26, 32 to 37, 43 to 48, and 58 to 63, said α-synuclein fibril being a suitable polymerization nucleus of filamentous α-synuclein inclusions;
introducing into a neuron or a glial cell an expression vector encoding a recombinant α-synuclein of SEQ ID NO: 2 or a mutant thereof at A30P, A53T, or E46K or a variant thereof with portion(s) deleted in any or all of the amino acid residues at positions 10 to 15, 21 to 26, 32 to 37, 43 to 48, and 58 to 63; and
thereby causing interaction between the α-synuclein fibril and the recombinant α-synuclein generated by expression of the vector forming filamentous α-synuclein inclusions in the cell by polymerization,
wherein the α-synuclein fibril which can serve as a polymerization nucleus and the recombinant α-synuclein generated in the cell are phosphorylated in the cell.

2. The method according to claim 1, wherein the expression plasmid comprises the polynucleotide having the sequence set forth in SEQ ID NO: 1, which encodes the α-synuclein having the polypeptide sequence set forth in SEQ ID NO: 2.

3. The method according to claim 1, wherein the α-synuclein fibril or the recombinant α-synuclein comprises a variant of α-synuclein having amino acid residue 30 of SEQ ID NO: 2 substituted with proline; having amino acid residue 46 of SEQ ID NO: 2 substituted with lysine; or having amino acid residue 53 of SEQ ID NO: 2 substituted with threonine.

4. The method according to claim 1, wherein the lipid transport regent is a 3:1 (w/w) formulation of the polycationic lipid 2,3-dioleyloxy-N-[2(sperminecarboxamido) ethyl]-N,N-dimethyl-1-propanaminium trifluoroacetate (DOSPA) and the neutral lipid dioleoyl phosphatidylethanolamine (DOPE).

* * * * *

SEQUENCE LISTING

<160> NUMBER OF SEQ ID NOS: 12

<210> SEQ ID NO 1
<211> LENGTH: 1549
<212> TYPE: DNA
<213> ORGANISM: Homo sapiens
<220> FEATURE:
<221> NAME/KEY: CDS
<222> LOCATION: (53)..(475)

<400> SEQUENCE: 1

```
gctctcggag tggccattcg acgacagtgt ggtgtaaagg aattcattag cc atg gat      58
                                                         Met Asp
                                                          1 gta ttc atg aaa gga ctt tca aag gcc aag gag gga gtt gtg gct gct      106
Val Phe Met Lys Gly Leu Ser Lys Ala Lys Glu Gly Val Val Ala Ala
      5              10                  15 gct gag aaa acc aaa cag ggt gtg gca gaa gca gca gga aag aca aaa      154
Ala Glu Lys Thr Lys Gln Gly Val Ala Glu Ala Ala Gly Lys Thr Lys
 20                  25                  30 gag ggt gtt ctc tat gta ggc tcc aaa acc aag gag gga gtg gtg cat      202
Glu Gly Val Leu Tyr Val Gly Ser Lys Thr Lys Glu Gly Val Val His
 35                  40                  45                  50 ggt gtg gca aca gtg gct gag aag acc aaa gag caa gtg aca aat gtt      250
Gly Val Ala Thr Val Ala Glu Lys Thr Lys Glu Gln Val Thr Asn Val
                 55                  60                  65 gga gga gca gtg gtg acg ggt gtg aca gca gta gcc cag aag aca gtg      298
Gly Gly Ala Val Val Thr Gly Val Thr Ala Val Ala Gln Lys Thr Val
             70                  75                  80 gag gga gca ggg agc att gca gca gcc act ggc ttt gtc aaa aag gac      346
Glu Gly Ala Gly Ser Ile Ala Ala Ala Thr Gly Phe Val Lys Lys Asp
         85                  90                  95 cag ttg ggc aag aat gaa gaa gga gcc cca cag gaa gga att ctg gaa      394
Gln Leu Gly Lys Asn Glu Glu Gly Ala Pro Gln Glu Gly Ile Leu Glu
    100                 105                 110 gat atg cct gtg gat cct gac aat gag gct tat gaa atg cct tct gag      442
Asp Met Pro Val Asp Pro Asp Asn Glu Ala Tyr Glu Met Pro Ser Glu
115                 120                 125                 130 gaa ggg tat caa gac tac gaa cct gaa gcc taa gaaatatctt tgctcccagt     495
Glu Gly Tyr Gln Asp Tyr Glu Pro Glu Ala
                135                 140 ttcttgagat ctgctgacag atgttccatc ctgtacaagt gctcagttcc aatgtgccca    555
gtcatgacat ttctcaaagt ttttacagtg tatctcgaag tcttccatca gcagtgattg    615
aagtatctgt acctgcccc actcagcatt tcggtgcttc cctttcactg aagtgaatac    675
atggtagcag ggtctttgtg tgctgtggat tttgtggctt caatctacga tgttaaaaca    735
aattaaaaac acctaagtga ctaccactta tttctaaatc ctcactattt ttttgttgct    795
gttgttcaga agttgttagt gatttgctat catatattat aagattttta ggtgtctttt    855
aatgatactg tctaagaata atgacgtatt gtgaaatttg ttaatatata taatacttaa    915
aaatatgtga gcatgaaact atgcacctat aaatactaaa tatgaaattt taccattttg    975
cgatgtgttt tattcacttg tgtttgtata taaatggtga gaattaaaat aaaacgttat    1035
ctcattgcaa aaatatttta tttttatccc atctcacttt aataataaaa atcatgctta    1095
taagcaacat gaattaagaa ctgacacaaa ggacaaaaat ataagttat taatagccat      1155
```

-continued

```
ttgaagaagg aggaattttta gaagaggtag agaaaatgga acattaaccc tacactcgga      1215
attccctgaa gcaacactgc cagaagtgtg ttttggtatg cactggttcc ttaagtggct      1275
gtgattaatt attgaaagtg gggtgttgaa gaccccaact actattgtag agtggtctat      1335
ttctcccttc aatcctgtca atgtttgctt tatgtatttt ggggaactgt tgtttgatgt      1395
gtatgtgttt ataattgtta tacattttta attgagcctt ttattaacat atattgttat      1455
ttttgtctcg aaataatttt ttagttaaaa tctattttgt ctgatattgg tgtgaatgct      1515
gtacctttct gacaataaat aatattcgac catg                                  1549
```

<210> SEQ ID NO 2
<211> LENGTH: 140
<212> TYPE: PRT
<213> ORGANISM: Homo sapiens

<400> SEQUENCE: 2

```
Met Asp Val Phe Met Lys Gly Leu Ser Lys Ala Lys Glu Gly Val Val
1               5                   10                  15

Ala Ala Ala Glu Lys Thr Lys Gln Gly Val Ala Glu Ala Ala Gly Lys
            20                  25                  30

Thr Lys Glu Gly Val Leu Tyr Val Gly Ser Lys Thr Lys Glu Gly Val
        35                  40                  45

Val His Gly Val Ala Thr Val Ala Glu Lys Thr Lys Glu Gln Val Thr
    50                  55                  60

Asn Val Gly Gly Ala Val Val Thr Gly Val Thr Ala Val Ala Gln Lys
65                  70                  75                  80

Thr Val Glu Gly Ala Gly Ser Ile Ala Ala Ala Thr Gly Phe Val Lys
                85                  90                  95

Lys Asp Gln Leu Gly Lys Asn Glu Glu Gly Ala Pro Gln Glu Gly Ile
            100                 105                 110

Leu Glu Asp Met Pro Val Asp Pro Asp Asn Glu Ala Tyr Glu Met Pro
        115                 120                 125

Ser Glu Glu Gly Tyr Gln Asp Tyr Glu Pro Glu Ala
    130                 135                 140
```

<210> SEQ ID NO 3
<211> LENGTH: 2796
<212> TYPE: DNA
<213> ORGANISM: Homo sapiens
<220> FEATURE:
<221> NAME/KEY: CDS
<222> LOCATION: (237)..(1562)

<400> SEQUENCE: 3

```
cctcccctgg ggaggctcgc gttcccgctg ctcgcgcctg ccgcccgccg gcctcaggaa       60
cgcgccctct cgccgcgcgc gccctcgcag tcaccgccac ccaccagctc cggcaccaac      120
agcagcgccg ctgccaccgc ccaccttctg ccgccgccac cacagccacc ttctcctcct      180
ccgctgtcct ctcccgtcct cgcctctgtc gactatcagg tgaactttga accagg atg      239
                                                                  Met
                                                                   1 gct gag ccc cgc cag gag ttc gaa gtg atg gaa gat cac gct ggg acg       287
Ala Glu Pro Arg Gln Glu Phe Glu Val Met Glu Asp His Ala Gly Thr
            5                   10                  15 tac ggg ttg ggg gac agg aaa gat cag ggg ggc tac acc atg cac caa       335
Tyr Gly Leu Gly Asp Arg Lys Asp Gln Gly Gly Tyr Thr Met His Gln
        20                  25                  30
```

-continued

| | | |
|---|---|---|
| gac caa gag ggt gac acg gac gct ggc ctg aaa gaa tct ccc ctg cag<br>Asp Gln Glu Gly Asp Thr Asp Ala Gly Leu Lys Glu Ser Pro Leu Gln<br>35                  40                      45 | | 383 |
| acc ccc act gag gac gga tct gag gaa ccg ggc tct gaa acc tct gat<br>Thr Pro Thr Glu Asp Gly Ser Glu Glu Pro Gly Ser Glu Thr Ser Asp<br>50                  55                      60                  65 | | 431 |
| gct aag agc act cca aca gcg gaa gat gtg aca gca ccc tta gtg gat<br>Ala Lys Ser Thr Pro Thr Ala Glu Asp Val Thr Ala Pro Leu Val Asp<br>                  70                      75                      80 | | 479 |
| gag gga gct ccc ggc aag cag gct gcc gcg cag ccc cac acg gag atc<br>Glu Gly Ala Pro Gly Lys Gln Ala Ala Ala Gln Pro His Thr Glu Ile<br>                85                      90                      95 | | 527 |
| cca gaa gga acc aca gct gaa gaa gca ggc att gga gac acc ccc agc<br>Pro Glu Gly Thr Thr Ala Glu Glu Ala Gly Ile Gly Asp Thr Pro Ser<br>        100                      105                      110 | | 575 |
| ctg gaa gac gaa gct gct ggt cac gtg acc caa gct cgc atg gtc agt<br>Leu Glu Asp Glu Ala Ala Gly His Val Thr Gln Ala Arg Met Val Ser<br>115                        120                      125 | | 623 |
| aaa agc aaa gac ggg act gga agc gat gac aaa aaa gcc aag ggg gct<br>Lys Ser Lys Asp Gly Thr Gly Ser Asp Asp Lys Lys Ala Lys Gly Ala<br>130                        135                    140                  145 | | 671 |
| gat ggt aaa acg aag atc gcc aca ccg cgg gga gca gcc cct cca ggc<br>Asp Gly Lys Thr Lys Ile Ala Thr Pro Arg Gly Ala Ala Pro Pro Gly<br>                  150                      155                      160 | | 719 |
| cag aag ggc cag gcc aac gcc acc agg att cca gca aaa acc ccg ccc<br>Gln Lys Gly Gln Ala Asn Ala Thr Arg Ile Pro Ala Lys Thr Pro Pro<br>                  165                      170                      175 | | 767 |
| gct cca aag aca cca ccc agc tct ggt gaa cct cca aaa tca ggg gat<br>Ala Pro Lys Thr Pro Pro Ser Ser Gly Glu Pro Pro Lys Ser Gly Asp<br>180                        185                    190 | | 815 |
| cgc agc ggc tac agc agc ccc ggc tcc cca ggc act ccc ggc agc cgc<br>Arg Ser Gly Tyr Ser Ser Pro Gly Ser Pro Gly Thr Pro Gly Ser Arg<br>                  195                      200                      205 | | 863 |
| tcc cgc acc ccg tcc ctt cca acc cca ccc acc cgg gag ccc aag aag<br>Ser Arg Thr Pro Ser Leu Pro Thr Pro Pro Thr Arg Glu Pro Lys Lys<br>210                        215                    220                  225 | | 911 |
| gtg gca gtg gtc cgt act cca ccc aag tcg ccg tct tcc gcc aag agc<br>Val Ala Val Val Arg Thr Pro Pro Lys Ser Pro Ser Ser Ala Lys Ser<br>                  230                      235                      240 | | 959 |
| cgc ctg cag aca gcc ccc gtg ccc atg cca gac ctg aag aat gtc aag<br>Arg Leu Gln Thr Ala Pro Val Pro Met Pro Asp Leu Lys Asn Val Lys<br>                  245                      250                      255 | | 1007 |
| tcc aag atc ggc tcc act gag aac ctg aag cac cag ccg gga ggc ggg<br>Ser Lys Ile Gly Ser Thr Glu Asn Leu Lys His Gln Pro Gly Gly Gly<br>260                        265                    270 | | 1055 |
| aag gtg cag ata att aat aag aag ctg gat ctt agc aac gtc cag tcc<br>Lys Val Gln Ile Ile Asn Lys Lys Leu Asp Leu Ser Asn Val Gln Ser<br>275                        280                    285 | | 1103 |
| aag tgt ggc tca aag gat aat atc aaa cac gtc ccg gga ggc ggc agt<br>Lys Cys Gly Ser Lys Asp Asn Ile Lys His Val Pro Gly Gly Gly Ser<br>290                        295                    300                  305 | | 1151 |
| gtg caa ata gtc tac aaa cca gtt gac ctg agc aag gtg acc tcc aag<br>Val Gln Ile Val Tyr Lys Pro Val Asp Leu Ser Lys Val Thr Ser Lys<br>                  310                      315                      320 | | 1199 |
| tgt ggc tca tta ggc aac atc cat cat aaa cca gga ggt ggc cag gtg<br>Cys Gly Ser Leu Gly Asn Ile His His Lys Pro Gly Gly Gly Gln Val<br>                  325                      330                      335 | | 1247 |
| gaa gta aaa tct gag aag ctt gac ttc aag gac aga gtc cag tcg aag<br>Glu Val Lys Ser Glu Lys Leu Asp Phe Lys Asp Arg Val Gln Ser Lys<br>340                        345                    350 | | 1295 |

-continued

```
att ggg tcc ctg gac aat atc acc cac gtc cct ggc gga gga aat aaa      1343
Ile Gly Ser Leu Asp Asn Ile Thr His Val Pro Gly Gly Gly Asn Lys
    355                 360                 365 aag att gaa acc cac aag ctg acc ttc cgc gag aac gcc aaa gcc aag      1391
Lys Ile Glu Thr His Lys Leu Thr Phe Arg Glu Asn Ala Lys Ala Lys
370                 375                 380                 385 aca gac cac ggg gcg gag atc gtg tac aag tcg cca gtg gtg tct ggg      1439
Thr Asp His Gly Ala Glu Ile Val Tyr Lys Ser Pro Val Val Ser Gly
                390                 395                 400 gac acg tct cca cgg cat ctc agc aat gtc tcc tcc acc ggc agc atc      1487
Asp Thr Ser Pro Arg His Leu Ser Asn Val Ser Ser Thr Gly Ser Ile
            405                 410                 415 gac atg gta gac tcg ccc cag ctc gcc acg cta gct gac gag gtg tct      1535
Asp Met Val Asp Ser Pro Gln Leu Ala Thr Leu Ala Asp Glu Val Ser
        420                 425                 430 gcc tcc ctg gcc aag cag ggt ttg tga tcaggcccct ggggcggtca            1582
Ala Ser Leu Ala Lys Gln Gly Leu
    435                 440 ataattgtgg agaggagaga atgagagagt gtggaaaaaa aagaataat gacccggccc     1642 ccgccctctg cccccagctg ctcctcgcag ttcggttaat tggttaatca cttaacctgc    1702
ttttgtcact cggctttggc tcgggacttc aaaatcagtg atgggagtaa gagcaaattt    1762 catcttttcca aattgatggg tgggctagta ataaaatatt taaaaaaaaa cattcaaaaa   1822
catggccaca tccaacattt cctcaggcaa ttcctttga ttcttttttc ttccccctcc     1882
atgtagaaga gggagaagga gaggctctga aagctgcttc tggggatttt caagggactg    1942
ggggtgccaa ccacctctgg ccctgttgtg ggggttgtca cagaggcagt ggcagcaaca    2002
aaggatttga aaactttggt gtgttcgtgg agccacaggc agacgatgtc aaccttgtgt    2062
gagtgtgacg ggggttgggg tgggcggga ggccacgggg gaggccgagg cagggctgg      2122 gcagagggga ggaggaagca caagaagtgg gagtgggaga ggaagccacg tgctggagag    2182
tagacatccc cctccttgcc gctgggagag ccaaggccta tgccacctgc agcgtctgag    2242
cggccgcctg tccttggtgg ccgggggtgg gggcctgctg tgggtcagtg tgccaccctc    2302
tgcagggcag cctgtgggag aagggacagc gggttaaaaa gagaaggcaa gcctggcagg    2362
agggttggca cttcgatgat gacctcctta gaaagactga ccttgatgtc ttgagagcgc    2422
tggcctcttc ctcccctccct gcagggtagg gcgcctgagc ctaggcggtt ccctctgctc   2482
cacagaaacc ctgttttatt gagttctgaa ggttggaact gctgccatga ttttggccac    2542
tttgcagacc tgggactta gggctaacca gttctctttg taaggacttg tgcctcttgg     2602
gagacgtcca cccgtttcca agcctgggcc actggcatct ctggagtgtg tgggggtctg    2662
ggaggcaggt cccgagcccc ctgtccttcc cacggccact gcagtcaccc cgtctgcgcc    2722
gctgtgctgt tgtctgccgt gagagcccaa tcactgccta taccctcat cacacgtcac     2782 aatgtcccga attc                                                      2796
```

<210> SEQ ID NO 4
<211> LENGTH: 441
<212> TYPE: PRT
<213> ORGANISM: Homo sapiens

<400> SEQUENCE: 4

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His

```
            20                  25                  30
Gln Asp Gln Glu Gly Asp Thr Asp Ala Gly Leu Lys Glu Ser Pro Leu
            35                  40                  45
Gln Thr Pro Thr Glu Asp Gly Ser Glu Glu Pro Gly Ser Glu Thr Ser
        50                  55                  60
Asp Ala Lys Ser Thr Pro Thr Ala Glu Asp Val Thr Ala Pro Leu Val
65                  70                  75                  80
Asp Glu Gly Ala Pro Gly Lys Gln Ala Ala Gln Pro His Thr Glu
                85                  90                  95
Ile Pro Glu Gly Thr Thr Ala Glu Glu Ala Gly Ile Gly Asp Thr Pro
            100                 105                 110
Ser Leu Glu Asp Glu Ala Ala Gly His Val Thr Gln Ala Arg Met Val
            115                 120                 125
Ser Lys Ser Lys Asp Gly Thr Gly Ser Asp Asp Lys Ala Lys Gly
            130                 135                 140
Ala Asp Gly Lys Thr Lys Ile Ala Thr Pro Arg Gly Ala Ala Pro Pro
145                 150                 155                 160
Gly Gln Lys Gly Gln Ala Asn Ala Thr Arg Ile Pro Ala Lys Thr Pro
                165                 170                 175
Pro Ala Pro Lys Thr Pro Ser Ser Gly Glu Pro Pro Lys Ser Gly
            180                 185                 190
Asp Arg Ser Gly Tyr Ser Ser Pro Gly Ser Pro Gly Thr Pro Gly Ser
            195                 200                 205
Arg Ser Arg Thr Pro Ser Leu Pro Thr Pro Pro Thr Arg Glu Pro Lys
210                 215                 220
Lys Val Ala Val Val Arg Thr Pro Pro Lys Ser Pro Ser Ser Ala Lys
225                 230                 235                 240
Ser Arg Leu Gln Thr Ala Pro Val Pro Met Pro Asp Leu Lys Asn Val
                245                 250                 255
Lys Ser Lys Ile Gly Ser Thr Glu Asn Leu Lys His Gln Pro Gly Gly
            260                 265                 270
Gly Lys Val Gln Ile Ile Asn Lys Lys Leu Asp Leu Ser Asn Val Gln
            275                 280                 285
Ser Lys Cys Gly Ser Lys Asp Asn Ile Lys His Val Pro Gly Gly Gly
            290                 295                 300
Ser Val Gln Ile Val Tyr Lys Pro Val Asp Leu Ser Lys Val Thr Ser
305                 310                 315                 320
Lys Cys Gly Ser Leu Gly Asn Ile His His Lys Pro Gly Gly Gly Gln
                325                 330                 335
Val Glu Val Lys Ser Glu Lys Leu Asp Phe Lys Asp Arg Val Gln Ser
            340                 345                 350
Lys Ile Gly Ser Leu Asp Asn Ile Thr His Val Pro Gly Gly Gly Asn
            355                 360                 365
Lys Lys Ile Glu Thr His Lys Leu Thr Phe Arg Glu Asn Ala Lys Ala
            370                 375                 380
Lys Thr Asp His Gly Ala Glu Ile Val Tyr Lys Ser Pro Val Val Ser
385                 390                 395                 400
Gly Asp Thr Ser Pro Arg His Leu Ser Asn Val Ser Ser Thr Gly Ser
                405                 410                 415
Ile Asp Met Val Asp Ser Pro Gln Leu Ala Thr Leu Ala Asp Glu Val
            420                 425                 430
Ser Ala Ser Leu Ala Lys Gln Gly Leu
            435                 440
```

<210> SEQ ID NO 5
<211> LENGTH: 981
<212> TYPE: DNA
<213> ORGANISM: Homo sapiens
<220> FEATURE:
<221> NAME/KEY: CDS
<222> LOCATION: (149)..(613)

<400> SEQUENCE: 5

```
gtttggggcc agagtgggcg aggcgcggag gtctggccta taaagtagtc gcggagacgg    60
ggtgctggtt tgcgtcgtag tctcctgcag cgtctggggt ttccgttgca gtcctcggaa   120
ccaggacctc ggcgtggcct agcgagtt atg gcg acg aag gcc gtg tgc gtg      172
                                 Met Ala Thr Lys Ala Val Cys Val
                                   1               5 ctg aag ggc gac ggc cca gtg cag ggc atc atc aat ttc gag cag aag    220
Leu Lys Gly Asp Gly Pro Val Gln Gly Ile Ile Asn Phe Glu Gln Lys
         10                  15                  20 gaa agt aat gga cca gtg aag gtg tgg gga agc att aaa gga ctg act    268
Glu Ser Asn Gly Pro Val Lys Val Trp Gly Ser Ile Lys Gly Leu Thr
 25                  30                  35                  40 gaa ggc ctg cat gga ttc cat gtt cat gag ttt gga gat aat aca gca    316
Glu Gly Leu His Gly Phe His Val His Glu Phe Gly Asp Asn Thr Ala
                 45                  50                  55 ggc tgt acc agt gca ggt cct cac ttt aat cct cta tcc aga aaa cac    364
Gly Cys Thr Ser Ala Gly Pro His Phe Asn Pro Leu Ser Arg Lys His
             60                  65                  70 ggt ggg cca aag gat gaa gag agg cat gtt gga gac ttg ggc aat gtg    412
Gly Gly Pro Lys Asp Glu Glu Arg His Val Gly Asp Leu Gly Asn Val
         75                  80                  85 act gct gac aaa gat ggt gtg gcc gat gtg tct att gaa gat tct gtg    460
Thr Ala Asp Lys Asp Gly Val Ala Asp Val Ser Ile Glu Asp Ser Val
 90                  95                 100 atc tca ctc tca gga gac cat tgc atc att ggc cgc aca ctg gtg gtc    508
Ile Ser Leu Ser Gly Asp His Cys Ile Ile Gly Arg Thr Leu Val Val
105                 110                 115                 120 cat gaa aaa gca gat gac ttg ggc aaa ggt gga aat gaa gaa agt aca    556
His Glu Lys Ala Asp Asp Leu Gly Lys Gly Gly Asn Glu Glu Ser Thr
                125                 130                 135 aag aca gga aac gct gga agt cgt ttg gct tgt ggt gta att ggg atc    604
Lys Thr Gly Asn Ala Gly Ser Arg Leu Ala Cys Gly Val Ile Gly Ile
                140                 145                 150 gcc caa taa acattcccctt ggatgtagtc tgaggcccct taactcatct            653
Ala Gln gttatcctgc tagctgtaga aatgtatcct gataaacatt aaacactgta atcttaaaag   713
tgtaattgtg tgacttttc agagttgctt taaagtacct gtagtgagaa actgattat    773 gatcacttgg aagatttgta tagttttata aaactcagtt aaaatgtctg tttcaatgac   833
ctgtattttg ccagacttaa atcacagatg ggtattaaac ttgtcagaat ttctttgtca   893
ttcaagcctg tgaataaaaa ccctgtatgg cacttattat gaggctatta aagaatcca    953 aattcaaact aaaaaaaaaa aaaaaaaa                                     981
```

<210> SEQ ID NO 6
<211> LENGTH: 154
<212> TYPE: PRT
<213> ORGANISM: Homo sapiens

<400> SEQUENCE: 6

```
Met Ala Thr Lys Ala Val Cys Val Leu Lys Gly Asp Gly Pro Val Gln
1               5                   10                  15

Gly Ile Ile Asn Phe Glu Gln Lys Glu Ser Asn Gly Pro Val Lys Val
            20                  25                  30

Trp Gly Ser Ile Lys Gly Leu Thr Glu Gly Leu His Gly Phe His Val
            35                  40                  45

His Glu Phe Gly Asp Asn Thr Ala Gly Cys Thr Ser Ala Gly Pro His
50                  55                  60

Phe Asn Pro Leu Ser Arg Lys His Gly Gly Pro Lys Asp Glu Glu Arg
65                  70                  75                  80

His Val Gly Asp Leu Gly Asn Val Thr Ala Asp Lys Asp Gly Val Ala
                85                  90                  95

Asp Val Ser Ile Glu Asp Ser Val Ile Ser Leu Ser Gly Asp His Cys
            100                 105                 110

Ile Ile Gly Arg Thr Leu Val Val His Glu Lys Ala Asp Asp Leu Gly
            115                 120                 125

Lys Gly Gly Asn Glu Glu Ser Thr Lys Thr Gly Asn Ala Gly Ser Arg
130                 135                 140

Leu Ala Cys Gly Val Ile Gly Ile Ala Gln
145                 150
```

<210> SEQ ID NO 7
<211> LENGTH: 13495
<212> TYPE: DNA
<213> ORGANISM: Homo sapiens
<220> FEATURE:
<221> NAME/KEY: CDS
<222> LOCATION: (146)..(9574)

<400> SEQUENCE: 7

```
gctgccggga cgggtccaag atggacggcc gctcaggttc tgcttttacc tgcggcccag      60
agccccattc attgccccgg tgctgagcgg cgccgcgagt cggcccgagg cctccgggga     120
ctgccgtgcc gggcgggaga ccgcc atg gcg acc ctg gaa aag ctg atg aag      172
                              Met Ala Thr Leu Glu Lys Leu Met Lys
                              1               5 gcc ttc gag tcc ctc aag tcc ttc cag cag cag cag cag cag cag cag      220
Ala Phe Glu Ser Leu Lys Ser Phe Gln Gln Gln Gln Gln Gln Gln Gln
10              15                  20                  25 cag cag cag cag cag cag cag cag cag cag cag caa cag ccg cca ccg      268
Gln Gln Gln Gln Gln Gln Gln Gln Gln Gln Gln Pro Pro Pro
                30                  35                  40 ccg ccg ccg ccg ccg ccg cct cct cag ctt cct cag ccg ccg ccg cag      316
Pro Pro Pro Pro Pro Pro Pro Pro Gln Leu Pro Gln Pro Pro Pro Gln
                45                  50                  55 gca cag ccg ctg ctg cct cag ccg cag ccg ccc ccg ccg ccc ccg          364
Ala Gln Pro Leu Leu Pro Gln Pro Gln Pro Pro Pro Pro Pro Pro
            60                  65                  70 ccg cca ccc ggc ccg gct gtg gct gag gag ccg ctg cac cga cca aag      412
Pro Pro Pro Gly Pro Ala Val Ala Glu Glu Pro Leu His Arg Pro Lys
        75                  80                  85 aaa gaa ctt tca gct acc aag aaa gac cgt gtg aat cat tgt ctg aca      460
Lys Glu Leu Ser Ala Thr Lys Lys Asp Arg Val Asn His Cys Leu Thr
90                  95                  100                 105 ata tgt gaa aac ata gtg gca cag tct gtc aga aat tct cca gaa ttt      508
Ile Cys Glu Asn Ile Val Ala Gln Ser Val Arg Asn Ser Pro Glu Phe
                110                 115                 120 cag aaa ctt ctg ggc atc gct atg gaa ctt ttt ctg ctg tgc agt gat      556
Gln Lys Leu Leu Gly Ile Ala Met Glu Leu Phe Leu Leu Cys Ser Asp
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     |     |     | 125 |     |     |     | 130 |     |     |     | 135 |     |     |     |     |      |
| gac | gca | gag | tca | gat | gtc | agg | atg | gtg | gct | gac | gaa | tgc | ctc | aac | aaa | 604  |
| Asp | Ala | Glu | Ser | Asp | Val | Arg | Met | Val | Ala | Asp | Glu | Cys | Leu | Asn | Lys |      |
|     |     | 140 |     |     |     |     | 145 |     |     |     |     | 150 |     |     |     |      |
| gtt | atc | aaa | gct | ttg | atg | gat | tct | aat | ctt | cca | agg | tta | cag | ctc | gag | 652  |
| Val | Ile | Lys | Ala | Leu | Met | Asp | Ser | Asn | Leu | Pro | Arg | Leu | Gln | Leu | Glu |      |
|     | 155 |     |     |     |     | 160 |     |     |     |     | 165 |     |     |     |     |      |
| ctc | tat | aag | gaa | att | aaa | aag | aat | ggt | gcc | cct | cgg | agt | ttg | cgt | gct | 700  |
| Leu | Tyr | Lys | Glu | Ile | Lys | Lys | Asn | Gly | Ala | Pro | Arg | Ser | Leu | Arg | Ala |      |
| 170 |     |     |     |     | 175 |     |     |     |     | 180 |     |     |     |     | 185 |      |
| gcc | ctg | tgg | agg | ttt | gct | gag | ctg | gct | cac | ctg | gtt | cgg | cct | cag | aaa | 748  |
| Ala | Leu | Trp | Arg | Phe | Ala | Glu | Leu | Ala | His | Leu | Val | Arg | Pro | Gln | Lys |      |
|     |     |     | 190 |     |     |     |     | 195 |     |     |     |     | 200 |     |     |      |
| tgc | agg | cct | tac | ctg | gtg | aac | ctt | ctg | ccg | tgc | ctg | act | cga | aca | agc | 796  |
| Cys | Arg | Pro | Tyr | Leu | Val | Asn | Leu | Leu | Pro | Cys | Leu | Thr | Arg | Thr | Ser |      |
|     |     | 205 |     |     |     |     | 210 |     |     |     |     | 215 |     |     |     |      |
| aag | aga | ccc | gaa | gaa | tca | gtc | cag | gag | acc | ttg | gct | gca | gct | gtt | ccc | 844  |
| Lys | Arg | Pro | Glu | Glu | Ser | Val | Gln | Glu | Thr | Leu | Ala | Ala | Ala | Val | Pro |      |
|     | 220 |     |     |     |     | 225 |     |     |     |     | 230 |     |     |     |     |      |
| aaa | att | atg | gct | tct | ttt | ggc | aat | ttt | gca | aat | gac | aat | gaa | att | aag | 892  |
| Lys | Ile | Met | Ala | Ser | Phe | Gly | Asn | Phe | Ala | Asn | Asp | Asn | Glu | Ile | Lys |      |
|     |     | 235 |     |     |     |     | 240 |     |     |     |     | 245 |     |     |     |      |
| gtt | ttg | tta | aag | gcc | ttc | ata | gcg | aac | ctg | aag | tca | agc | tcc | ccc | acc | 940  |
| Val | Leu | Leu | Lys | Ala | Phe | Ile | Ala | Asn | Leu | Lys | Ser | Ser | Ser | Pro | Thr |      |
| 250 |     |     |     |     | 255 |     |     |     |     | 260 |     |     |     |     | 265 |      |
| att | cgg | cgg | aca | gcg | gct | gga | tca | gca | gtg | agc | atc | tgc | cag | cac | tca | 988  |
| Ile | Arg | Arg | Thr | Ala | Ala | Gly | Ser | Ala | Val | Ser | Ile | Cys | Gln | His | Ser |      |
|     |     |     | 270 |     |     |     |     | 275 |     |     |     |     | 280 |     |     |      |
| aga | agg | aca | caa | tat | ttc | tat | agt | tgg | cta | cta | aat | gtg | ctc | tta | ggc | 1036 |
| Arg | Arg | Thr | Gln | Tyr | Phe | Tyr | Ser | Trp | Leu | Leu | Asn | Val | Leu | Leu | Gly |      |
|     |     | 285 |     |     |     |     | 290 |     |     |     |     | 295 |     |     |     |      |
| tta | ctc | gtt | cct | gtc | gag | gat | gaa | cac | tcc | act | ctg | ctg | att | ctt | ggc | 1084 |
| Leu | Leu | Val | Pro | Val | Glu | Asp | Glu | His | Ser | Thr | Leu | Leu | Ile | Leu | Gly |      |
|     | 300 |     |     |     |     | 305 |     |     |     |     | 310 |     |     |     |     |      |
| gtg | ctg | ctc | acc | ctg | agg | tat | ttg | gtg | ccc | ttg | ctg | cag | cag | cag | gtc | 1132 |
| Val | Leu | Leu | Thr | Leu | Arg | Tyr | Leu | Val | Pro | Leu | Leu | Gln | Gln | Gln | Val |      |
|     | 315 |     |     |     |     | 320 |     |     |     |     | 325 |     |     |     |     |      |
| aag | gac | aca | agc | ctg | aaa | ggc | agc | ttc | gga | gtg | aca | agg | aaa | gaa | atg | 1180 |
| Lys | Asp | Thr | Ser | Leu | Lys | Gly | Ser | Phe | Gly | Val | Thr | Arg | Lys | Glu | Met |      |
| 330 |     |     |     |     | 335 |     |     |     |     | 340 |     |     |     |     | 345 |      |
| gaa | gtc | tct | cct | tct | gca | gag | cag | ctt | gtc | cag | gtt | tat | gaa | ctg | acg | 1228 |
| Glu | Val | Ser | Pro | Ser | Ala | Glu | Gln | Leu | Val | Gln | Val | Tyr | Glu | Leu | Thr |      |
|     |     |     |     | 350 |     |     |     |     | 355 |     |     |     |     | 360 |     |      |
| tta | cat | cat | aca | cag | cac | caa | gac | cac | aat | gtt | gtg | acc | gga | gcc | ctg | 1276 |
| Leu | His | His | Thr | Gln | His | Gln | Asp | His | Asn | Val | Val | Thr | Gly | Ala | Leu |      |
|     |     |     | 365 |     |     |     |     | 370 |     |     |     |     | 375 |     |     |      |
| gag | ctg | ttg | cag | cag | ctc | ttc | aga | acg | cct | cca | ccc | gag | ctt | ctg | caa | 1324 |
| Glu | Leu | Leu | Gln | Gln | Leu | Phe | Arg | Thr | Pro | Pro | Pro | Glu | Leu | Leu | Gln |      |
|     |     | 380 |     |     |     |     | 385 |     |     |     |     | 390 |     |     |     |      |
| acc | ctg | acc | gca | gtc | ggg | ggc | att | ggg | cag | ctc | acc | gct | gct | aag | gag | 1372 |
| Thr | Leu | Thr | Ala | Val | Gly | Gly | Ile | Gly | Gln | Leu | Thr | Ala | Ala | Lys | Glu |      |
|     | 395 |     |     |     |     | 400 |     |     |     |     | 405 |     |     |     |     |      |
| gag | tct | ggt | ggc | cga | agc | cgt | agt | ggg | agt | att | gtg | gaa | ctt | ata | gct | 1420 |
| Glu | Ser | Gly | Gly | Arg | Ser | Arg | Ser | Gly | Ser | Ile | Val | Glu | Leu | Ile | Ala |      |
| 410 |     |     |     |     | 415 |     |     |     |     | 420 |     |     |     |     | 425 |      |
| gga | ggg | ggt | tcc | tca | tgc | agc | cct | gtc | ctt | tca | aga | aaa | caa | aaa | ggc | 1468 |
| Gly | Gly | Gly | Ser | Ser | Cys | Ser | Pro | Val | Leu | Ser | Arg | Lys | Gln | Lys | Gly |      |
|     |     |     |     | 430 |     |     |     |     | 435 |     |     |     |     | 440 |     |      |
| aaa | gtg | ctc | tta | gga | gaa | gaa | gaa | gcc | ttg | gag | gat | gac | tct | gaa | tcg | 1516 |

```
        Lys Val Leu Leu Gly Glu Glu Glu Ala Leu Glu Asp Asp Ser Glu Ser
                    445                 450                 455 aga tcg gat gtc agc agc tct gcc tta aca gcc tca gtg aag gat gag        1564
Arg Ser Asp Val Ser Ser Ser Ala Leu Thr Ala Ser Val Lys Asp Glu
                460                 465                 470 atc agt gga gag ctg gct gct tct tca ggg gtt tcc act cca ggg tca        1612
Ile Ser Gly Glu Leu Ala Ala Ser Ser Gly Val Ser Thr Pro Gly Ser
    475                 480                 485 gca ggt cat gac atc atc aca gaa cag cca cgg tca cag cac aca ctg        1660
Ala Gly His Asp Ile Ile Thr Glu Gln Pro Arg Ser Gln His Thr Leu
490                 495                 500                 505 cag gcg gac tca gtg gat ctg gcc agc tgt gac ttg aca agc tct gcc        1708
Gln Ala Asp Ser Val Asp Leu Ala Ser Cys Asp Leu Thr Ser Ser Ala
                510                 515                 520 act gat ggg gat gag gag gat atc ttg agc cac agc tcc agc cag gtc        1756
Thr Asp Gly Asp Glu Glu Asp Ile Leu Ser His Ser Ser Ser Gln Val
                525                 530                 535 agc gcc gtc cca tct gac cct gcc atg gac ctg aat gat ggg acc cag        1804
Ser Ala Val Pro Ser Asp Pro Ala Met Asp Leu Asn Asp Gly Thr Gln
            540                 545                 550 gcc tcg tcg ccc atc agc gac agc tcc cag acc acc acc gaa ggg cct        1852
Ala Ser Ser Pro Ile Ser Asp Ser Ser Gln Thr Thr Thr Glu Gly Pro
555                 560                 565 gat tca gct gtt acc cct tca gac agt tct gaa att gtg tta gac ggt        1900
Asp Ser Ala Val Thr Pro Ser Asp Ser Ser Glu Ile Val Leu Asp Gly
570                 575                 580                 585 acc gac aac cag tat ttg ggc ctg cag att gga cag ccc cag gat gaa        1948
Thr Asp Asn Gln Tyr Leu Gly Leu Gln Ile Gly Gln Pro Gln Asp Glu
                590                 595                 600 gat gag gaa gcc aca ggt att ctt cct gat gaa gcc tcg gag gcc ttc        1996
Asp Glu Glu Ala Thr Gly Ile Leu Pro Asp Glu Ala Ser Glu Ala Phe
                605                 610                 615 agg aac tct tcc atg gcc ctt caa cag gca cat tta ttg aaa aac atg        2044
Arg Asn Ser Ser Met Ala Leu Gln Gln Ala His Leu Leu Lys Asn Met
            620                 625                 630 agt cac tgc agg cag cct tct gac agc agt gtt gat aaa ttt gtg ttg        2092
Ser His Cys Arg Gln Pro Ser Asp Ser Ser Val Asp Lys Phe Val Leu
635                 640                 645 aga gat gaa gct act gaa ccg ggt gat caa gaa aac aag cct tgc cgc        2140
Arg Asp Glu Ala Thr Glu Pro Gly Asp Gln Glu Asn Lys Pro Cys Arg
650                 655                 660                 665 atc aaa ggt gac att gga cag tcc act gat gat gac tct gca cct ctt        2188
Ile Lys Gly Asp Ile Gly Gln Ser Thr Asp Asp Asp Ser Ala Pro Leu
                670                 675                 680 gtc cat tgt gtc cgc ctt tta tct gct tcg ttt ttg cta aca ggg gga        2236
Val His Cys Val Arg Leu Leu Ser Ala Ser Phe Leu Leu Thr Gly Gly
            685                 690                 695 aaa aat gtg ctg gtt ccg gac agg gat gtg agg gtc agc gtg aag gcc        2284
Lys Asn Val Leu Val Pro Asp Arg Asp Val Arg Val Ser Val Lys Ala
                700                 705                 710 ctg gcc ctc agc tgt gtg gga gca gct gtg gcc ctc cac ccg gaa tct        2332
Leu Ala Leu Ser Cys Val Gly Ala Ala Val Ala Leu His Pro Glu Ser
                715                 720                 725 ttc ttc agc aaa ctc tat aaa gtt cct ctt gac acc acg gaa tac cct        2380
Phe Phe Ser Lys Leu Tyr Lys Val Pro Leu Asp Thr Thr Glu Tyr Pro
730                 735                 740                 745 gag gaa cag tat gtc tca gac atc ttg aac tac atc gat cat gga gac        2428
Glu Glu Gln Tyr Val Ser Asp Ile Leu Asn Tyr Ile Asp His Gly Asp
                750                 755                 760
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| cca | cag | gtt | cga | gga | gcc | act | gcc | att | ctc | tgt | ggg | acc | ctc | atc | tgc  | 2476 |
| Pro | Gln | Val | Arg | Gly | Ala | Thr | Ala | Ile | Leu | Cys | Gly | Thr | Leu | Ile | Cys  |      |
|     |     |     |     | 765 |     |     |     |     | 770 |     |     |     |     | 775 |      |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| tcc | atc | ctc | agc | agg | tcc | cgc | ttc | cac | gtg | gga | gat | tgg | atg | ggc | acc | 2524 |
| Ser | Ile | Leu | Ser | Arg | Ser | Arg | Phe | His | Val | Gly | Asp | Trp | Met | Gly | Thr |      |
|     |     |     | 780 |     |     |     |     | 785 |     |     |     |     | 790 |     |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| att | aga | acc | ctc | aca | gga | aat | aca | ttt | tct | ttg | gcg | gat | tgc | att | cct | 2572 |
| Ile | Arg | Thr | Leu | Thr | Gly | Asn | Thr | Phe | Ser | Leu | Ala | Asp | Cys | Ile | Pro |      |
|     | 795 |     |     |     |     | 800 |     |     |     |     | 805 |     |     |     |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| ttg | ctg | cgg | aaa | aca | ctg | aag | gat | gag | tct | tct | gtt | act | tgc | aag | tta | 2620 |
| Leu | Leu | Arg | Lys | Thr | Leu | Lys | Asp | Glu | Ser | Ser | Val | Thr | Cys | Lys | Leu |      |
| 810 |     |     |     |     | 815 |     |     |     |     | 820 |     |     |     |     | 825 |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| gct | tgt | aca | gct | gtg | agg | aac | tgt | gtc | atg | agt | ctc | tgc | agc | agc | agc | 2668 |
| Ala | Cys | Thr | Ala | Val | Arg | Asn | Cys | Val | Met | Ser | Leu | Cys | Ser | Ser | Ser |      |
|     |     |     |     | 830 |     |     |     |     | 835 |     |     |     |     | 840 |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| tac | agt | gag | tta | gga | ctg | cag | ctg | atc | atc | gat | gtg | ctg | act | ctg | agg | 2716 |
| Tyr | Ser | Glu | Leu | Gly | Leu | Gln | Leu | Ile | Ile | Asp | Val | Leu | Thr | Leu | Arg |      |
|     |     |     | 845 |     |     |     |     | 850 |     |     |     |     | 855 |     |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| aac | agt | tcc | tat | tgg | ctg | gtg | agg | aca | gag | ctt | ctg | gaa | acc | ctt | gca | 2764 |
| Asn | Ser | Ser | Tyr | Trp | Leu | Val | Arg | Thr | Glu | Leu | Leu | Glu | Thr | Leu | Ala |      |
|     |     | 860 |     |     |     |     | 865 |     |     |     |     | 870 |     |     |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| gag | att | gac | ttc | agg | ctg | gtg | agc | ttt | ttg | gag | gca | aaa | gca | gaa | aac | 2812 |
| Glu | Ile | Asp | Phe | Arg | Leu | Val | Ser | Phe | Leu | Glu | Ala | Lys | Ala | Glu | Asn |      |
| 875 |     |     |     |     | 880 |     |     |     |     | 885 |     |     |     |     |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| tta | cac | aga | ggg | gct | cat | cat | tat | aca | ggg | ctt | tta | aaa | ctg | caa | gaa | 2860 |
| Leu | His | Arg | Gly | Ala | His | His | Tyr | Thr | Gly | Leu | Leu | Lys | Leu | Gln | Glu |      |
| 890 |     |     |     |     | 895 |     |     |     |     | 900 |     |     |     |     | 905 |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| cga | gtg | ctc | aat | aat | gtt | gtc | atc | cat | ttg | ctt | gga | gat | gaa | gac | ccc | 2908 |
| Arg | Val | Leu | Asn | Asn | Val | Val | Ile | His | Leu | Leu | Gly | Asp | Glu | Asp | Pro |      |
|     |     |     |     | 910 |     |     |     |     | 915 |     |     |     |     | 920 |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| agg | gtg | cga | cat | gtt | gcc | gca | gca | tca | cta | att | agg | ctt | gtc | cca | aag | 2956 |
| Arg | Val | Arg | His | Val | Ala | Ala | Ala | Ser | Leu | Ile | Arg | Leu | Val | Pro | Lys |      |
|     |     |     |     | 925 |     |     |     |     | 930 |     |     |     |     | 935 |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| ctg | ttt | tat | aaa | tgt | gac | caa | gga | caa | gct | gat | cca | gta | gtg | gcc | gtg | 3004 |
| Leu | Phe | Tyr | Lys | Cys | Asp | Gln | Gly | Gln | Ala | Asp | Pro | Val | Val | Ala | Val |      |
|     |     |     | 940 |     |     |     |     | 945 |     |     |     |     | 950 |     |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| gca | aga | gat | caa | agc | agt | gtt | tac | ctg | aaa | ctt | ctc | atg | cat | gag | acg | 3052 |
| Ala | Arg | Asp | Gln | Ser | Ser | Val | Tyr | Leu | Lys | Leu | Leu | Met | His | Glu | Thr |      |
| 955 |     |     |     |     | 960 |     |     |     |     | 965 |     |     |     |     |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| cag | cct | cca | tct | cat | ttc | tcc | gtc | agc | aca | ata | acc | aga | ata | tat | aga | 3100 |
| Gln | Pro | Pro | Ser | His | Phe | Ser | Val | Ser | Thr | Ile | Thr | Arg | Ile | Tyr | Arg |      |
| 970 |     |     |     |     | 975 |     |     |     |     | 980 |     |     |     |     | 985 |      |

|     |     |     |     |     |     |     |     |     |     |     |     |     |     |     |      |      |
| --- | --- | --- | --- | --- | --- | --- | --- | --- | --- | --- | --- | --- | --- | --- | ---- | ---- |
| ggc | tat | aac | cta | cta | cca | agc | ata | aca | gac | gtc | act | atg | gaa | aat | aac  | 3148 |
| Gly | Tyr | Asn | Leu | Leu | Pro | Ser | Ile | Thr | Asp | Val | Thr | Met | Glu | Asn | Asn  |      |
|     |     |     |     | 990 |     |     |     |     | 995 |     |     |     |     |     | 1000 |      |

|     |      |     |      |     |     |     |     |      |     |     |     |     |      |     |      |
| --- | ---- | --- | ---- | --- | --- | --- | --- | ---- | --- | --- | --- | --- | ---- | --- | ---- |
| ctt | tca  | aga | gtt  | att | gca | gca | gtt | tct  | cat | gaa | cta | atc | aca  | tca | 3193 |
| Leu | Ser  | Arg | Val  | Ile | Ala | Ala | Val | Ser  | His | Glu | Leu | Ile | Thr  | Ser |      |
|     |      |     | 1005 |     |     |     |     | 1010 |     |     |     |     | 1015 |     |      |

|     |      |     |     |     |      |     |     |     |      |     |     |     |      |     |      |
| --- | ---- | --- | --- | --- | ---- | --- | --- | --- | ---- | --- | --- | --- | ---- | --- | ---- |
| acc | acc  | aga | gca | ctc | aca  | ttt | gga | tgc | tgt  | gaa | gct | ttg | tgt  | ctt | 3238 |
| Thr | Thr  | Arg | Ala | Leu | Thr  | Phe | Gly | Cys | Cys  | Glu | Ala | Leu | Cys  | Leu |      |
|     | 1020 |     |     |     |      |     |     |     | 1025 |     |     |     | 1030 |     |      |

|     |     |     |      |     |     |     |     |      |     |     |     |     |      |     |      |
| --- | --- | --- | ---- | --- | --- | --- | --- | ---- | --- | --- | --- | --- | ---- | --- | ---- |
| ctt | tcc | act | gcc  | ttc | cca | gtt | tgc | att  | tgg | agt | tta | ggt | tgg  | cac | 3283 |
| Leu | Ser | Thr | Ala  | Phe | Pro | Val | Cys | Ile  | Trp | Ser | Leu | Gly | Trp  | His |      |
|     |     |     | 1035 |     |     |     |     | 1040 |     |     |     |     | 1045 |     |      |

|     |     |     |      |     |     |     |      |     |     |     |     |      |     |     |      |
| --- | --- | --- | ---- | --- | --- | --- | ---- | --- | --- | --- | --- | ---- | --- | --- | ---- |
| tgt | gga | gtg | cct  | cca | ctg | agt | gcc  | tca | gat | gag | tct | agg  | aag | agc | 3328 |
| Cys | Gly | Val | Pro  | Pro | Leu | Ser | Ala  | Ser | Asp | Glu | Ser | Arg  | Lys | Ser |      |
|     |     |     | 1050 |     |     |     | 1055 |     |     |     |     | 1060 |     |     |      |

|     |     |     |      |     |     |     |     |      |     |     |     |     |      |     |      |
| --- | --- | --- | ---- | --- | --- | --- | --- | ---- | --- | --- | --- | --- | ---- | --- | ---- |
| tgt | acc | gtt | ggg  | atg | gcc | aca | atg | att  | ctg | acc | ctg | ctc | tcg  | tca | 3373 |
| Cys | Thr | Val | Gly  | Met | Ala | Thr | Met | Ile  | Leu | Thr | Leu | Leu | Ser  | Ser |      |
|     |     |     | 1065 |     |     |     |     | 1070 |     |     |     |     | 1075 |     |      |

| | | | | | | | | | | |
|---|---|---|---|---|---|---|---|---|---|---|
| gct | tgg | ttc | cca | ttg | gat | ctc | tca | gcc | cat | caa | gat | gct | ttg | att | 3418 |
| Ala | Trp | Phe | Pro | Leu | Asp | Leu | Ser | Ala | His | Gln | Asp | Ala | Leu | Ile | |
| | | | 1080 | | | | 1085 | | | | 1090 | | | | |

```
gct tgg ttc cca ttg gat ctc tca gcc cat caa gat gct ttg att      3418
Ala Trp Phe Pro Leu Asp Leu Ser Ala His Gln Asp Ala Leu Ile
            1080            1085            1090 ttg gcc gga aac ttg ctt gca gcc agt gct ccc aaa tct ctg aga      3463
Leu Ala Gly Asn Leu Leu Ala Ala Ser Ala Pro Lys Ser Leu Arg
            1095            1100            1105 agt tca tgg gcc tct gaa gaa gaa gcc aac cca gca gcc acc aag      3508
Ser Ser Trp Ala Ser Glu Glu Glu Ala Asn Pro Ala Ala Thr Lys
            1110            1115            1120 caa gag gag gtc tgg cca gcc ctg ggg gac cgg gcc ctg gtg ccc      3553
Gln Glu Glu Val Trp Pro Ala Leu Gly Asp Arg Ala Leu Val Pro
            1125            1130            1135 atg gtg gag cag ctc ttc tct cac ctg ctg aag gtg att aac att      3598
Met Val Glu Gln Leu Phe Ser His Leu Leu Lys Val Ile Asn Ile
            1140            1145            1150 tgt gcc cac gtc ctg gat gac gtg gct cct gga ccc gca ata aag      3643
Cys Ala His Val Leu Asp Asp Val Ala Pro Gly Pro Ala Ile Lys
            1155            1160            1165 gca gcc ttg cct tct cta aca aac ccc cct tct cta agt ccc atc      3688
Ala Ala Leu Pro Ser Leu Thr Asn Pro Pro Ser Leu Ser Pro Ile
            1170            1175            1180 cga cga aag ggg aag gag aaa gaa cca gga gaa caa gca tct gta      3733
Arg Arg Lys Gly Lys Glu Lys Glu Pro Gly Glu Gln Ala Ser Val
            1185            1190            1195 ccg ttg agt ccc aag aaa ggc agt gag gcc agt gca gct tct aga      3778
Pro Leu Ser Pro Lys Lys Gly Ser Glu Ala Ser Ala Ala Ser Arg
            1200            1205            1210 caa tct gat acc tca ggt cct gtt aca aca agt aaa tcc tca tca      3823
Gln Ser Asp Thr Ser Gly Pro Val Thr Thr Ser Lys Ser Ser Ser
            1215            1220            1225 ctg ggg agt ttc tat cat ctt cct tca tac ctc aaa ctg cat gat      3868
Leu Gly Ser Phe Tyr His Leu Pro Ser Tyr Leu Lys Leu His Asp
            1230            1235            1240 gtc ctg aaa gct aca cac gct aac tac aag gtc acg ctg gat ctt      3913
Val Leu Lys Ala Thr His Ala Asn Tyr Lys Val Thr Leu Asp Leu
            1245            1250            1255 cag aac agc acg gaa aag ttt gga ggg ttt ctc cgc tca gcc ttg      3958
Gln Asn Ser Thr Glu Lys Phe Gly Gly Phe Leu Arg Ser Ala Leu
            1260            1265            1270 gat gtt ctt tct cag ata cta gag ctg gcc aca ctg cag gac att      4003
Asp Val Leu Ser Gln Ile Leu Glu Leu Ala Thr Leu Gln Asp Ile
            1275            1280            1285 ggg aag tgt gtt gaa gag atc cta gga tac ctg aaa tcc tgc ttt      4048
Gly Lys Cys Val Glu Glu Ile Leu Gly Tyr Leu Lys Ser Cys Phe
            1290            1295            1300 agt cga gaa cca atg atg gca act gtt tgt gtt caa caa ttg ttg      4093
Ser Arg Glu Pro Met Met Ala Thr Val Cys Val Gln Gln Leu Leu
            1305            1310            1315 aag act ctc ttt ggc aca aac ttg gcc tcc cag ttt gat ggc tta      4138
Lys Thr Leu Phe Gly Thr Asn Leu Ala Ser Gln Phe Asp Gly Leu
            1320            1325            1330 tct tcc aac ccc agc aag tca caa ggc cga gca cag cgc ctt ggc      4183
Ser Ser Asn Pro Ser Lys Ser Gln Gly Arg Ala Gln Arg Leu Gly
            1335            1340            1345 tcc tcc agt gtg agg cca ggc ttg tac cac tac tgc ttc atg gcc      4228
Ser Ser Ser Val Arg Pro Gly Leu Tyr His Tyr Cys Phe Met Ala
            1350            1355            1360 ccg tac acc cac ttc acc cag gcc ctc gct gac gcc agc ctg agg      4273
Pro Tyr Thr His Phe Thr Gln Ala Leu Ala Asp Ala Ser Leu Arg
```

-continued 1365                  1370                  1375 aac atg gtg cag   gcg gag cag gag   aac gac acc tcg   gga tgg ttt            4318
Asn Met Val Gln   Ala Glu Gln Glu   Asn Asp Thr Ser   Gly Trp Phe
                1380                  1385                  1390 gat gtc ctc cag   aaa gtg tct acc   cag ttg aag aca   aac ctc acg            4363
Asp Val Leu Gln   Lys Val Ser Thr   Gln Leu Lys Thr   Asn Leu Thr
                1395                  1400                  1405 agt gtc aca aag   aac cgt gca gat   aag aat gct att   cat aat cac            4408
Ser Val Thr Lys   Asn Arg Ala Asp   Lys Asn Ala Ile   His Asn His
                1410                  1415                  1420 att cgt ttg ttt   gaa cct ctt gtt   ata aaa gct tta   aaa cag tac            4453
Ile Arg Leu Phe   Glu Pro Leu Val   Ile Lys Ala Leu   Lys Gln Tyr
                1425                  1430                  1435 acg act aca aca   tgt gtg cag tta   cag aag cag gtt   tta gat ttg            4498
Thr Thr Thr Thr   Cys Val Gln Leu   Gln Lys Gln Val   Leu Asp Leu
                1440                  1445                  1450 ctg gcg cag ctg   gtt cag tta cgg   gtt aat tac tgt   ctt ctg gat            4543
Leu Ala Gln Leu   Val Gln Leu Arg   Val Asn Tyr Cys   Leu Leu Asp
                1455                  1460                  1465 tca gat cag gtg   ttt att ggc ttt   gta ttg aaa cag   ttt gaa tac            4588
Ser Asp Gln Val   Phe Ile Gly Phe   Val Leu Lys Gln   Phe Glu Tyr
                1470                  1475                  1480 att gaa gtg ggc   cag ttc agg gaa   tca gag gca atc   att cca aac            4633
Ile Glu Val Gly   Gln Phe Arg Glu   Ser Glu Ala Ile   Ile Pro Asn
                1485                  1490                  1495 atc ttt ttc ttc   ttg gta tta cta   tct tat gaa cgc   tat cat tca            4678
Ile Phe Phe Phe   Leu Val Leu Leu   Ser Tyr Glu Arg   Tyr His Ser
                1500                  1505                  1510 aaa cag atc att   gga att cct aaa   atc att cag ctc   tgt gat ggc            4723
Lys Gln Ile Ile   Gly Ile Pro Lys   Ile Ile Gln Leu   Cys Asp Gly
                1515                  1520                  1525 atc atg gcc agt   gga agg aag gct   gtg aca cat gcc   ata ccg gct            4768
Ile Met Ala Ser   Gly Arg Lys Ala   Val Thr His Ala   Ile Pro Ala
                1530                  1535                  1540 ctg cag ccc ata   gtc cac gac ctc   ttt gta tta aga   gga aca aat            4813
Leu Gln Pro Ile   Val His Asp Leu   Phe Val Leu Arg   Gly Thr Asn
                1545                  1550                  1555 aaa gct gat gca   gga aaa gag ctt   gaa acc caa aaa   gag gtg gtg            4858
Lys Ala Asp Ala   Gly Lys Glu Leu   Glu Thr Gln Lys   Glu Val Val
                1560                  1565                  1570 gtg tca atg tta   ctg aga ctc atc   cag tac cat cag   gtg ttg gag            4903
Val Ser Met Leu   Leu Arg Leu Ile   Gln Tyr His Gln   Val Leu Glu
                1575                  1580                  1585 atg ttc att ctt   gtc ctg cag cag   tgc cac aag gag   aat gaa gac            4948
Met Phe Ile Leu   Val Leu Gln Gln   Cys His Lys Glu   Asn Glu Asp
                1590                  1595                  1600 aag tgg aag cga   ctg tct cga cag   ata gct gac atc   atc ctc cca            4993
Lys Trp Lys Arg   Leu Ser Arg Gln   Ile Ala Asp Ile   Ile Leu Pro
                1605                  1610                  1615 atg tta gcc aaa   cag cag atg cac   att gac tct cat   gaa gcc ctt            5038
Met Leu Ala Lys   Gln Gln Met His   Ile Asp Ser His   Glu Ala Leu
                1620                  1625                  1630 gga gtg tta aat   aca tta ttt gag   att ttg gcc cct   tcc tcc ctc            5083
Gly Val Leu Asn   Thr Leu Phe Glu   Ile Leu Ala Pro   Ser Ser Leu
                1635                  1640                  1645 cgt ccg gta gac   atg ctt tta cgg   agt atg ttc gtc   act cca aac            5128
Arg Pro Val Asp   Met Leu Leu Arg   Ser Met Phe Val   Thr Pro Asn
                1650                  1655                  1660 aca atg gcg tcc   gtg agc act gtt   caa ctg tgg ata   tcg gga att            5173

|  |  |  |  |  |  |  |  |  |  |  |  |  |  |
|---|---|---|---|---|---|---|---|---|---|---|---|---|---|
| Thr | Met | Ala | Ser | Val | Ser | Thr | Val | Gln | Leu | Trp | Ile | Ser | Gly | Ile |
|  |  | 1665 |  |  |  | 1670 |  |  |  |  | 1675 |  |  |

| ctg | gcc | att | ttg | agg | gtt | ctg | att | tcc | cag | tca | act | gaa | gat | att | 5218 |
|---|---|---|---|---|---|---|---|---|---|---|---|---|---|---|---|
| Leu | Ala | Ile | Leu | Arg | Val | Leu | Ile | Ser | Gln | Ser | Thr | Glu | Asp | Ile |  |
|  |  | 1680 |  |  |  | 1685 |  |  |  |  | 1690 |  |  |  |  |

| gtt | ctt | tct | cgt | att | cag | gag | ctc | tcc | ttc | tct | ccg | tat | tta | atc | 5263 |
|---|---|---|---|---|---|---|---|---|---|---|---|---|---|---|---|
| Val | Leu | Ser | Arg | Ile | Gln | Glu | Leu | Ser | Phe | Ser | Pro | Tyr | Leu | Ile |  |
|  |  | 1695 |  |  |  | 1700 |  |  |  |  | 1705 |  |  |  |  |

| tcc | tgt | aca | gta | att | aat | agg | tta | aga | gat | ggg | gac | agt | act | tca | 5308 |
|---|---|---|---|---|---|---|---|---|---|---|---|---|---|---|---|
| Ser | Cys | Thr | Val | Ile | Asn | Arg | Leu | Arg | Asp | Gly | Asp | Ser | Thr | Ser |  |
|  |  | 1710 |  |  |  | 1715 |  |  |  |  | 1720 |  |  |  |  |

| acg | cta | gaa | gaa | cac | agt | gaa | ggg | aaa | caa | ata | aag | aat | ttg | cca | 5353 |
|---|---|---|---|---|---|---|---|---|---|---|---|---|---|---|---|
| Thr | Leu | Glu | Glu | His | Ser | Glu | Gly | Lys | Gln | Ile | Lys | Asn | Leu | Pro |  |
|  |  | 1725 |  |  |  | 1730 |  |  |  |  | 1735 |  |  |  |  |

| gaa | gaa | aca | ttt | tca | agg | ttt | cta | tta | caa | ctg | gtt | ggt | att | ctt | 5398 |
|---|---|---|---|---|---|---|---|---|---|---|---|---|---|---|---|
| Glu | Glu | Thr | Phe | Ser | Arg | Phe | Leu | Leu | Gln | Leu | Val | Gly | Ile | Leu |  |
|  |  | 1740 |  |  |  | 1745 |  |  |  |  | 1750 |  |  |  |  |

| tta | gaa | gac | att | gtt | aca | aaa | cag | ctg | aag | gtg | gaa | atg | agt | gag | 5443 |
|---|---|---|---|---|---|---|---|---|---|---|---|---|---|---|---|
| Leu | Glu | Asp | Ile | Val | Thr | Lys | Gln | Leu | Lys | Val | Glu | Met | Ser | Glu |  |
|  |  | 1755 |  |  |  | 1760 |  |  |  |  | 1765 |  |  |  |  |

| cag | caa | cat | act | ttc | tat | tgc | cag | gaa | cta | ggc | aca | ctg | cta | atg | 5488 |
|---|---|---|---|---|---|---|---|---|---|---|---|---|---|---|---|
| Gln | Gln | His | Thr | Phe | Tyr | Cys | Gln | Glu | Leu | Gly | Thr | Leu | Leu | Met |  |
|  |  | 1770 |  |  |  | 1775 |  |  |  |  | 1780 |  |  |  |  |

| tgt | ctg | atc | cac | atc | ttc | aag | tct | gga | atg | ttc | cgg | aga | atc | aca | 5533 |
|---|---|---|---|---|---|---|---|---|---|---|---|---|---|---|---|
| Cys | Leu | Ile | His | Ile | Phe | Lys | Ser | Gly | Met | Phe | Arg | Arg | Ile | Thr |  |
|  |  | 1785 |  |  |  | 1790 |  |  |  |  | 1795 |  |  |  |  |

| gca | gct | gcc | act | agg | ctg | ttc | cgc | agt | gat | ggc | tgt | ggc | ggc | agt | 5578 |
|---|---|---|---|---|---|---|---|---|---|---|---|---|---|---|---|
| Ala | Ala | Ala | Thr | Arg | Leu | Phe | Arg | Ser | Asp | Gly | Cys | Gly | Gly | Ser |  |
|  |  | 1800 |  |  |  | 1805 |  |  |  |  | 1810 |  |  |  |  |

| ttc | tac | acc | ctg | gac | agc | ttg | aac | ttg | cgg | gct | cgt | tcc | atg | atc | 5623 |
|---|---|---|---|---|---|---|---|---|---|---|---|---|---|---|---|
| Phe | Tyr | Thr | Leu | Asp | Ser | Leu | Asn | Leu | Arg | Ala | Arg | Ser | Met | Ile |  |
|  |  | 1815 |  |  |  | 1820 |  |  |  |  | 1825 |  |  |  |  |

| acc | acc | cac | ccg | gcc | ctg | gtg | ctg | ctc | tgg | tgt | cag | ata | ctg | ctg | 5668 |
|---|---|---|---|---|---|---|---|---|---|---|---|---|---|---|---|
| Thr | Thr | His | Pro | Ala | Leu | Val | Leu | Leu | Trp | Cys | Gln | Ile | Leu | Leu |  |
|  |  | 1830 |  |  |  | 1835 |  |  |  |  | 1840 |  |  |  |  |

| ctt | gtc | aac | cac | acc | gac | tac | cgc | tgg | tgg | gca | gaa | gtg | cag | cag | 5713 |
|---|---|---|---|---|---|---|---|---|---|---|---|---|---|---|---|
| Leu | Val | Asn | His | Thr | Asp | Tyr | Arg | Trp | Trp | Ala | Glu | Val | Gln | Gln |  |
|  |  | 1845 |  |  |  | 1850 |  |  |  |  | 1855 |  |  |  |  |

| acc | ccg | aaa | aga | cac | agt | ctg | tcc | agc | aca | aag | tta | ctt | agt | ccc | 5758 |
|---|---|---|---|---|---|---|---|---|---|---|---|---|---|---|---|
| Thr | Pro | Lys | Arg | His | Ser | Leu | Ser | Ser | Thr | Lys | Leu | Leu | Ser | Pro |  |
|  |  | 1860 |  |  |  | 1865 |  |  |  |  | 1870 |  |  |  |  |

| cag | atg | tct | gga | gaa | gag | gag | gat | tct | gac | ttg | gca | gcc | aaa | ctt | 5803 |
|---|---|---|---|---|---|---|---|---|---|---|---|---|---|---|---|
| Gln | Met | Ser | Gly | Glu | Glu | Glu | Asp | Ser | Asp | Leu | Ala | Ala | Lys | Leu |  |
|  |  | 1875 |  |  |  | 1880 |  |  |  |  | 1885 |  |  |  |  |

| gga | atg | tgc | aat | aga | gaa | ata | gta | cga | aga | ggg | gct | ctc | att | ctc | 5848 |
|---|---|---|---|---|---|---|---|---|---|---|---|---|---|---|---|
| Gly | Met | Cys | Asn | Arg | Glu | Ile | Val | Arg | Arg | Gly | Ala | Leu | Ile | Leu |  |
|  |  | 1890 |  |  |  | 1895 |  |  |  |  | 1900 |  |  |  |  |

| ttc | tgt | gat | tat | gtc | tgt | cag | aac | ctc | cat | gac | tcc | gag | cac | tta | 5893 |
|---|---|---|---|---|---|---|---|---|---|---|---|---|---|---|---|
| Phe | Cys | Asp | Tyr | Val | Cys | Gln | Asn | Leu | His | Asp | Ser | Glu | His | Leu |  |
|  |  | 1905 |  |  |  | 1910 |  |  |  |  | 1915 |  |  |  |  |

| acg | tgg | ctc | att | gta | aat | cac | att | caa | gat | ctg | atc | agc | ctt | tcc | 5938 |
|---|---|---|---|---|---|---|---|---|---|---|---|---|---|---|---|
| Thr | Trp | Leu | Ile | Val | Asn | His | Ile | Gln | Asp | Leu | Ile | Ser | Leu | Ser |  |
|  |  | 1920 |  |  |  | 1925 |  |  |  |  | 1930 |  |  |  |  |

| cac | gag | cct | cca | gta | cag | gac | ttc | atc | agt | gcc | gtt | cat | cgg | aac | 5983 |
|---|---|---|---|---|---|---|---|---|---|---|---|---|---|---|---|
| His | Glu | Pro | Pro | Val | Gln | Asp | Phe | Ile | Ser | Ala | Val | His | Arg | Asn |  |
|  |  | 1935 |  |  |  | 1940 |  |  |  |  | 1945 |  |  |  |  |

| tct | gct | gcc | agc | ggc | ctg | ttc | atc | cag | gca | att | cag | tct | cgt | tgt | 6028 |
|---|---|---|---|---|---|---|---|---|---|---|---|---|---|---|---|
| Ser | Ala | Ala | Ser | Gly | Leu | Phe | Ile | Gln | Ala | Ile | Gln | Ser | Arg | Cys |  |
|  |  | 1950 |  |  |  | 1955 |  |  |  |  | 1960 |  |  |  |  |

|  |  |  |  |  |  |  |  |  |  |  |  |  |
|---|---|---|---|---|---|---|---|---|---|---|---|---|
| gaa | aac | ctt | tca | act | cca | acc | atg | ctg | aag | aaa | act | ctt | cag | tgc | 6073 |
| Glu | Asn | Leu | Ser | Thr | Pro | Thr | Met | Leu | Lys | Lys | Thr | Leu | Gln | Cys | |
| | | | 1965 | | | | 1970 | | | | | 1975 | | | | ttg gag ggg atc cat ctc agc cag tcg gga gct gtg ctc acg ctg 6118
Leu Glu Gly Ile His Leu Ser Gln Ser Gly Ala Val Leu Thr Leu
            1980              1985                  1990 tat gtg gac agg ctt ctg tgc acc cct ttc cgt gtg ctg gct cgc 6163
Tyr Val Asp Arg Leu Leu Cys Thr Pro Phe Arg Val Leu Ala Arg
            1995              2000                  2005 atg gtc gac atc ctt gct tgt cgc cgg gta gaa atg ctt ctg gct 6208
Met Val Asp Ile Leu Ala Cys Arg Arg Val Glu Met Leu Leu Ala
            2010              2015                  2020 gca aat tta cag agc agc atg gcc cag ttg cca atg gaa gaa ctc 6253
Ala Asn Leu Gln Ser Ser Met Ala Gln Leu Pro Met Glu Glu Leu
            2025              2030                  2035 aac aga atc cag gaa tac ctt cag agc agc ggg ctc gct cag aga 6298
Asn Arg Ile Gln Glu Tyr Leu Gln Ser Ser Gly Leu Ala Gln Arg
            2040              2045                  2050 cac caa agg ctc tat tcc ctg ctg gac agg ttt cgt ctc tcc acc 6343
His Gln Arg Leu Tyr Ser Leu Leu Asp Arg Phe Arg Leu Ser Thr
            2055              2060                  2065 atg caa gac tca ctt agt ccc tct cct cca gtc tct tcc cac ccg 6388
Met Gln Asp Ser Leu Ser Pro Ser Pro Pro Val Ser Ser His Pro
            2070              2075                  2080 ctg gac ggg gat ggg cac gtg tca ctg gaa aca gtg agt ccg gac 6433
Leu Asp Gly Asp Gly His Val Ser Leu Glu Thr Val Ser Pro Asp
            2085              2090                  2095 aaa gac tgg tac gtt cat ctt gtc aaa tcc cag tgt tgg acc agg 6478
Lys Asp Trp Tyr Val His Leu Val Lys Ser Gln Cys Trp Thr Arg
            2100              2105                  2110 tca gat tct gca ctg ctg gaa ggt gca gag ctg gtg aat cgg att 6523
Ser Asp Ser Ala Leu Leu Glu Gly Ala Glu Leu Val Asn Arg Ile
            2115              2120                  2125 cct gct gaa gat atg aat gcc ttc atg atg aac tcg gag ttc aac 6568
Pro Ala Glu Asp Met Asn Ala Phe Met Met Asn Ser Glu Phe Asn
            2130              2135                  2140 cta agc ctg cta gct cca tgc tta agc cta ggg atg agt gaa att 6613
Leu Ser Leu Leu Ala Pro Cys Leu Ser Leu Gly Met Ser Glu Ile
            2145              2150                  2155 tct ggt ggc cag aag agt gcc ctt ttt gaa gca gcc cgt gag gtg 6658
Ser Gly Gly Gln Lys Ser Ala Leu Phe Glu Ala Ala Arg Glu Val
            2160              2165                  2170 act ctg gcc cgt gtg agc ggc acc gtg cag cag ctc cct gct gtc 6703
Thr Leu Ala Arg Val Ser Gly Thr Val Gln Gln Leu Pro Ala Val
            2175              2180                  2185 cat cat gtc ttc cag ccc gag ctg cct gca gag ccg gcg gcc tac 6748
His His Val Phe Gln Pro Glu Leu Pro Ala Glu Pro Ala Ala Tyr
            2190              2195                  2200 tgg agc aag ttg aat gat ctg ttt ggg gat gct gca ctg tat cag 6793
Trp Ser Lys Leu Asn Asp Leu Phe Gly Asp Ala Ala Leu Tyr Gln
            2205              2210                  2215 tcc ctg ccc act ctg gcc cgg gcc ctg gca cag tac ctg gtg gtg 6838
Ser Leu Pro Thr Leu Ala Arg Ala Leu Ala Gln Tyr Leu Val Val
            2220              2225                  2230 gtc tcc aaa ctg ccc agt cat ttg cac ctt cct cct gag aaa gag 6883
Val Ser Lys Leu Pro Ser His Leu His Leu Pro Pro Glu Lys Glu
            2235              2240                  2245 aag gac att gtg aaa ttc gtg gtg gca acc ctt gag gcc ctg tcc 6928
Lys Asp Ile Val Lys Phe Val Val Ala Thr Leu Glu Ala Leu Ser
            2250              2255                  2260

```
tgg cat ttg atc cat gag cag atc ccg ctg agt ctg gat ctc cag      6973
Trp His Leu Ile His Glu Gln Ile Pro Leu Ser Leu Asp Leu Gln
        2265                2270                2275 gca ggg ctg gac tgc tgc tgc ctg gcc ctg cag ctg cct ggc ctc      7018
Ala Gly Leu Asp Cys Cys Cys Leu Ala Leu Gln Leu Pro Gly Leu
        2280                2285                2290 tgg agc gtg gtc tcc tcc aca gag ttt gtg acc cac gcc tgc tcc      7063
Trp Ser Val Val Ser Ser Thr Glu Phe Val Thr His Ala Cys Ser
        2295                2300                2305 ctc atc tac tgt gtg cac ttc atc ctg gag gcc gtt gca gtg cag      7108
Leu Ile Tyr Cys Val His Phe Ile Leu Glu Ala Val Ala Val Gln
        2310                2315                2320 cct gga gag cag ctt ctt agt cca gaa aga agg aca aat acc cca      7153
Pro Gly Glu Gln Leu Leu Ser Pro Glu Arg Arg Thr Asn Thr Pro
        2325                2330                2335 aaa gcc atc agc gag gag gag gag gaa gta gat cca aac aca cag      7198
Lys Ala Ile Ser Glu Glu Glu Glu Glu Val Asp Pro Asn Thr Gln
        2340                2345                2350 aat cct aag tat atc act gca gcc tgt gag atg gtg gca gaa atg      7243
Asn Pro Lys Tyr Ile Thr Ala Ala Cys Glu Met Val Ala Glu Met
        2355                2360                2365 gtg gag tct ctg cag tcg gtg ttg gcc ttg ggt cat aaa agg aat      7288
Val Glu Ser Leu Gln Ser Val Leu Ala Leu Gly His Lys Arg Asn
        2370                2375                2380 agc ggc gtg ccg gcg ttt ctc acg cca ttg ctc agg aac atc atc      7333
Ser Gly Val Pro Ala Phe Leu Thr Pro Leu Leu Arg Asn Ile Ile
        2385                2390                2395 atc agc ctg gcc cgc ctg ccc ctt gtc aac agc tac aca cgt gtg      7378
Ile Ser Leu Ala Arg Leu Pro Leu Val Asn Ser Tyr Thr Arg Val
        2400                2405                2410 ccc cca ctg gtg tgg aag ctt gga tgg tca ccc aaa ccg gga ggg      7423
Pro Pro Leu Val Trp Lys Leu Gly Trp Ser Pro Lys Pro Gly Gly
        2415                2420                2425 gat ttt ggc aca gca ttc cct gag atc ccc gtg gag ttc ctc cag      7468
Asp Phe Gly Thr Ala Phe Pro Glu Ile Pro Val Glu Phe Leu Gln
        2430                2435                2440 gaa aag gaa gtc ttt aag gag ttc atc tac cgc atc aac aca cta      7513
Glu Lys Glu Val Phe Lys Glu Phe Ile Tyr Arg Ile Asn Thr Leu
        2445                2450                2455 ggc tgg acc agt cgt act cag ttt gaa gaa act tgg gcc acc ctc      7558
Gly Trp Thr Ser Arg Thr Gln Phe Glu Glu Thr Trp Ala Thr Leu
        2460                2465                2470 ctt ggt gtc ctg gtg acg cag ccc ctc gtg atg gag cag gag gag      7603
Leu Gly Val Leu Val Thr Gln Pro Leu Val Met Glu Gln Glu Glu
        2475                2480                2485 agc cca cca gaa gaa gac aca gag agg acc cag atc aac gtc ctg      7648
Ser Pro Pro Glu Glu Asp Thr Glu Arg Thr Gln Ile Asn Val Leu
        2490                2495                2500 gcc gtg cag gcc atc acc tca ctg gtg ctc agt gca atg act gtg      7693
Ala Val Gln Ala Ile Thr Ser Leu Val Leu Ser Ala Met Thr Val
        2505                2510                2515 cct gtg gcc ggc aac cca gct gta agc tgc ttg gag cag cag ccc      7738
Pro Val Ala Gly Asn Pro Ala Val Ser Cys Leu Glu Gln Gln Pro
        2520                2525                2530 cgg aac aag cct ctg aaa gct ctc gac acc agg ttt ggg agg aag      7783
Arg Asn Lys Pro Leu Lys Ala Leu Asp Thr Arg Phe Gly Arg Lys
        2535                2540                2545 ctg agc att atc aga ggg att gtg gag caa gag att caa gca atg      7828
Leu Ser Ile Ile Arg Gly Ile Val Glu Gln Glu Ile Gln Ala Met
```

```
                    2550              2555              2560
gtt tca aag aga gag aat att gcc acc cat cat tta tat cag gca    7873
Val Ser Lys Arg Glu Asn Ile Ala Thr His His Leu Tyr Gln Ala
            2565              2570              2575 tgg gat cct gtc cct tct ctg tct ccg gct act aca ggt gcc ctc    7918
Trp Asp Pro Val Pro Ser Leu Ser Pro Ala Thr Thr Gly Ala Leu
            2580              2585              2590 atc agc cac gag aag ctg ctg cta cag atc aac ccc gag cgg gag    7963
Ile Ser His Glu Lys Leu Leu Leu Gln Ile Asn Pro Glu Arg Glu
            2595              2600              2605 ctg ggg agc atg agc tac aaa ctc ggc cag gtg tcc ata cac tcc    8008
Leu Gly Ser Met Ser Tyr Lys Leu Gly Gln Val Ser Ile His Ser
            2610              2615              2620 gtg tgg ctg ggg aac agc atc aca ccc ctg agg gag gag gaa tgg    8053
Val Trp Leu Gly Asn Ser Ile Thr Pro Leu Arg Glu Glu Glu Trp
            2625              2630              2635 gac gag gaa gag gag gag gag gcc gac gcc cct gca cct tcg tca    8098
Asp Glu Glu Glu Glu Glu Glu Ala Asp Ala Pro Ala Pro Ser Ser
            2640              2645              2650 cca ccc acg tct cca gtc aac tcc agg aaa cac cgg gct gga gtt    8143
Pro Pro Thr Ser Pro Val Asn Ser Arg Lys His Arg Ala Gly Val
            2655              2660              2665 gac atc cac tcc tgt tcg cag ttt ttg ctt gag ttg tac agc cgc    8188
Asp Ile His Ser Cys Ser Gln Phe Leu Leu Glu Leu Tyr Ser Arg
            2670              2675              2680 tgg atc ctg ccg tcc agc tca gcc agg agg acc ccg gcc atc ctg    8233
Trp Ile Leu Pro Ser Ser Ser Ala Arg Arg Thr Pro Ala Ile Leu
            2685              2690              2695 atc agt gag gtg gtc aga tcc ctt cta gtg gtc tca gac ttg ttc    8278
Ile Ser Glu Val Val Arg Ser Leu Leu Val Val Ser Asp Leu Phe
            2700              2705              2710 acc gag cgc aac cag ttt gag ctg atg tat gtg acg ctg aca gaa    8323
Thr Glu Arg Asn Gln Phe Glu Leu Met Tyr Val Thr Leu Thr Glu
            2715              2720              2725 ctg cga agg gtg cac cct tca gaa gac gag atc ctc gct cag tac    8368
Leu Arg Arg Val His Pro Ser Glu Asp Glu Ile Leu Ala Gln Tyr
            2730              2735              2740 ctg gtg cct gcc acc tgc aag gca gct gcc gtc ctt ggg atg gac    8413
Leu Val Pro Ala Thr Cys Lys Ala Ala Ala Val Leu Gly Met Asp
            2745              2750              2755 aag gcc gtg gcg gag cct gtc agc cgc ctg ctg gag agc acg ctc    8458
Lys Ala Val Ala Glu Pro Val Ser Arg Leu Leu Glu Ser Thr Leu
            2760              2765              2770 agg agc agc cac ctg ccc agc agg gtt gga gcc ctg cac ggc gtc    8503
Arg Ser Ser His Leu Pro Ser Arg Val Gly Ala Leu His Gly Val
            2775              2780              2785 ctc tat gtg ctg gag tgc gac ctg ctg gac gac act gcc aag cag    8548
Leu Tyr Val Leu Glu Cys Asp Leu Leu Asp Asp Thr Ala Lys Gln
            2790              2795              2800 ctc atc ccg gtc atc agc gac tat ctc ctc tcc aac ctg aaa ggg    8593
Leu Ile Pro Val Ile Ser Asp Tyr Leu Leu Ser Asn Leu Lys Gly
            2805              2810              2815 atc gcc cac tgc gtg aac att cac agc cag cag cac gta ctg gtc    8638
Ile Ala His Cys Val Asn Ile His Ser Gln Gln His Val Leu Val
            2820              2825              2830 atg tgt gcc act gcg ttt tac ctc att gag aac tat cct ctg gac    8683
Met Cys Ala Thr Ala Phe Tyr Leu Ile Glu Asn Tyr Pro Leu Asp
            2835              2840              2845 gta ggg ccg gaa ttt tca gca tca ata ata cag atg tgt ggg gtg    8728
```

|     |     |     |     |     |     |     |     |     |     |     |     |       |
| --- | --- | --- | --- | --- | --- | --- | --- | --- | --- | --- | --- | ----- |
| Val | Gly | Pro | Glu | Phe | Ser | Ala | Ser | Ile | Ile | Gln | Met | Cys Gly Val |
|     |     |     | 2850 |    |     |     | 2855 |    |     |     | 2860 |      |

| atg | ctg | tct | gga | agt | gag | gag | tcc | acc | ccc | tcc | atc | att | tac | cac | 8773 |
| --- | --- | --- | --- | --- | --- | --- | --- | --- | --- | --- | --- | --- | --- | --- | --- |
| Met | Leu | Ser | Gly | Ser | Glu | Glu | Ser | Thr | Pro | Ser | Ile | Ile | Tyr | His |  |
|     |     |     | 2865 |    |     |     | 2870 |    |     |     | 2875 |    |     |     |  |

| tgt | gcc | ctc | aga | ggc | ctg | gag | cgc | ctc | ctg | ctc | tct | gag | cag | ctc | 8818 |
| --- | --- | --- | --- | --- | --- | --- | --- | --- | --- | --- | --- | --- | --- | --- | --- |
| Cys | Ala | Leu | Arg | Gly | Leu | Glu | Arg | Leu | Leu | Leu | Ser | Glu | Gln | Leu |  |
|     |     | 2880 |    |     |     | 2885 |    |     |     | 2890 |    |     |     |     |  |

| tcc | cgc | ctg | gat | gca | gaa | tcg | ctg | gtc | aag | ctg | agt | gtg | gac | aga | 8863 |
| --- | --- | --- | --- | --- | --- | --- | --- | --- | --- | --- | --- | --- | --- | --- | --- |
| Ser | Arg | Leu | Asp | Ala | Glu | Ser | Leu | Val | Lys | Leu | Ser | Val | Asp | Arg |  |
|     |     | 2895 |    |     |     | 2900 |    |     |     | 2905 |    |     |     |     |  |

| gtg | aac | gtg | cac | agc | ccg | cac | cgg | gcc | atg | gcg | gct | ctg | ggc | ctg | 8908 |
| --- | --- | --- | --- | --- | --- | --- | --- | --- | --- | --- | --- | --- | --- | --- | --- |
| Val | Asn | Val | His | Ser | Pro | His | Arg | Ala | Met | Ala | Ala | Leu | Gly | Leu |  |
|     |     | 2910 |    |     |     | 2915 |    |     |     | 2920 |    |     |     |     |  |

| atg | ctc | acc | tgc | atg | tac | aca | gga | aag | gag | aaa | gtc | agt | ccg | ggt | 8953 |
| --- | --- | --- | --- | --- | --- | --- | --- | --- | --- | --- | --- | --- | --- | --- | --- |
| Met | Leu | Thr | Cys | Met | Tyr | Thr | Gly | Lys | Glu | Lys | Val | Ser | Pro | Gly |  |
|     |     | 2925 |    |     |     | 2930 |    |     |     | 2935 |    |     |     |     |  |

| aga | act | tca | gac | cct | aat | cct | gca | gcc | ccc | gac | agc | gag | tca | gtg | 8998 |
| --- | --- | --- | --- | --- | --- | --- | --- | --- | --- | --- | --- | --- | --- | --- | --- |
| Arg | Thr | Ser | Asp | Pro | Asn | Pro | Ala | Ala | Pro | Asp | Ser | Glu | Ser | Val |  |
|     |     | 2940 |    |     |     | 2945 |    |     |     | 2950 |    |     |     |     |  |

| att | gtt | gct | atg | gag | cgg | gta | tct | gtt | ctt | ttt | gat | agg | atc | agg | 9043 |
| --- | --- | --- | --- | --- | --- | --- | --- | --- | --- | --- | --- | --- | --- | --- | --- |
| Ile | Val | Ala | Met | Glu | Arg | Val | Ser | Val | Leu | Phe | Asp | Arg | Ile | Arg |  |
|     |     | 2955 |    |     |     | 2960 |    |     |     | 2965 |    |     |     |     |  |

| aaa | ggc | ttt | cct | tgt | gaa | gcc | aga | gtg | gtg | gcc | agg | atc | ctg | ccc | 9088 |
| --- | --- | --- | --- | --- | --- | --- | --- | --- | --- | --- | --- | --- | --- | --- | --- |
| Lys | Gly | Phe | Pro | Cys | Glu | Ala | Arg | Val | Val | Ala | Arg | Ile | Leu | Pro |  |
|     |     | 2970 |    |     |     | 2975 |    |     |     | 2980 |    |     |     |     |  |

| cag | ttt | cta | gac | gac | ttc | ttc | cca | ccc | cag | gac | atc | atg | aac | aaa | 9133 |
| --- | --- | --- | --- | --- | --- | --- | --- | --- | --- | --- | --- | --- | --- | --- | --- |
| Gln | Phe | Leu | Asp | Asp | Phe | Phe | Pro | Pro | Gln | Asp | Ile | Met | Asn | Lys |  |
|     |     | 2985 |    |     |     | 2990 |    |     |     | 2995 |    |     |     |     |  |

| gtc | atc | gga | gag | ttt | ctg | tcc | aac | cag | cag | cca | tac | ccc | cag | ttc | 9178 |
| --- | --- | --- | --- | --- | --- | --- | --- | --- | --- | --- | --- | --- | --- | --- | --- |
| Val | Ile | Gly | Glu | Phe | Leu | Ser | Asn | Gln | Gln | Pro | Tyr | Pro | Gln | Phe |  |
|     |     | 3000 |    |     |     | 3005 |    |     |     | 3010 |    |     |     |     |  |

| atg | gcc | acc | gtg | gtg | tat | aag | gtg | ttt | cag | act | ctg | cac | agc | acc | 9223 |
| --- | --- | --- | --- | --- | --- | --- | --- | --- | --- | --- | --- | --- | --- | --- | --- |
| Met | Ala | Thr | Val | Val | Tyr | Lys | Val | Phe | Gln | Thr | Leu | His | Ser | Thr |  |
|     |     | 3015 |    |     |     | 3020 |    |     |     | 3025 |    |     |     |     |  |

| ggg | cag | tcg | tcc | atg | gtc | cgg | gac | tgg | gtc | atg | ctg | tcc | ctc | tcc | 9268 |
| --- | --- | --- | --- | --- | --- | --- | --- | --- | --- | --- | --- | --- | --- | --- | --- |
| Gly | Gln | Ser | Ser | Met | Val | Arg | Asp | Trp | Val | Met | Leu | Ser | Leu | Ser |  |
|     |     | 3030 |    |     |     | 3035 |    |     |     | 3040 |    |     |     |     |  |

| aac | ttc | acg | cag | agg | gcc | ccg | gtc | gcc | atg | gcc | acg | tgg | agc | ctc | 9313 |
| --- | --- | --- | --- | --- | --- | --- | --- | --- | --- | --- | --- | --- | --- | --- | --- |
| Asn | Phe | Thr | Gln | Arg | Ala | Pro | Val | Ala | Met | Ala | Thr | Trp | Ser | Leu |  |
|     |     | 3045 |    |     |     | 3050 |    |     |     | 3055 |    |     |     |     |  |

| tcc | tgc | ttc | ttt | gtc | agc | gcg | tcc | acc | agc | ccg | tgg | gtc | gcg | gcg | 9358 |
| --- | --- | --- | --- | --- | --- | --- | --- | --- | --- | --- | --- | --- | --- | --- | --- |
| Ser | Cys | Phe | Phe | Val | Ser | Ala | Ser | Thr | Ser | Pro | Trp | Val | Ala | Ala |  |
|     |     | 3060 |    |     |     | 3065 |    |     |     | 3070 |    |     |     |     |  |

| atc | ctc | cca | cat | gtc | atc | agc | agg | atg | ggc | aag | ctg | gag | cag | gtg | 9403 |
| --- | --- | --- | --- | --- | --- | --- | --- | --- | --- | --- | --- | --- | --- | --- | --- |
| Ile | Leu | Pro | His | Val | Ile | Ser | Arg | Met | Gly | Lys | Leu | Glu | Gln | Val |  |
|     |     | 3075 |    |     |     | 3080 |    |     |     | 3085 |    |     |     |     |  |

| gac | gtg | aac | ctt | ttc | tgc | ctg | gtc | gcc | aca | gac | ttc | tac | aga | cac | 9448 |
| --- | --- | --- | --- | --- | --- | --- | --- | --- | --- | --- | --- | --- | --- | --- | --- |
| Asp | Val | Asn | Leu | Phe | Cys | Leu | Val | Ala | Thr | Asp | Phe | Tyr | Arg | His |  |
|     |     | 3090 |    |     |     | 3095 |    |     |     | 3100 |    |     |     |     |  |

| cag | ata | gag | gag | gag | ctc | gac | cgc | agg | gcc | ttc | cag | tct | gtg | ctt | 9493 |
| --- | --- | --- | --- | --- | --- | --- | --- | --- | --- | --- | --- | --- | --- | --- | --- |
| Gln | Ile | Glu | Glu | Glu | Leu | Asp | Arg | Arg | Ala | Phe | Gln | Ser | Val | Leu |  |
|     |     | 3105 |    |     |     | 3110 |    |     |     | 3115 |    |     |     |     |  |

| gag | gtg | gtt | gca | gcc | cca | gga | agc | cca | tat | cac | cgg | ctg | ctg | act | 9538 |
| --- | --- | --- | --- | --- | --- | --- | --- | --- | --- | --- | --- | --- | --- | --- | --- |
| Glu | Val | Val | Ala | Ala | Pro | Gly | Ser | Pro | Tyr | His | Arg | Leu | Leu | Thr |  |
|     |     | 3120 |    |     |     | 3125 |    |     |     | 3130 |    |     |     |     |  |

| tgt | tta | cga | aat | gtc | cac | aag | gtc | acc | acc | tgc | tga | gcgccatggt | 9584 |
| --- | --- | --- | --- | --- | --- | --- | --- | --- | --- | --- | --- | --- | --- |
| Cys | Leu | Arg | Asn | Val | His | Lys | Val | Thr | Thr | Cys |     |     |     |
|     |     | 3135 |    |     |     |     | 3140 |    |     |     |     |     |

```
gggagagact gtgaggcggc agctggggcc ggagcctttg gaagtctgcg cccttgtgcc   9644
ctgcctccac cgagccagct tggtccctat gggcttccgc acatgccgcg ggcggccagg   9704
caacgtgcgt gtctctgcca tgtggcagaa gtgctctttg tggcagtggc caggcaggga   9764
gtgtctgcag tcctggtggg gctgagcctg aggccttcca gaaagcagga gcagctgtgc   9824
tgcaccccat gtgggtgacc aggtcctttc tcctgatagt cacctgctgg ttgttgccag   9884
gttgcagctg ctcttgcatc tgggccagaa gtcctccctc ctgcaggctg ctgttggcc    9944 cctctgctgt cctgcagtag aaggtgccgt gagcaggctt tgggaacact ggcctgggtc   10004
tccctggtgg ggtgtgcatg ccacgccccg tgtctggatg cacagatgcc atggcctgtg   10064
ctgggccagt ggctgggggt gctagacacc cggcaccatt ctcccttctc tcttttcttc   10124
tcaggattta aaatttaatt atatcagtaa agagattaat tttaacgtaa ctctttctat   10184
gcccgtgtaa agtatgtgaa tcgcaaggcc tgtgctgcat gcgacagcgt ccggggtggt   10244
ggacagggcc cccggccacg ctccctctcc tgtagccact ggcatagccc tcctgagcac   10304
ccgctgacat ttccgttgta catgttcctg tttatgcatt cacaaggtga ctgggatgta   10364
gagaggcgtt agtgggcagg tggccacagc aggactgagg acaggccccc attatcctag   10424
gggtgcgctc acctgcagcc cctcctcctc gggcacagac gactgtcgtt ctccacccac   10484
cagtcaggga cagcagcctc cctgtcactc agctgagaag gccagccctc cctggctgtg   10544
agcagcctcc actgtgtcca gagacatggg cctcccactc ctgttccttg ctagccctgg   10604
ggtggcgtct gcctaggagc tggctggcag gtgttgggac ctgctgctcc atggatgcat   10664
gccctaagag tgtcactgag ctgtgttttg tctgagcctc tctcggtcaa cagcaaagct   10724
tggtgtcttg gcactgttag tgacagagcc cagcatccct tctgccccg ttccagctga    10784 catcttgcac ggtgacccct tttagtcagg agagtgcaga tctgtgctca tcggagactg   10844
ccccacggcc ctgtcagagc cgccactcct atccccaggc caggtccctg gaccagcctc   10904
ctgtttgcag gcccagagga gccaagtcat taaaatggaa gtggattctg gatgccgggg   10964
ctgctgctga tgtaggagct ggatttggga gctctgcttg ccgactggct gtgagacgag   11024
gcaggggctc tgcttcctca gcccctagagg cgagccaggc aaggttggcg actgtcatgt   11084
ggcttggttt ggtcatgccc gtcgatgttt tgggtattga atgtggtaag tggaggaaat   11144
gttggaactc tgtgcaggtg ctgccttgag acccccaagc ttccacctgt ccctctccta   11204
tgtggcagct ggggagcagc tgagatgtgg acttgtatgc tgcccacata cgtgagggg    11264 agctgaaagg gagcccctcc tctgagcagc ctctgccagg cctgtatgag gcttttccca   11324
ccagctccca acagaggcct cccccagcca ggaccaccctc gtcctcgtgg cggggcagca   11384
ggagcggtag aaaggggtcc gatgtttgag gaggccctta agggaagcta ctgaattata   11444
acacgtaaga aaatcaccat tcttccgtat tggttggggg ctcctgtttc tcatcctagc   11504
tttttcctgg aaagcccgct agaaggtttg ggaacgaggg gaaagttctc agaactgttg   11564
gctgctcccc acccgcctcc cgcctccccc gcaggttatg tcagcagctc tgagacagca   11624
gtatcacagg ccagatgttg ttcctggcta gatgtttaca tttgtaagaa ataacactgt   11684
gaatgtaaaa cagagccatt cccttggaat gcatatcgct gggctcaaca tagagtttgt   11744
cttcctcttg tttacgacgt gatctaaacc agtccttagc aaggggctca gaacaccccg   11804
ctctggcagt aggtgtcccc cacccccaaa gacctgcctg tgtgctccgg agatgaatat   11864
gagctcatta gtaaaaatga cttcacccac gcatatacat aaagtatcca tgcatgtgca   11924
tatagacaca tctataattt tacacacaca cctctcaaga cggagatgca tggcctctaa   11984
```

-continued

```
gagtgcccgt gtcggttctt cctggaagtt gactttcctt agacccgcca ggtcaagtta    12044
gccgcgtgac ggacatccag gcgtgggacg tggtcagggc agggctcatt cattgcccac    12104
taggatccca ctggcgaaga tggtctccat atcagctctc tgcagaaggg aggaagactt    12164
tatcatgttc ctaaaaatct gtggcaagca cccatcgtat tatccaaatt ttgttgcaaa    12224
tgtgattaat ttggttgtca agttttgggg gtgggctgtg gggagattgc ttttgttttc    12284
ctgctggtaa tatcgggaaa gattttaatg aaaccagggt agaattgttt ggcaatgcac    12344
tgaagcgtgt ttctttccca aaatgtgcct cccttccgct gcgggcccag ctgagtctat    12404
gtaggtgatg tttccagctg ccaagtgctc tttgttactg tccaccctca tttctgccag    12464
cgcatgtgtc ctttcaaggg gaaaatgtga agctgaaccc cctccagaca cccagaatgt    12524
agcatctgag aaggccctgt gccctaaagg acacccctcg cccccatctt catggagggg    12584
gtcatttcag agccctcgga gccaatgaac agctcctcct cttggagctg agatgagccc    12644
cacgtggagc tcgggacgga tagtagacag caataactcg gtgtgtggcc gcctggcagg    12704
tggaacttcc tcccgttgcg gggtggagtg aggttagttc tgtgtgtctg gtgggtggag    12764
tcaggcttct cttgctacct gtgagcatcc ttcccagcag acatcctcat cgggctttgt    12824
ccctcccccg cttcctccct ctgcggggag gacccgggac cacagctgct ggccagggta    12884
gacttggagc tgtcctccag aggggtcacg tgtaggagtg agaagaagga agatcttgag    12944
agctgctgag ggaccttgga gagctcagga tggctcagac gaggacactc gcttgccggg    13004
cctgggcctc ctgggaagga gggagctgct cagaatgccg catgacaact gaaggcaacc    13064
tggaaggttc aggggccgct cttcccccat gtgcctgtca cgctctggtg cagtcaaagg    13124
aacgccttcc cctcagttgt ttctaagagc agagtctccc gctgcaatct gggtggtaac    13184
tgccagcctt ggaggatcgt ggccaacgtg gacctgccta cggagggtgg gctctgaccc    13244
aagtggggcc tccttgtcca ggtctcactg ctttgcaccg tggtcagagg gactgtcagc    13304
tgagcttgag ctcccctgga gccagcaggg ctgtgatggg cgagtcccgg agccccaccc    13364
agacctgaat gcttctgaga gcaaagggaa ggactgacga gagatgtata tttaattttt    13424
taactgctgc aaacattgta catccaaatt aaaggaaaaa aatggaaacc atcaaaaaaa    13484
aaaaaaaaaa a                                                        13495
```

<210> SEQ ID NO 8
<211> LENGTH: 3142
<212> TYPE: PRT
<213> ORGANISM: Homo sapiens

<400> SEQUENCE: 8

```
Met Ala Thr Leu Glu Lys Leu Met Lys Ala Phe Glu Ser Leu Lys Ser
1               5                   10                  15

Phe Gln Gln Gln Gln Gln Gln Gln Gln Gln Gln Gln Gln Gln Gln Gln
                20                  25                  30

Gln Gln Gln Gln Gln Gln Pro Pro Pro Pro Pro Pro Pro Pro Pro Pro
            35                  40                  45

Pro Gln Leu Pro Gln Pro Pro Pro Gln Ala Gln Pro Leu Leu Pro Gln
        50                  55                  60

Pro Gln Pro Pro Pro Pro Pro Pro Pro Pro Gly Pro Ala Val Ala Glu
65                  70                  75                  80

Ala Glu Glu Pro Leu His Arg Pro Lys Lys Glu Leu Ser Ala Thr Lys
                85                  90                  95
```

```
Lys Asp Arg Val Asn His Cys Leu Thr Ile Cys Glu Asn Ile Val Ala
                100                 105                 110

Gln Ser Val Arg Asn Ser Pro Glu Phe Gln Lys Leu Leu Gly Ile Ala
            115                 120                 125

Met Glu Leu Phe Leu Leu Cys Ser Asp Asp Ala Glu Ser Asp Val Arg
130                 135                 140

Met Val Ala Asp Glu Cys Leu Asn Lys Val Ile Lys Ala Leu Met Asp
145                 150                 155                 160

Ser Asn Leu Pro Arg Leu Gln Leu Glu Leu Tyr Lys Glu Ile Lys Lys
                165                 170                 175

Asn Gly Ala Pro Arg Ser Leu Arg Ala Ala Leu Trp Arg Phe Ala Glu
            180                 185                 190

Leu Ala His Leu Val Arg Pro Gln Lys Cys Arg Pro Tyr Leu Val Asn
        195                 200                 205

Leu Leu Pro Cys Leu Thr Arg Thr Ser Lys Arg Pro Glu Glu Ser Val
210                 215                 220

Gln Glu Thr Leu Ala Ala Ala Val Pro Lys Ile Met Ala Ser Phe Gly
225                 230                 235                 240

Asn Phe Ala Asn Asp Asn Glu Ile Lys Val Leu Leu Lys Ala Phe Ile
                245                 250                 255

Ala Asn Leu Lys Ser Ser Pro Thr Ile Arg Arg Thr Ala Ala Gly
            260                 265                 270

Ser Ala Val Ser Ile Cys Gln His Ser Arg Arg Thr Gln Tyr Phe Tyr
        275                 280                 285

Ser Trp Leu Leu Asn Val Leu Leu Gly Leu Leu Pro Val Glu Asp
290                 295                 300

Glu His Ser Thr Leu Leu Ile Leu Gly Val Leu Leu Thr Leu Arg Tyr
305                 310                 315                 320

Leu Val Pro Leu Leu Gln Gln Val Lys Asp Thr Ser Leu Lys Gly
                325                 330                 335

Ser Phe Gly Val Thr Arg Lys Glu Met Glu Val Ser Pro Ser Ala Glu
            340                 345                 350

Gln Leu Val Gln Val Tyr Glu Leu Thr Leu His His Thr Gln His Gln
        355                 360                 365

Asp His Asn Val Val Thr Gly Ala Leu Glu Leu Leu Gln Gln Leu Phe
        370                 375                 380

Arg Thr Pro Pro Pro Glu Leu Leu Gln Thr Leu Thr Ala Val Gly Gly
385                 390                 395                 400

Ile Gly Gln Leu Thr Ala Ala Lys Glu Glu Ser Gly Gly Arg Ser Arg
                405                 410                 415

Ser Gly Ser Ile Val Glu Leu Ile Ala Gly Gly Gly Ser Ser Cys Ser
            420                 425                 430

Pro Val Leu Ser Arg Lys Gln Lys Gly Lys Val Leu Leu Gly Glu Glu
        435                 440                 445

Glu Ala Leu Glu Asp Asp Ser Glu Ser Arg Ser Asp Val Ser Ser Ser
450                 455                 460

Ala Leu Thr Ala Ser Val Lys Asp Glu Ile Ser Gly Glu Leu Ala Ala
465                 470                 475                 480

Ser Ser Gly Val Ser Thr Pro Gly Ser Ala Gly His Asp Ile Ile Thr
                485                 490                 495

Glu Gln Pro Arg Ser Gln His Thr Leu Gln Ala Asp Ser Val Asp Leu
            500                 505                 510

Ala Ser Cys Asp Leu Thr Ser Ser Ala Thr Asp Gly Asp Glu Glu Asp
```

```
                515                 520                 525
Ile Leu Ser His Ser Ser Gln Val Ser Ala Val Pro Ser Asp Pro
            530                 535                 540
Ala Met Asp Leu Asn Asp Gly Thr Gln Ala Ser Ser Pro Ile Ser Asp
545                 550                 555                 560
Ser Ser Gln Thr Thr Thr Glu Gly Pro Asp Ser Ala Val Thr Pro Ser
                565                 570                 575
Asp Ser Ser Glu Ile Val Leu Asp Gly Thr Asp Asn Gln Tyr Leu Gly
            580                 585                 590
Leu Gln Ile Gly Gln Pro Gln Asp Glu Asp Glu Ala Thr Gly Ile
            595                 600                 605
Leu Pro Asp Glu Ala Ser Glu Ala Phe Arg Asn Ser Ser Met Ala Leu
            610                 615                 620
Gln Gln Ala His Leu Leu Lys Asn Met Ser His Cys Arg Gln Pro Ser
625                 630                 635                 640
Asp Ser Ser Val Asp Lys Phe Val Leu Arg Asp Glu Ala Thr Glu Pro
                645                 650                 655
Gly Asp Gln Glu Asn Lys Pro Cys Arg Ile Lys Gly Asp Ile Gly Gln
            660                 665                 670
Ser Thr Asp Asp Ser Ala Pro Leu Val His Cys Val Arg Leu Leu
            675                 680                 685
Ser Ala Ser Phe Leu Leu Thr Gly Gly Lys Asn Val Leu Val Pro Asp
690                 695                 700
Arg Asp Val Arg Val Ser Val Lys Ala Leu Ala Leu Ser Cys Val Gly
705                 710                 715                 720
Ala Ala Val Ala Leu His Pro Glu Ser Phe Phe Ser Lys Leu Tyr Lys
                725                 730                 735
Val Pro Leu Asp Thr Thr Glu Tyr Pro Glu Glu Gln Tyr Val Ser Asp
            740                 745                 750
Ile Leu Asn Tyr Ile Asp His Gly Asp Pro Gln Val Arg Gly Ala Thr
            755                 760                 765
Ala Ile Leu Cys Gly Thr Leu Ile Cys Ser Ile Leu Ser Arg Ser Arg
770                 775                 780
Phe His Val Gly Asp Trp Met Gly Thr Ile Arg Thr Leu Thr Gly Asn
785                 790                 795                 800
Thr Phe Ser Leu Ala Asp Cys Ile Pro Leu Leu Arg Lys Thr Leu Lys
                805                 810                 815
Asp Glu Ser Ser Val Thr Cys Lys Leu Ala Cys Thr Ala Val Arg Asn
            820                 825                 830
Cys Val Met Ser Leu Cys Ser Ser Tyr Ser Glu Leu Gly Leu Gln
            835                 840                 845
Leu Ile Ile Asp Val Leu Thr Leu Arg Asn Ser Ser Tyr Trp Leu Val
            850                 855                 860
Arg Thr Glu Leu Leu Glu Thr Leu Ala Glu Ile Asp Phe Arg Leu Val
865                 870                 875                 880
Ser Phe Leu Glu Ala Lys Ala Glu Asn Leu His Arg Gly Ala His His
                885                 890                 895
Tyr Thr Gly Leu Leu Lys Leu Gln Glu Arg Val Leu Asn Asn Val Val
            900                 905                 910
Ile His Leu Leu Gly Asp Glu Asp Pro Arg Val Arg His Val Ala Ala
            915                 920                 925
Ala Ser Leu Ile Arg Leu Val Pro Lys Leu Phe Tyr Lys Cys Asp Gln
            930                 935                 940
```

```
Gly Gln Ala Asp Pro Val Val Ala Val Ala Arg Asp Gln Ser Ser Val
945                 950                 955                 960

Tyr Leu Lys Leu Leu Met His Glu Thr Gln Pro Pro Ser His Phe Ser
            965                 970                 975

Val Ser Thr Ile Thr Arg Ile Tyr Arg Gly Tyr Asn Leu Leu Pro Ser
        980                 985                 990

Ile Thr Asp Val Thr Met Glu Asn Asn Leu Ser Arg Val Ile Ala Ala
        995                 1000                1005

Val Ser His Glu Leu Ile Thr Ser Thr Thr Arg Ala Leu Thr Phe
    1010                1015                1020

Gly Cys Cys Glu Ala Leu Cys Leu Leu Ser Thr Ala Phe Pro Val
    1025                1030                1035

Cys Ile Trp Ser Leu Gly Trp His Cys Gly Val Pro Pro Leu Ser
    1040                1045                1050

Ala Ser Asp Glu Ser Arg Lys Ser Cys Thr Val Gly Met Ala Thr
    1055                1060                1065

Met Ile Leu Thr Leu Leu Ser Ser Ala Trp Phe Pro Leu Asp Leu
    1070                1075                1080

Ser Ala His Gln Asp Ala Leu Ile Leu Ala Gly Asn Leu Leu Ala
    1085                1090                1095

Ala Ser Ala Pro Lys Ser Leu Arg Ser Ser Trp Ala Ser Glu Glu
    1100                1105                1110

Glu Ala Asn Pro Ala Ala Thr Lys Gln Glu Glu Val Trp Pro Ala
    1115                1120                1125

Leu Gly Asp Arg Ala Leu Val Pro Met Val Glu Gln Leu Phe Ser
    1130                1135                1140

His Leu Leu Lys Val Ile Asn Ile Cys Ala His Val Leu Asp Asp
    1145                1150                1155

Val Ala Pro Gly Pro Ala Ile Lys Ala Ala Leu Pro Ser Leu Thr
    1160                1165                1170

Asn Pro Pro Ser Leu Ser Pro Ile Arg Arg Lys Gly Lys Glu Lys
    1175                1180                1185

Glu Pro Gly Glu Gln Ala Ser Val Pro Leu Ser Pro Lys Lys Gly
    1190                1195                1200

Ser Glu Ala Ser Ala Ala Ser Arg Gln Ser Asp Thr Ser Gly Pro
    1205                1210                1215

Val Thr Thr Ser Lys Ser Ser Leu Gly Ser Phe Tyr His Leu
    1220                1225                1230

Pro Ser Tyr Leu Lys Leu His Asp Val Leu Lys Ala Thr His Ala
    1235                1240                1245

Asn Tyr Lys Val Thr Leu Asp Leu Gln Asn Ser Thr Glu Lys Phe
    1250                1255                1260

Gly Gly Phe Leu Arg Ser Ala Leu Asp Val Leu Ser Gln Ile Leu
    1265                1270                1275

Glu Leu Ala Thr Leu Gln Asp Ile Gly Lys Cys Val Glu Glu Ile
    1280                1285                1290

Leu Gly Tyr Leu Lys Ser Cys Phe Ser Arg Glu Pro Met Met Ala
    1295                1300                1305

Thr Val Cys Val Gln Gln Leu Leu Lys Thr Leu Phe Gly Thr Asn
    1310                1315                1320

Leu Ala Ser Gln Phe Asp Gly Leu Ser Ser Asn Pro Ser Lys Ser
    1325                1330                1335
```

```
Gln Gly Arg Ala Gln Arg Leu Gly Ser Ser Ser Val Arg Pro Gly
    1340                1345                1350

Leu Tyr His Tyr Cys Phe Met Ala Pro Tyr Thr His Phe Thr Gln
    1355                1360                1365

Ala Leu Ala Asp Ala Ser Leu Arg Asn Met Val Gln Ala Glu Gln
    1370                1375                1380

Glu Asn Asp Thr Ser Gly Trp Phe Asp Val Leu Gln Lys Val Ser
    1385                1390                1395

Thr Gln Leu Lys Thr Asn Leu Thr Ser Val Thr Lys Asn Arg Ala
    1400                1405                1410

Asp Lys Asn Ala Ile His Asn His Ile Arg Leu Phe Glu Pro Leu
    1415                1420                1425

Val Ile Lys Ala Leu Lys Gln Tyr Thr Thr Thr Cys Val Gln
    1430                1435                1440

Leu Gln Lys Gln Val Leu Asp Leu Leu Ala Gln Leu Val Gln Leu
    1445                1450                1455

Arg Val Asn Tyr Cys Leu Leu Asp Ser Asp Gln Val Phe Ile Gly
    1460                1465                1470

Phe Val Leu Lys Gln Phe Glu Tyr Ile Glu Val Gly Gln Phe Arg
    1475                1480                1485

Glu Ser Glu Ala Ile Ile Pro Asn Ile Phe Phe Phe Leu Val Leu
    1490                1495                1500

Leu Ser Tyr Glu Arg Tyr His Ser Lys Gln Ile Ile Gly Ile Pro
    1505                1510                1515

Lys Ile Ile Gln Leu Cys Asp Gly Ile Met Ala Ser Gly Arg Lys
    1520                1525                1530

Ala Val Thr His Ala Ile Pro Ala Leu Gln Pro Ile Val His Asp
    1535                1540                1545

Leu Phe Val Leu Arg Gly Thr Asn Lys Ala Asp Ala Gly Lys Glu
    1550                1555                1560

Leu Glu Thr Gln Lys Glu Val Val Val Ser Met Leu Leu Arg Leu
    1565                1570                1575

Ile Gln Tyr His Gln Val Leu Glu Met Phe Ile Leu Val Leu Gln
    1580                1585                1590

Gln Cys His Lys Glu Asn Glu Asp Lys Trp Lys Arg Leu Ser Arg
    1595                1600                1605

Gln Ile Ala Asp Ile Ile Leu Pro Met Leu Ala Lys Gln Gln Met
    1610                1615                1620

His Ile Asp Ser His Glu Ala Leu Gly Val Leu Asn Thr Leu Phe
    1625                1630                1635

Glu Ile Leu Ala Pro Ser Ser Leu Arg Pro Val Asp Met Leu Leu
    1640                1645                1650

Arg Ser Met Phe Val Thr Pro Asn Thr Met Ala Ser Val Ser Thr
    1655                1660                1665

Val Gln Leu Trp Ile Ser Gly Ile Leu Ala Ile Leu Arg Val Leu
    1670                1675                1680

Ile Ser Gln Ser Thr Glu Asp Ile Val Leu Ser Arg Ile Gln Glu
    1685                1690                1695

Leu Ser Phe Ser Pro Tyr Leu Ile Ser Cys Thr Val Ile Asn Arg
    1700                1705                1710

Leu Arg Asp Gly Asp Ser Thr Ser Thr Leu Glu Glu His Ser Glu
    1715                1720                1725

Gly Lys Gln Ile Lys Asn Leu Pro Glu Glu Thr Phe Ser Arg Phe
```

```
                1730               1735                1740
Leu Leu Gln Leu Val Gly Ile Leu Leu Glu Asp Ile Val Thr Lys
    1745                1750                1755
Gln Leu Lys Val Glu Met Ser Glu Gln Gln His Thr Phe Tyr Cys
    1760                1765                1770
Gln Glu Leu Gly Thr Leu Leu Met Cys Leu Ile His Ile Phe Lys
    1775                1780                1785
Ser Gly Met Phe Arg Arg Ile Thr Ala Ala Thr Arg Leu Phe
    1790                1795                1800
Arg Ser Asp Gly Cys Gly Gly Ser Phe Tyr Thr Leu Asp Ser Leu
    1805                1810                1815
Asn Leu Arg Ala Arg Ser Met Ile Thr Thr His Pro Ala Leu Val
    1820                1825                1830
Leu Leu Trp Cys Gln Ile Leu Leu Leu Val Asn His Thr Asp Tyr
    1835                1840                1845
Arg Trp Trp Ala Glu Val Gln Gln Thr Pro Lys Arg His Ser Leu
    1850                1855                1860
Ser Ser Thr Lys Leu Leu Ser Pro Gln Met Ser Gly Glu Glu Glu
    1865                1870                1875
Asp Ser Asp Leu Ala Ala Lys Leu Gly Met Cys Asn Arg Glu Ile
    1880                1885                1890
Val Arg Arg Gly Ala Leu Ile Leu Phe Cys Asp Tyr Val Cys Gln
    1895                1900                1905
Asn Leu His Asp Ser Glu His Leu Thr Trp Leu Ile Val Asn His
    1910                1915                1920
Ile Gln Asp Leu Ile Ser Leu Ser His Glu Pro Pro Val Gln Asp
    1925                1930                1935
Phe Ile Ser Ala Val His Arg Asn Ser Ala Ala Ser Gly Leu Phe
    1940                1945                1950
Ile Gln Ala Ile Gln Ser Arg Cys Glu Asn Leu Ser Thr Pro Thr
    1955                1960                1965
Met Leu Lys Lys Thr Leu Gln Cys Leu Glu Gly Ile His Leu Ser
    1970                1975                1980
Gln Ser Gly Ala Val Leu Thr Leu Tyr Val Asp Arg Leu Leu Cys
    1985                1990                1995
Thr Pro Phe Arg Val Leu Ala Arg Met Val Asp Ile Leu Ala Cys
    2000                2005                2010
Arg Arg Val Glu Met Leu Leu Ala Ala Asn Leu Gln Ser Ser Met
    2015                2020                2025
Ala Gln Leu Pro Met Glu Glu Leu Asn Arg Ile Gln Glu Tyr Leu
    2030                2035                2040
Gln Ser Ser Gly Leu Ala Gln Arg His Gln Arg Leu Tyr Ser Leu
    2045                2050                2055
Leu Asp Arg Phe Arg Leu Ser Thr Met Gln Asp Ser Leu Ser Pro
    2060                2065                2070
Ser Pro Pro Val Ser Ser His Pro Leu Asp Gly Asp Gly His Val
    2075                2080                2085
Ser Leu Glu Thr Val Ser Pro Asp Lys Asp Trp Tyr Val His Leu
    2090                2095                2100
Val Lys Ser Gln Cys Trp Thr Arg Ser Asp Ser Ala Leu Leu Glu
    2105                2110                2115
Gly Ala Glu Leu Val Asn Arg Ile Pro Ala Glu Asp Met Asn Ala
    2120                2125                2130
```

-continued

```
Phe Met Met Asn Ser Glu Phe Asn Leu Ser Leu Leu Ala Pro Cys
    2135            2140                2145

Leu Ser Leu Gly Met Ser Glu Ile Ser Gly Gly Gln Lys Ser Ala
    2150            2155                2160

Leu Phe Glu Ala Ala Arg Glu Val Thr Leu Ala Arg Val Ser Gly
    2165            2170                2175

Thr Val Gln Gln Leu Pro Ala Val His His Val Phe Gln Pro Glu
    2180            2185                2190

Leu Pro Ala Glu Pro Ala Ala Tyr Trp Ser Lys Leu Asn Asp Leu
    2195            2200                2205

Phe Gly Asp Ala Ala Leu Tyr Gln Ser Leu Pro Thr Leu Ala Arg
    2210            2215                2220

Ala Leu Ala Gln Tyr Leu Val Val Ser Lys Leu Pro Ser His
    2225            2230                2235

Leu His Leu Pro Pro Glu Lys Glu Lys Asp Ile Val Lys Phe Val
    2240            2245                2250

Val Ala Thr Leu Glu Ala Leu Ser Trp His Leu Ile His Glu Gln
    2255            2260                2265

Ile Pro Leu Ser Leu Asp Leu Gln Ala Gly Leu Asp Cys Cys Cys
    2270            2275                2280

Leu Ala Leu Gln Leu Pro Gly Leu Trp Ser Val Val Ser Ser Thr
    2285            2290                2295

Glu Phe Val Thr His Ala Cys Ser Leu Ile Tyr Cys Val His Phe
    2300            2305                2310

Ile Leu Glu Ala Val Ala Val Gln Pro Gly Glu Gln Leu Leu Ser
    2315            2320                2325

Pro Glu Arg Arg Thr Asn Thr Pro Lys Ala Ile Ser Glu Glu Glu
    2330            2335                2340

Glu Glu Val Asp Pro Asn Thr Gln Asn Pro Lys Tyr Ile Thr Ala
    2345            2350                2355

Ala Cys Glu Met Val Ala Glu Met Val Glu Ser Leu Gln Ser Val
    2360            2365                2370

Leu Ala Leu Gly His Lys Arg Asn Ser Gly Val Pro Ala Phe Leu
    2375            2380                2385

Thr Pro Leu Leu Arg Asn Ile Ile Ile Ser Leu Ala Arg Leu Pro
    2390            2395                2400

Leu Val Asn Ser Tyr Thr Arg Val Pro Pro Leu Val Trp Lys Leu
    2405            2410                2415

Gly Trp Ser Pro Lys Pro Gly Gly Asp Phe Gly Thr Ala Phe Pro
    2420            2425                2430

Glu Ile Pro Val Glu Phe Leu Gln Glu Lys Glu Val Phe Lys Glu
    2435            2440                2445

Phe Ile Tyr Arg Ile Asn Thr Leu Gly Trp Thr Ser Arg Thr Gln
    2450            2455                2460

Phe Glu Glu Thr Trp Ala Thr Leu Leu Gly Val Leu Val Thr Gln
    2465            2470                2475

Pro Leu Val Met Glu Gln Glu Glu Ser Pro Pro Glu Glu Asp Thr
    2480            2485                2490

Glu Arg Thr Gln Ile Asn Val Leu Ala Val Gln Ala Ile Thr Ser
    2495            2500                2505

Leu Val Leu Ser Ala Met Thr Val Pro Val Ala Gly Asn Pro Ala
    2510            2515                2520
```

```
Val Ser Cys Leu Glu Gln Gln Pro Arg Asn Lys Pro Leu Lys Ala
    2525                2530                2535

Leu Asp Thr Arg Phe Gly Arg Lys Leu Ser Ile Ile Arg Gly Ile
    2540                2545                2550

Val Glu Gln Glu Ile Gln Ala Met Val Ser Lys Arg Glu Asn Ile
    2555                2560                2565

Ala Thr His His Leu Tyr Gln Ala Trp Asp Pro Val Pro Ser Leu
    2570                2575                2580

Ser Pro Ala Thr Thr Gly Ala Leu Ile Ser His Glu Lys Leu Leu
    2585                2590                2595

Leu Gln Ile Asn Pro Glu Arg Glu Leu Gly Ser Met Ser Tyr Lys
    2600                2605                2610

Leu Gly Gln Val Ser Ile His Ser Val Trp Leu Gly Asn Ser Ile
    2615                2620                2625

Thr Pro Leu Arg Glu Glu Glu Trp Asp Glu Glu Glu Glu Glu Glu
    2630                2635                2640

Ala Asp Ala Pro Ala Pro Ser Ser Pro Pro Thr Ser Pro Val Asn
    2645                2650                2655

Ser Arg Lys His Arg Ala Gly Val Asp Ile His Ser Cys Ser Gln
    2660                2665                2670

Phe Leu Leu Glu Leu Tyr Ser Arg Trp Ile Leu Pro Ser Ser Ser
    2675                2680                2685

Ala Arg Arg Thr Pro Ala Ile Leu Ile Ser Glu Val Val Arg Ser
    2690                2695                2700

Leu Leu Val Val Ser Asp Leu Phe Thr Glu Arg Asn Gln Phe Glu
    2705                2710                2715

Leu Met Tyr Val Thr Leu Thr Glu Leu Arg Arg Val His Pro Ser
    2720                2725                2730

Glu Asp Glu Ile Leu Ala Gln Tyr Leu Val Pro Ala Thr Cys Lys
    2735                2740                2745

Ala Ala Ala Val Leu Gly Met Asp Lys Ala Val Ala Glu Pro Val
    2750                2755                2760

Ser Arg Leu Leu Glu Ser Thr Leu Arg Ser Ser His Leu Pro Ser
    2765                2770                2775

Arg Val Gly Ala Leu His Gly Val Leu Tyr Val Leu Glu Cys Asp
    2780                2785                2790

Leu Leu Asp Asp Thr Ala Lys Gln Leu Ile Pro Val Ile Ser Asp
    2795                2800                2805

Tyr Leu Leu Ser Asn Leu Lys Gly Ile Ala His Cys Val Asn Ile
    2810                2815                2820

His Ser Gln Gln His Val Leu Val Met Cys Ala Thr Ala Phe Tyr
    2825                2830                2835

Leu Ile Glu Asn Tyr Pro Leu Asp Val Gly Pro Glu Phe Ser Ala
    2840                2845                2850

Ser Ile Ile Gln Met Cys Gly Val Met Leu Ser Gly Ser Glu Glu
    2855                2860                2865

Ser Thr Pro Ser Ile Ile Tyr His Cys Ala Leu Arg Gly Leu Glu
    2870                2875                2880

Arg Leu Leu Leu Ser Glu Gln Leu Ser Arg Leu Asp Ala Glu Ser
    2885                2890                2895

Leu Val Lys Leu Ser Val Asp Arg Val Asn Val His Ser Pro His
    2900                2905                2910

Arg Ala Met Ala Ala Leu Gly Leu Met Leu Thr Cys Met Tyr Thr
```

```
                            2915                2920                2925

Gly Lys Glu Lys Val Ser Pro Gly Arg Thr Ser Asp Pro Asn Pro
    2930                2935                2940

Ala Ala Pro Asp Ser Glu Ser Val Ile Val Ala Met Glu Arg Val
    2945                2950                2955

Ser Val Leu Phe Asp Arg Ile Arg Lys Gly Phe Pro Cys Glu Ala
    2960                2965                2970

Arg Val Val Ala Arg Ile Leu Pro Gln Phe Leu Asp Asp Phe Phe
    2975                2980                2985

Pro Pro Gln Asp Ile Met Asn Lys Val Ile Gly Glu Phe Leu Ser
    2990                2995                3000

Asn Gln Gln Pro Tyr Pro Gln Phe Met Ala Thr Val Val Tyr Lys
    3005                3010                3015

Val Phe Gln Thr Leu His Ser Thr Gly Gln Ser Ser Met Val Arg
    3020                3025                3030

Asp Trp Val Met Leu Ser Leu Ser Asn Phe Thr Gln Arg Ala Pro
    3035                3040                3045

Val Ala Met Ala Thr Trp Ser Leu Ser Cys Phe Phe Val Ser Ala
    3050                3055                3060

Ser Thr Ser Pro Trp Val Ala Ala Ile Leu Pro His Val Ile Ser
    3065                3070                3075

Arg Met Gly Lys Leu Glu Gln Val Asp Val Asn Leu Phe Cys Leu
    3080                3085                3090

Val Ala Thr Asp Phe Tyr Arg His Gln Ile Glu Glu Glu Leu Asp
    3095                3100                3105

Arg Arg Ala Phe Gln Ser Val Leu Glu Val Val Ala Ala Pro Gly
    3110                3115                3120

Ser Pro Tyr His Arg Leu Leu Thr Cys Leu Arg Asn Val His Lys
    3125                3130                3135

Val Thr Thr Cys
    3140

<210> SEQ ID NO 9
<211> LENGTH: 3354
<212> TYPE: DNA
<213> ORGANISM: Homo sapiens
<220> FEATURE:
<221> NAME/KEY: CDS
<222> LOCATION: (148)..(2235)

<400> SEQUENCE: 9
agtttcctcg gcagcggtag gcgagagcac gcggaggagc gtgcgcgggg gccccgggag        60
acggcggcgg tggcggcgcg ggcagagcaa ggacgcggcg gatcccactc gcacagcagc       120
gcactcggtg ccccgcgcag ggtcgcg atg ctg ccc ggt ttg gca ctg ctc ctg      174
                              Met Leu Pro Gly Leu Ala Leu Leu Leu
                                1               5 ctg gcc gcc tgg acg gct cgg gcg ctg gag gta ccc act gat ggt aat        222
Leu Ala Ala Trp Thr Ala Arg Ala Leu Glu Val Pro Thr Asp Gly Asn
 10                  15                  20                  25 gct ggc ctg ctg gct gaa ccc cag att gcc atg ttc tgt ggc aga ctg        270
Ala Gly Leu Leu Ala Glu Pro Gln Ile Ala Met Phe Cys Gly Arg Leu
                 30                  35                  40 aac atg cac atg aat gtc cag aat ggg aag tgg gat tca gat cca tca        318
Asn Met His Met Asn Val Gln Asn Gly Lys Trp Asp Ser Asp Pro Ser
             45                  50                  55 ggg acc aaa acc tgc att gat acc aag gaa ggc atc ctg cag tat tgc        366
```

```
                Gly Thr Lys Thr Cys Ile Asp Thr Lys Glu Gly Ile Leu Gln Tyr Cys
                        60                  65                  70 caa gaa gtc tac cct gaa ctg cag atc acc aat gtg gta gaa gcc aac                414
Gln Glu Val Tyr Pro Glu Leu Gln Ile Thr Asn Val Val Glu Ala Asn
         75                  80                  85 caa cca gtg acc atc cag aac tgg tgc aag cgg ggc cgc aag cag tgc                462
Gln Pro Val Thr Ile Gln Asn Trp Cys Lys Arg Gly Arg Lys Gln Cys
 90                  95                 100                 105 aag acc cat ccc cac ttt gtg att ccc tac cgc tgc tta gtt ggt gag                510
Lys Thr His Pro His Phe Val Ile Pro Tyr Arg Cys Leu Val Gly Glu
                    110                 115                 120 ttt gta agt gat gcc ctt ctc gtt cct gac aag tgc aaa ttc tta cac                558
Phe Val Ser Asp Ala Leu Leu Val Pro Asp Lys Cys Lys Phe Leu His
                125                 130                 135 cag gag agg atg gat gtt tgc gaa act cat ctt cac tgg cac acc gtc                606
Gln Glu Arg Met Asp Val Cys Glu Thr His Leu His Trp His Thr Val
            140                 145                 150 gcc aaa gag aca tgc agt gag aag agt acc aac ttg cat gac tac ggc                654
Ala Lys Glu Thr Cys Ser Glu Lys Ser Thr Asn Leu His Asp Tyr Gly
        155                 160                 165 atg ttg ctg ccc tgc gga att gac aag ttc cga ggg gta gag ttt gtg                702
Met Leu Leu Pro Cys Gly Ile Asp Lys Phe Arg Gly Val Glu Phe Val
170                 175                 180                 185 tgt tgc cca ctg gct gaa gaa agt gac aat gtg gat tct gct gat gcg                750
Cys Cys Pro Leu Ala Glu Glu Ser Asp Asn Val Asp Ser Ala Asp Ala
                    190                 195                 200 gag gag gat gac tcg gat gtc tgg tgg ggc gga gca gac aca gac tat                798
Glu Glu Asp Asp Ser Asp Val Trp Trp Gly Gly Ala Asp Thr Asp Tyr
                205                 210                 215 gca gat ggg agt gaa gac aaa gta gta gaa gta gca gag gag gaa gaa                846
Ala Asp Gly Ser Glu Asp Lys Val Val Glu Val Ala Glu Glu Glu Glu
            220                 225                 230 gtg gct gag gtg gaa gaa gaa gaa gcc gat gat gac gag gac gat gag                894
Val Ala Glu Val Glu Glu Glu Glu Ala Asp Asp Asp Glu Asp Asp Glu
        235                 240                 245 gat ggt gat gag gta gag gaa gag gct gag gaa ccc tac gaa gaa gcc                942
Asp Gly Asp Glu Val Glu Glu Glu Ala Glu Glu Pro Tyr Glu Glu Ala
250                 255                 260                 265 aca gag aga acc acc agc att gcc acc acc acc acc acc aca gag                    990
Thr Glu Arg Thr Thr Ser Ile Ala Thr Thr Thr Thr Thr Thr Thr Glu
                    270                 275                 280 tct gtg gaa gag gtg gtt cga gtt cct aca aca gca gcc agt acc cct                1038
Ser Val Glu Glu Val Val Arg Val Pro Thr Thr Ala Ala Ser Thr Pro
                285                 290                 295 gat gcc gtt gac aag tat ctc gag aca cct ggg gat gag aat gaa cat                1086
Asp Ala Val Asp Lys Tyr Leu Glu Thr Pro Gly Asp Glu Asn Glu His
            300                 305                 310 gcc cat ttc cag aaa gcc aaa gag agg ctt gag gcc aag cac cga gag                1134
Ala His Phe Gln Lys Ala Lys Glu Arg Leu Glu Ala Lys His Arg Glu
        315                 320                 325 aga atg tcc cag gtc atg aga gaa tgg gaa gag gca gaa cgt caa gca                1182
Arg Met Ser Gln Val Met Arg Glu Trp Glu Glu Ala Glu Arg Gln Ala
330                 335                 340                 345 aag aac ttg cct aaa gct gat aag aag gca gtt atc cag cat ttc cag                1230
Lys Asn Leu Pro Lys Ala Asp Lys Lys Ala Val Ile Gln His Phe Gln
                    350                 355                 360 gag aaa gtg gaa tct ttg gaa cag gaa gca gcc aac gag aga cag cag                1278
Glu Lys Val Glu Ser Leu Glu Gln Glu Ala Ala Asn Glu Arg Gln Gln
                365                 370                 375
```

```
                                                         -continued
ctg gtg gag aca cac atg gcc aga gtg gaa gcc atg ctc aat gac cgc    1326
Leu Val Glu Thr His Met Ala Arg Val Glu Ala Met Leu Asn Asp Arg
        380                 385                 390 cgc cgc ctg gcc ctg gag aac tac atc acc gct ctg cag gct gtt cct    1374
Arg Arg Leu Ala Leu Glu Asn Tyr Ile Thr Ala Leu Gln Ala Val Pro
395                 400                 405 cct cgg cct cgt cac gtg ttc aat atg cta aag aag tat gtc cgc gca    1422
Pro Arg Pro Arg His Val Phe Asn Met Leu Lys Lys Tyr Val Arg Ala
410                 415                 420                 425 gaa cag aag gac aga cag cac acc cta aag cat ttc gag cat gtg cgc    1470
Glu Gln Lys Asp Arg Gln His Thr Leu Lys His Phe Glu His Val Arg
                430                 435                 440 atg gtg gat ccc aag aaa gcc gct cag atc cgg tcc cag gtt atg aca    1518
Met Val Asp Pro Lys Lys Ala Ala Gln Ile Arg Ser Gln Val Met Thr
                    445                 450                 455 cac ctc cgt gtg att tat gag cgc atg aat cag tct ctc tcc ctg ctc    1566
His Leu Arg Val Ile Tyr Glu Arg Met Asn Gln Ser Leu Ser Leu Leu
                        460                 465                 470 tac aac gtg cct gca gtg gcc gag gag att cag gat gaa gtt gat gag    1614
Tyr Asn Val Pro Ala Val Ala Glu Glu Ile Gln Asp Glu Val Asp Glu
475                 480                 485 ctg ctt cag aaa gag caa aac tat tca gat gac gtc ttg gcc aac atg    1662
Leu Leu Gln Lys Glu Gln Asn Tyr Ser Asp Asp Val Leu Ala Asn Met
490                 495                 500                 505 att agt gaa cca agg atc agt tac gga aac gat gct ctc atg cca tct    1710
Ile Ser Glu Pro Arg Ile Ser Tyr Gly Asn Asp Ala Leu Met Pro Ser
                510                 515                 520 ttg acc gaa acg aaa acc acc gtg gag ctc ctt ccc gtg aat gga gag    1758
Leu Thr Glu Thr Lys Thr Thr Val Glu Leu Leu Pro Val Asn Gly Glu
                    525                 530                 535 ttc agc ctg gac gat ctc cag ccg tgg cat tct ttt ggg gct gac tct    1806
Phe Ser Leu Asp Asp Leu Gln Pro Trp His Ser Phe Gly Ala Asp Ser
                        540                 545                 550 gtg cca gcc aac aca gaa aac gaa gtt gag cct gtt gat gcc cgc cct    1854
Val Pro Ala Asn Thr Glu Asn Glu Val Glu Pro Val Asp Ala Arg Pro
555                 560                 565 gct gcc gac cga gga ctg acc act cga cca ggt tct ggg ttg aca aat    1902
Ala Ala Asp Arg Gly Leu Thr Thr Arg Pro Gly Ser Gly Leu Thr Asn
570                 575                 580                 585 atc aag acg gag gag atc tct gaa gtg aag atg gat gca gaa ttc cga    1950
Ile Lys Thr Glu Glu Ile Ser Glu Val Lys Met Asp Ala Glu Phe Arg
                590                 595                 600 cat gac tca gga tat gaa gtt cat cat caa aaa ttg gtg ttc ttt gca    1998
His Asp Ser Gly Tyr Glu Val His His Gln Lys Leu Val Phe Phe Ala
                    605                 610                 615 gaa gat gtg ggt tca aac aaa ggt gca atc att gga ctc atg gtg ggc    2046
Glu Asp Val Gly Ser Asn Lys Gly Ala Ile Ile Gly Leu Met Val Gly
                        620                 625                 630 ggt gtt gtc ata gcg aca gtg atc gtc atc acc ttg gtg atg ctg aag    2094
Gly Val Val Ile Ala Thr Val Ile Val Ile Thr Leu Val Met Leu Lys
635                 640                 645 aag aaa cag tac aca tcc att cat cat ggt gtg gtg gag gtt gac gcc    2142
Lys Lys Gln Tyr Thr Ser Ile His His Gly Val Val Glu Val Asp Ala
650                 655                 660                 665 gct gtc acc cca gag gag cgc cac ctg tcc aag atg cag cag aac ggc    2190
Ala Val Thr Pro Glu Glu Arg His Leu Ser Lys Met Gln Gln Asn Gly
                670                 675                 680 tac gaa aat cca acc tac aag ttc ttt gag cag atg cag aac tag       2235
Tyr Glu Asn Pro Thr Tyr Lys Phe Phe Glu Gln Met Gln Asn
                    685                 690                 695
```

```
acccccgcca cagcagcctc tgaagttgga cagcaaaacc attgcttcac tacccatcgg    2295
tgtccattta tagaataatg tgggaagaaa caaacccgtt ttatgattta ctcattatcg    2355
ccttttgaca gctgtgctgt aacacaagta gatgcctgaa cttgaattaa tccacacatc    2415
agtaatgtat tctatctctc tttacatttt ggtctctata ctacattatt aatgggtttt    2475
gtgtactgta aagaatttag ctgtatcaaa ctagtgcatg aatagattct ctcctgatta    2535
tttatcacat agcccttag ccagttgtat attattcttg tggtttgtga cccaattaag     2595
tcctacttta catatgcttt aagaatcgat ggggatgct tcatgtgaac gtgggagttc      2655
agctgcttct cttgcctaag tattcctttc ctgatcacta tgcattttaa agttaaacat    2715
ttttaagtat ttcagatgct ttagagagat ttttttttcca tgactgcatt ttactgtaca   2775
gattgctgct tctgctatat ttgtgatata ggaattaaga ggatacacac gtttgtttct    2835
tcgtgcctgt tttatgtgca cacattaggc attgagactt caagcttttc ttttttttgtc  2895 cacgtatctt tgggtctttg ataaagaaaa gaatccctgt tcattgtaag cacttttacg    2955
gggcgggtgg ggaggggtgc tctgctggtc ttcaattacc aagaattctc caaaacaatt    3015
ttctgcagga tgattgtaca gaatcattgc ttatgacatg atcgctttct acactgtatt    3075
acataaataa attaaataaa ataaccccgg gcaagacttt tctttgaagg atgactacag    3135
acattaaata atcgaagtaa ttttgggtgg ggagaagagg cagattcaat tttcttaac    3195 cagtctgaag tttcatttat gatacaaaag aagatgaaaa tggaagtggc aatataaggg    3255
gatgaggaag gcatgcctgg acaaacccctt cttttaagat gtgtcttcaa tttgtataaa   3315
atggtgtttt catgtaaata aatacattct tggaggagc                           3354
```

<210> SEQ ID NO 10
<211> LENGTH: 695
<212> TYPE: PRT
<213> ORGANISM: Homo sapiens

<400> SEQUENCE: 10

```
Met Leu Pro Gly Leu Ala Leu Leu Leu Ala Ala Trp Thr Ala Arg
1               5                   10                  15

Ala Leu Glu Val Pro Thr Asp Gly Asn Ala Gly Leu Leu Ala Glu Pro
                20                  25                  30

Gln Ile Ala Met Phe Cys Gly Arg Leu Asn Met His Met Asn Val Gln
            35                  40                  45

Asn Gly Lys Trp Asp Ser Asp Pro Ser Gly Thr Lys Thr Cys Ile Asp
        50                  55                  60

Thr Lys Glu Gly Ile Leu Gln Tyr Cys Gln Glu Val Tyr Pro Glu Leu
65                  70                  75                  80

Gln Ile Thr Asn Val Val Glu Ala Asn Gln Pro Val Thr Ile Gln Asn
                85                  90                  95

Trp Cys Lys Arg Gly Arg Lys Gln Cys Lys Thr His Pro His Phe Val
            100                 105                 110

Ile Pro Tyr Arg Cys Leu Val Gly Glu Phe Val Ser Asp Ala Leu Leu
        115                 120                 125

Val Pro Asp Lys Cys Lys Phe Leu His Gln Glu Arg Met Asp Val Cys
    130                 135                 140

Glu Thr His Leu His Trp His Thr Val Ala Lys Glu Thr Cys Ser Glu
145                 150                 155                 160

Lys Ser Thr Asn Leu His Asp Tyr Gly Met Leu Leu Pro Cys Gly Ile
                165                 170                 175
```

```
Asp Lys Phe Arg Gly Val Glu Phe Val Cys Cys Pro Leu Ala Glu Glu
            180                 185                 190

Ser Asp Asn Val Asp Ser Ala Asp Ala Glu Glu Asp Asp Ser Asp Val
            195                 200                 205

Trp Trp Gly Gly Ala Asp Thr Asp Tyr Ala Asp Gly Ser Glu Asp Lys
    210                 215                 220

Val Val Glu Val Ala Glu Glu Glu Val Ala Glu Val Glu Glu
225                 230                 235                 240

Glu Ala Asp Asp Asp Glu Asp Asp Glu Asp Gly Asp Glu Val Glu Glu
                245                 250                 255

Glu Ala Glu Glu Pro Tyr Glu Glu Ala Thr Glu Arg Thr Thr Ser Ile
            260                 265                 270

Ala Thr Thr Thr Thr Thr Thr Glu Ser Val Glu Glu Val Val Arg
    275                 280                 285

Val Pro Thr Thr Ala Ala Ser Thr Pro Asp Ala Val Asp Lys Tyr Leu
    290                 295                 300

Glu Thr Pro Gly Asp Glu Asn Glu His Ala His Phe Gln Lys Ala Lys
305                 310                 315                 320

Glu Arg Leu Glu Ala Lys His Arg Glu Arg Met Ser Gln Val Met Arg
                325                 330                 335

Glu Trp Glu Glu Ala Glu Arg Gln Ala Lys Asn Leu Pro Lys Ala Asp
            340                 345                 350

Lys Lys Ala Val Ile Gln His Phe Gln Glu Lys Val Glu Ser Leu Glu
            355                 360                 365

Gln Glu Ala Ala Asn Glu Arg Gln Leu Val Glu Thr His Met Ala
    370                 375                 380

Arg Val Glu Ala Met Leu Asn Asp Arg Arg Leu Ala Leu Glu Asn
385                 390                 395                 400

Tyr Ile Thr Ala Leu Gln Ala Val Pro Pro Arg Pro Arg His Val Phe
                405                 410                 415

Asn Met Leu Lys Lys Tyr Val Arg Ala Glu Gln Lys Asp Arg Gln His
            420                 425                 430

Thr Leu Lys His Phe Glu His Val Arg Met Val Asp Pro Lys Lys Ala
        435                 440                 445

Ala Gln Ile Arg Ser Gln Val Met Thr His Leu Arg Val Ile Tyr Glu
    450                 455                 460

Arg Met Asn Gln Ser Leu Ser Leu Leu Tyr Asn Val Pro Ala Val Ala
465                 470                 475                 480

Glu Glu Ile Gln Asp Glu Val Asp Glu Leu Leu Gln Lys Glu Gln Asn
                485                 490                 495

Tyr Ser Asp Asp Val Leu Ala Asn Met Ile Ser Glu Pro Arg Ile Ser
            500                 505                 510

Tyr Gly Asn Asp Ala Leu Met Pro Ser Leu Thr Glu Thr Lys Thr Thr
    515                 520                 525

Val Glu Leu Leu Pro Val Asn Gly Glu Phe Ser Leu Asp Asp Leu Gln
    530                 535                 540

Pro Trp His Ser Phe Gly Ala Asp Ser Val Pro Ala Asn Thr Glu Asn
545                 550                 555                 560

Glu Val Glu Pro Val Asp Ala Arg Pro Ala Ala Asp Arg Gly Leu Thr
                565                 570                 575

Thr Arg Pro Gly Ser Gly Leu Thr Asn Ile Lys Thr Glu Glu Ile Ser
            580                 585                 590
```

```
Glu Val Lys Met Asp Ala Glu Phe Arg His Asp Ser Gly Tyr Glu Val
            595                 600                 605

His His Gln Lys Leu Val Phe Phe Ala Glu Asp Val Gly Ser Asn Lys
    610                 615                 620

Gly Ala Ile Ile Gly Leu Met Val Gly Gly Val Val Ile Ala Thr Val
625                 630                 635                 640

Ile Val Ile Thr Leu Val Met Leu Lys Lys Lys Gln Tyr Thr Ser Ile
                645                 650                 655

His His Gly Val Val Glu Val Asp Ala Ala Val Thr Pro Glu Glu Arg
            660                 665                 670

His Leu Ser Lys Met Gln Gln Asn Gly Tyr Glu Asn Pro Thr Tyr Lys
    675                 680                 685

Phe Phe Glu Gln Met Gln Asn
    690                 695

<210> SEQ ID NO 11
<211> LENGTH: 2479
<212> TYPE: DNA
<213> ORGANISM: Homo sapiens
<220> FEATURE:
<221> NAME/KEY: CDS
<222> LOCATION: (97)..(858)

<400> SEQUENCE: 11 cccctcggc  cccgcgcgtc  gcctgtcctc  cgagccagtc  gctgacagcc  gcggcgccgc       60
gagcttctcc  tctcctcacg  accgagagca  gtcatt atg gcg aac ctt ggc tgc        114
                                           Met Ala Asn Leu Gly Cys
                                             1               5 tgg atg ctg gtt ctc ttt gtg gcc aca tgg agt gac ctg ggc ctc tgc          162
Trp Met Leu Val Leu Phe Val Ala Thr Trp Ser Asp Leu Gly Leu Cys
             10                  15                  20 aag aag cgc ccg aag cct gga gga tgg aac act ggg ggc agc cga tac          210
Lys Lys Arg Pro Lys Pro Gly Gly Trp Asn Thr Gly Gly Ser Arg Tyr
         25                  30                  35 ccg ggg cag ggc agc cct gga ggc aac cgc tac cca cct cag ggc ggt          258
Pro Gly Gln Gly Ser Pro Gly Gly Asn Arg Tyr Pro Pro Gln Gly Gly
     40                  45                  50 ggt ggc tgg ggg cag cct cat ggt ggt ggc tgg ggg cag cct cat ggt          306
Gly Gly Trp Gly Gln Pro His Gly Gly Gly Trp Gly Gln Pro His Gly
55                  60                  65                  70 ggt ggc tgg ggg cag ccc cat ggt ggt ggc tgg gga cag cct cat ggt          354
Gly Gly Trp Gly Gln Pro His Gly Gly Gly Trp Gly Gln Pro His Gly
                 75                  80                  85 ggt ggc tgg ggt caa gga ggt ggc acc cac agt cag tgg aac aag ccg          402
Gly Gly Trp Gly Gln Gly Gly Gly Thr His Ser Gln Trp Asn Lys Pro
             90                  95                 100 agt aag cca aaa acc aac atg aag cac atg gct ggt gct gca gca gct          450
Ser Lys Pro Lys Thr Asn Met Lys His Met Ala Gly Ala Ala Ala Ala
        105                 110                 115 ggg gca gtg gtg ggg ggc ctt ggc ggc tac atg ctg gga agt gcc atg          498
Gly Ala Val Val Gly Gly Leu Gly Gly Tyr Met Leu Gly Ser Ala Met
    120                 125                 130 agc agg ccc atc ata cat ttc ggc agt gac tat gag gac cgt tac tat          546
Ser Arg Pro Ile Ile His Phe Gly Ser Asp Tyr Glu Asp Arg Tyr Tyr
135                 140                 145                 150 cgt gaa aac atg cac cgt tac ccc aac caa gtg tac tac agg ccc atg          594
Arg Glu Asn Met His Arg Tyr Pro Asn Gln Val Tyr Tyr Arg Pro Met
                155                 160                 165 gat gag tac agc aac cag aac aac ttt gtg cac gac tgc gtc aat atc          642
```

| | | | | | | | | | | | | | | |
|---|---|---|---|---|---|---|---|---|---|---|---|---|---|---|
| Asp | Glu | Tyr | Ser | Asn | Gln | Asn | Asn | Phe | Val | His | Asp | Cys | Val | Asn | Ile |
| | | | 170 | | | | | 175 | | | | 180 | | | |

| aca | atc | aag | cag | cac | acg | gtc | acc | aca | acc | acc | aag | ggg | gag | aac | ttc | 690 |
|---|---|---|---|---|---|---|---|---|---|---|---|---|---|---|---|---|
| Thr | Ile | Lys | Gln | His | Thr | Val | Thr | Thr | Thr | Thr | Lys | Gly | Glu | Asn | Phe | |
| | | 185 | | | | | 190 | | | | | 195 | | | | |

| acc | gag | acc | gac | gtt | aag | atg | atg | gag | cgc | gtg | gtt | gag | cag | atg | tgt | 738 |
|---|---|---|---|---|---|---|---|---|---|---|---|---|---|---|---|---|
| Thr | Glu | Thr | Asp | Val | Lys | Met | Met | Glu | Arg | Val | Val | Glu | Gln | Met | Cys | |
| | 200 | | | | | | 205 | | | | | 210 | | | | |

| atc | acc | cag | tac | gag | agg | gaa | tct | cag | gcc | tat | tac | cag | aga | gga | tcg | 786 |
|---|---|---|---|---|---|---|---|---|---|---|---|---|---|---|---|---|
| Ile | Thr | Gln | Tyr | Glu | Arg | Glu | Ser | Gln | Ala | Tyr | Tyr | Gln | Arg | Gly | Ser | |
| 215 | | | | | 220 | | | | | 225 | | | | | 230 | |

| agc | atg | gtc | ctc | ttc | tcc | tct | cca | cct | gtg | atc | ctc | ctg | atc | tct | ttc | 834 |
|---|---|---|---|---|---|---|---|---|---|---|---|---|---|---|---|---|
| Ser | Met | Val | Leu | Phe | Ser | Ser | Pro | Pro | Val | Ile | Leu | Leu | Ile | Ser | Phe | |
| | | | | 235 | | | | | 240 | | | | | 245 | | |

| ctc | atc | ttc | ctg | ata | gtg | gga | tga | ggaaggtctt | cctgttttca | ccatctttct | 888 |
|---|---|---|---|---|---|---|---|---|---|---|---|
| Leu | Ile | Phe | Leu | Ile | Val | Gly | | | | | |
| | | 250 | | | | | | | | | |

| aatctttttc | cagcttgagg | gaggcggtat | ccacctgcag | cccttttagt | ggtggtgtct | 948 |
|---|---|---|---|---|---|---|
| cactctttct | tctctctttg | tcccggatag | gctaatcaat | acccttggca | ctgatgggca | 1008 |
| ctggaaaaca | tagagtagac | ctgagatgct | ggtcaagccc | cctttgattg | agttcatcat | 1068 |
| gagccgttgc | taatgccagg | ccagtaaaag | tataacagca | ataaccatt | ggttaatctg | 1128 |
| gacttatttt | tggacttagt | gcaacaggtt | gaggctaaaa | caaatctcag | aacagtctga | 1188 |
| aatacctttg | cctggatacc | tctggctcct | tcagcagcta | gagctcagta | tactaatgcc | 1248 |
| ctatcttagt | agagatttca | tagctattta | gagatatttt | ccattttaag | aaaacccgac | 1308 |
| aacatttctg | ccaggtttgt | taggaggcca | catgatactt | attcaaaaaa | atcctagaga | 1368 |
| ttcttagctc | ttgggatgca | ggctcagccc | gctggagcat | gagctctgtg | tgtaccgaga | 1428 |
| actggggtga | tgttttactt | ttcacagtat | gggctacaca | gcagctgttc | aacaagagta | 1488 |
| aatattgtca | caacactgaa | cctctggcta | gaggacatat | tcacagtgaa | cataactgta | 1548 |
| acatatatga | aaggcttctg | ggacttgaaa | tcaaatgttt | gggaatggtg | cccttggagg | 1608 |
| caacctccca | ttttagatgt | ttaaaggacc | ctatatgtgg | cattcctttc | tttaaactat | 1668 |
| aggtaattaa | ggcagctgaa | aagtaaattg | ccttctagac | actgaaggca | aatctccttt | 1728 |
| gtccatttac | ctggaaacca | gaatgatttt | gacatacagg | agagctgcag | ttgtgaaagc | 1788 |
| accatcatca | tagaggatga | tgtaattaaa | aaatggtcag | tgtgcaaaga | aaagaactgc | 1848 |
| ttgcatttct | ttatttctgt | ctcataattg | tcaaaaacca | gaattaggtc | aagttcatag | 1908 |
| tttctgtaat | tggcttttga | atcaaagaat | agggagacaa | tctaaaaaat | atcttaggtt | 1968 |
| ggagatgaca | gaaatatgat | tgatttgaag | tggaaaaaga | aattctgtta | atgttaatta | 2028 |
| aagtaaaatt | attccctgaa | ttgtttgata | ttgtcaccta | gcagatatgt | attacttttc | 2088 |
| tgcaatgtta | ttattggctt | gcactttgtg | agtattctat | gtaaaaatat | atatgtatat | 2148 |
| aaaatatata | ttgcatagga | cagacttagg | agttttgttt | agagcagtta | acatctgaag | 2208 |
| tgtctaatgc | attaactttt | gtaaggtact | gaatacttaa | tatgtgggaa | acccttttgc | 2268 |
| gtggtcctta | ggcttacaat | gtgcactgaa | tcgtttcatg | taagaatcca | agtggacac | 2328 |
| cattaacagg | tctttgaaat | atgcatgtac | tttatatttt | ctatatttgt | aactttgcat | 2388 |
| gttcttgttt | tgttatataa | aaaattgta | aatgtttaat | atctgactga | aattaaacga | 2448 |
| gcgaagatga | gcaccaaaaa | aaaaaaaaaa | a | | | 2479 |

<210> SEQ ID NO 12

```
<211> LENGTH: 253
<212> TYPE: PRT
<213> ORGANISM: Homo sapiens

<400> SEQUENCE: 12

Met Ala Asn Leu Gly Cys Trp Met Leu Val Leu Phe Val Ala Thr Trp
1               5                   10                  15

Ser Asp Leu Gly Leu Cys Lys Lys Arg Pro Lys Pro Gly Gly Trp Asn
            20                  25                  30

Thr Gly Gly Ser Arg Tyr Pro Gly Gln Gly Ser Pro Gly Gly Asn Arg
        35                  40                  45

Tyr Pro Pro Gln Gly Gly Gly Trp Gly Gln Pro His Gly Gly Gly
    50                  55                  60

Trp Gly Gln Pro His Gly Gly Gly Trp Gly Gln Pro His Gly Gly Gly
65                  70                  75                  80

Trp Gly Gln Pro His Gly Gly Gly Trp Gly Gln Gly Gly Gly Thr His
                85                  90                  95

Ser Gln Trp Asn Lys Pro Ser Lys Pro Lys Thr Asn Met Lys His Met
            100                 105                 110

Ala Gly Ala Ala Ala Ala Gly Ala Val Val Gly Gly Leu Gly Gly Tyr
        115                 120                 125

Met Leu Gly Ser Ala Met Ser Arg Pro Ile Ile His Phe Gly Ser Asp
    130                 135                 140

Tyr Glu Asp Arg Tyr Tyr Arg Glu Asn Met His Arg Tyr Pro Asn Gln
145                 150                 155                 160

Val Tyr Tyr Arg Pro Met Asp Glu Tyr Ser Asn Gln Asn Asn Phe Val
                165                 170                 175

His Asp Cys Val Asn Ile Thr Ile Lys Gln His Thr Val Thr Thr Thr
            180                 185                 190

Thr Lys Gly Glu Asn Phe Thr Glu Thr Asp Val Lys Met Met Glu Arg
        195                 200                 205

Val Val Glu Gln Met Cys Ile Thr Gln Tyr Glu Arg Glu Ser Gln Ala
    210                 215                 220

Tyr Tyr Gln Arg Gly Ser Ser Met Val Leu Phe Ser Ser Pro Pro Val
225                 230                 235                 240

Ile Leu Leu Ile Ser Phe Leu Ile Phe Leu Ile Val Gly
                245                 250
```